(12) United States Patent
Divino et al.

(10) Patent No.: US 9,011,480 B2
(45) Date of Patent: Apr. 21, 2015

(54) ANEURYSM TREATMENT COILS

(75) Inventors: Vince Divino, Mission Viejo, CA (US); Richard Rhee, Anaheim, CA (US); Rich Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 79 days.

(21) Appl. No.: 13/355,295

(22) Filed: Jan. 20, 2012

(65) Prior Publication Data

US 2013/0190801 A1    Jul. 25, 2013

(51) Int. Cl.
*A61M 29/00* (2006.01)
*A61B 17/12* (2006.01)
*A61B 17/00* (2006.01)

(52) U.S. Cl.
CPC ..... *A61B 17/12031* (2013.01); *A61B 17/12113* (2013.01); *A61B 17/12145* (2013.01); *A61B 17/12154* (2013.01); *A61B 2017/00526* (2013.01); *A61B 2017/00778* (2013.01); *A61B 2017/00867* (2013.01); *A61B 2017/12054* (2013.01)

(58) Field of Classification Search
USPC ........................................................ 606/200
See application file for complete search history.

(56) References Cited

U.S. PATENT DOCUMENTS

| | | | |
|---|---|---|---|
| 3,334,629 A | 8/1967 | Colm | |
| 3,834,394 A | 9/1974 | Hunter et al. | |
| 4,085,757 A | 4/1978 | Pevsner | |
| 4,282,875 A | 8/1981 | Serbinenko et al. | |
| 4,311,146 A | 1/1982 | Wonder | |
| 4,327,734 A | 5/1982 | White, Jr. | |
| 4,341,218 A | 7/1982 | U | |
| 4,346,712 A | 8/1982 | Handa et al. | |
| 4,364,392 A | 12/1982 | Strother et al. | |
| 4,402,319 A | 9/1983 | Handa et al. | |
| 4,441,495 A | 4/1984 | Hicswa | |
| 4,494,531 A | 1/1985 | Gianturco | |
| 4,517,979 A | 5/1985 | Pecenka | |
| 4,545,367 A | 10/1985 | Tucci | |
| 4,638,803 A | 1/1987 | Rand | |
| 4,719,924 A * | 1/1988 | Crittenden et al. | 600/585 |
| 4,735,201 A | 4/1988 | O'Reilly | |
| 4,745,919 A | 5/1988 | Bundy et al. | |
| 4,781,177 A | 11/1988 | Lebigot | |

(Continued)

FOREIGN PATENT DOCUMENTS

| | | |
|---|---|---|
| CA | 2144725 | 5/1994 |
| CA | 2144725 A1 | 5/1994 |

(Continued)

OTHER PUBLICATIONS

U.S. Appl. No. 13/764,028, filed Feb. 11, 2013.

*Primary Examiner* — Dianne Dornbusch
*Assistant Examiner* — Michael Mendoza
(74) *Attorney, Agent, or Firm* — Elizabeth A. O'Brien, Esq.

(57) ABSTRACT

Systems and devices for endovascular treatment of intracranial aneurysms are described. Various configurations of coiled implants may be used as stenting devices or aneurysm coils. The implants include one or more filaments wound about a longitudinal axis to form a generally tubular shape. Lateral flexibility of the implants may be manipulated by, for example, adjusting a pitch between adjacent filaments, using different materials for the filaments, employing different filament cross-sectional shapes, grouping filaments into pluralities of varying flexibilities, and nesting inner coils within outer coils.

16 Claims, 19 Drawing Sheets

(56) References Cited

U.S. PATENT DOCUMENTS

| | | |
|---|---|---|
| 4,787,899 A | 11/1988 | Lazarus |
| 4,819,637 A | 4/1989 | Dormandy, Jr. et al. |
| 4,832,055 A | 5/1989 | Palestrant |
| 4,932,419 A | 6/1990 | de Toledo |
| 4,944,746 A | 7/1990 | Iwata et al. |
| 4,957,501 A | 9/1990 | Lahille et al. |
| 4,990,155 A | 2/1991 | Wilkoff |
| 4,994,069 A | 2/1991 | Ritchart et al. |
| 5,002,556 A | 3/1991 | Ishida et al. |
| 5,026,377 A | 6/1991 | Burton et al. |
| 5,035,706 A | 7/1991 | Giantureo et al. |
| 5,037,427 A | 8/1991 | Harada et al. |
| 5,062,829 A | 11/1991 | Pryor et al. |
| 5,104,399 A | 4/1992 | Lazarus |
| 5,108,407 A | 4/1992 | Geremia et al. |
| 5,109,867 A | 5/1992 | Twyford, Jr. |
| 5,133,731 A | 7/1992 | Butler et al. |
| 5,133,732 A | 7/1992 | Wiktor |
| 5,147,370 A | 9/1992 | McNamara et al. |
| 5,167,624 A | 12/1992 | Butler et al. |
| 5,181,921 A | 1/1993 | Makita et al. |
| 5,192,301 A | 3/1993 | Kamiya et al. |
| 5,211,658 A | 5/1993 | Clouse |
| 5,222,970 A | 6/1993 | Reeves |
| 5,224,953 A | 7/1993 | Morgentaler |
| 5,226,911 A | 7/1993 | Chee et al. |
| 5,234,437 A | 8/1993 | Sepetka |
| 5,250,071 A | 10/1993 | Palermo |
| 5,256,146 A | 10/1993 | Ensminger et al. |
| 5,304,194 A | 4/1994 | Chee et al. |
| 5,312,415 A | 5/1994 | Palermo |
| 5,314,472 A | 5/1994 | Fontaine |
| 5,334,210 A | 8/1994 | Gianturco |
| 5,368,592 A | 11/1994 | Stern et al. |
| 5,382,259 A | 1/1995 | Phelps et al. |
| 5,382,260 A | 1/1995 | Dormandy, Jr. et al. |
| 5,382,261 A | 1/1995 | Palmaz |
| 5,397,345 A | 3/1995 | Lazarus |
| 5,417,708 A | 5/1995 | Hall et al. |
| 5,423,849 A | 6/1995 | Engelson et al. |
| 5,443,454 A | 8/1995 | Tanabe et al. |
| 5,456,693 A | 10/1995 | Conston et al. |
| 5,476,472 A | 12/1995 | Dormandy, Jr. et al. |
| 5,480,382 A | 1/1996 | Hammerslag et al. |
| 5,498,227 A | 3/1996 | Mawad |
| 5,507,769 A | 4/1996 | Marin et al. |
| 5,522,822 A | 6/1996 | Phelps et al. |
| 5,522,836 A | 6/1996 | Palermo |
| 5,536,274 A | 7/1996 | Neuss |
| 5,549,624 A | 8/1996 | Mirigian et al. |
| 5,556,426 A | 9/1996 | Popadiuk et al. |
| 5,562,698 A | 10/1996 | Parker |
| 5,569,245 A | 10/1996 | Guglielmi et al. |
| 5,573,520 A | 11/1996 | Schwartz et al. |
| 5,578,074 A | 11/1996 | Mirigian |
| 5,601,600 A | 2/1997 | Ton |
| 5,626,599 A | 5/1997 | Bourne et al. |
| 5,634,928 A | 6/1997 | Fischell et al. |
| 5,639,277 A | 6/1997 | Mariant et al. |
| 5,643,254 A | 7/1997 | Scheldrup et al. |
| 5,645,564 A | 7/1997 | Northrup et al. |
| 5,649,949 A | 7/1997 | Wallace et al. |
| 5,662,700 A | 9/1997 | Lazarus |
| 5,669,905 A | 9/1997 | Scheldrup et al. |
| 5,669,931 A | 9/1997 | Kupiecki et al. |
| 5,690,666 A | 11/1997 | Berenstein et al. |
| 5,690,667 A | 11/1997 | Gia |
| 5,690,671 A | 11/1997 | McGurk et al. |
| 5,693,067 A | 12/1997 | Purdy |
| 5,695,517 A | 12/1997 | Marin et al. |
| 5,700,258 A | 12/1997 | Mirigian et al. |
| 5,702,361 A | 12/1997 | Evans et al. |
| 5,718,711 A | 2/1998 | Berenstein et al. |
| 5,725,534 A | 3/1998 | Rasmussen |
| 5,725,546 A | 3/1998 | Samson |
| 5,725,552 A | 3/1998 | Kotula et al. |
| 5,733,329 A | 3/1998 | Wallace et al. |
| 5,743,905 A | 4/1998 | Eder et al. |
| 5,746,734 A | 5/1998 | Dormandy, Jr. et al. |
| 5,746,769 A | 5/1998 | Ton et al. |
| 5,749,894 A | 5/1998 | Engelson |
| 5,749,918 A | 5/1998 | Hogendijk et al. |
| 5,759,161 A | 6/1998 | Ogawa et al. |
| 5,797,953 A | 8/1998 | Tekulve |
| 5,800,426 A | 9/1998 | Taki et al. |
| 5,800,453 A | 9/1998 | Gia |
| 5,800,454 A | 9/1998 | Jacobsen et al. |
| 5,800,455 A | 9/1998 | Palermo et al. |
| 5,814,062 A | 9/1998 | Sepetka et al. |
| 5,830,230 A | 11/1998 | Berryman et al. |
| 5,833,705 A | 11/1998 | Ken et al. |
| 5,843,118 A | 12/1998 | Sepetka et al. |
| 5,846,210 A | 12/1998 | Ogawa et al. |
| 5,891,058 A | 4/1999 | Taki et al. |
| 5,891,155 A | 4/1999 | Irie |
| 5,891,192 A | 4/1999 | Murayama et al. |
| 5,895,410 A | 4/1999 | Forber et al. |
| 5,895,411 A | 4/1999 | Irie |
| 5,911,737 A | 6/1999 | Lee et al. |
| 5,925,059 A | 7/1999 | Palermo et al. |
| 5,925,060 A | 7/1999 | Forber |
| 5,925,062 A | 7/1999 | Purdy |
| 5,935,148 A | 8/1999 | Villar et al. |
| 5,941,249 A | 8/1999 | Maynard |
| 5,944,733 A | 8/1999 | Engelson |
| 5,964,797 A | 10/1999 | Ho |
| 5,972,019 A | 10/1999 | Engelson et al. |
| 5,976,131 A | 11/1999 | Guglielmi et al. |
| 5,976,152 A | 11/1999 | Regan et al. |
| 5,976,162 A | 11/1999 | Doan et al. |
| 5,980,514 A | 11/1999 | Kupiecki et al. |
| 5,980,550 A | 11/1999 | Eder et al. |
| 5,980,554 A | 11/1999 | Lenker et al. |
| 5,984,944 A | 11/1999 | Forber |
| 5,989,242 A | 11/1999 | Saadat et al. |
| 6,001,092 A | 12/1999 | Mirigian et al. |
| 6,004,338 A | 12/1999 | Ken et al. |
| 6,015,424 A | 1/2000 | Rosenbluth et al. |
| 6,017,364 A | 1/2000 | Lazarus |
| 6,017,977 A | 1/2000 | Evans et al. |
| 6,019,757 A | 2/2000 | Scheldrup |
| 6,019,779 A | 2/2000 | Thorud et al. |
| 6,022,369 A | 2/2000 | Jacobsen et al. |
| 6,024,754 A | 2/2000 | Engelson |
| 6,024,765 A | 2/2000 | Wallace et al. |
| 6,030,413 A | 2/2000 | Lazarus |
| 6,033,423 A | 3/2000 | Ken et al. |
| 6,039,749 A | 3/2000 | Marin et al. |
| 6,056,770 A | 5/2000 | Epstein et al. |
| 6,059,779 A | 5/2000 | Mills |
| 6,059,815 A | 5/2000 | Lee et al. |
| 6,063,104 A | 5/2000 | Villar et al. |
| 6,068,644 A | 5/2000 | Lulo et al. |
| 6,074,407 A | 6/2000 | Levine et al. |
| D427,680 S | 7/2000 | Mariant et al. |
| 6,086,577 A | 7/2000 | Ken et al. |
| 6,093,199 A | 7/2000 | Brown et al. |
| 6,096,034 A | 8/2000 | Kupiecki et al. |
| 6,096,546 A | 8/2000 | Raskin |
| 6,102,917 A | 8/2000 | Maitland et al. |
| 6,102,933 A | 8/2000 | Lee et al. |
| 6,113,622 A | 9/2000 | Hieshima |
| 6,117,142 A | 9/2000 | Goodson et al. |
| 6,117,157 A | 9/2000 | Tekulve |
| 6,126,672 A | 10/2000 | Berryman et al. |
| 6,143,007 A | 11/2000 | Mariant et al. |
| 6,149,664 A | 11/2000 | Kurz |
| 6,149,681 A | 11/2000 | Houser et al. |
| 6,159,206 A | 12/2000 | Ogawa |
| 6,165,193 A | 12/2000 | Greene, Jr. et al. |
| 6,165,198 A | 12/2000 | McGurk et al. |
| 6,168,570 B1 | 1/2001 | Ferrera |
| 6,168,592 B1 | 1/2001 | Kupiecki et al. |
| 6,168,610 B1 | 1/2001 | Marin et al. |

(56) References Cited

U.S. PATENT DOCUMENTS

| | | |
|---|---|---|
| 6,168,615 B1 | 1/2001 | Ken et al. |
| 6,168,622 B1 | 1/2001 | Mazzocchi |
| 6,183,491 B1 | 2/2001 | Lulo |
| 6,183,495 B1 | 2/2001 | Lenker et al. |
| 6,187,024 B1 | 2/2001 | Boock et al. |
| 6,187,027 B1 | 2/2001 | Mariant et al. |
| 6,193,708 B1 | 2/2001 | Ken et al. |
| 6,193,728 B1 | 2/2001 | Ken et al. |
| RE37,117 E | 3/2001 | Palermo |
| 6,202,261 B1 | 3/2001 | Moore et al. |
| 6,203,547 B1 | 3/2001 | Nguyen et al. |
| 6,221,086 B1 | 4/2001 | Forber |
| 6,224,610 B1 | 5/2001 | Ferrera |
| 6,231,573 B1 | 5/2001 | Amor et al. |
| 6,231,590 B1 | 5/2001 | Slaikeu et al. |
| 6,231,597 B1 | 5/2001 | Deem et al. |
| 6,238,403 B1 | 5/2001 | Greene, Jr. et al. |
| 6,238,415 B1 | 5/2001 | Sepetka et al. |
| 6,241,691 B1 | 6/2001 | Ferrera et al. |
| 6,254,592 B1 | 7/2001 | Samson et al. |
| 6,270,495 B1 | 8/2001 | Palermo |
| 6,277,125 B1 | 8/2001 | Barry et al. |
| 6,277,126 B1 | 8/2001 | Barry et al. |
| 6,281,263 B1 | 8/2001 | Evans et al. |
| 6,287,315 B1 | 9/2001 | Wijeratne et al. |
| 6,287,318 B1 | 9/2001 | Villar et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,299,627 B1 | 10/2001 | Eder et al. |
| 6,306,153 B1 | 10/2001 | Kurz et al. |
| 6,312,405 B1 | 11/2001 | Meyer et al. |
| 6,312,421 B1 | 11/2001 | Boock |
| 6,315,709 B1 | 11/2001 | Garibaldi et al. |
| 6,328,750 B1 | 12/2001 | Berry et al. |
| 6,331,184 B1 | 12/2001 | Abrams |
| 6,335,384 B1 | 1/2002 | Evans et al. |
| 6,338,736 B1 | 1/2002 | Boosfeld et al. |
| 6,344,048 B1 | 2/2002 | Chin et al. |
| 6,346,091 B1 | 2/2002 | Jacobsen et al. |
| 6,346,117 B1 | 2/2002 | Greenhalgh |
| 6,348,041 B1 | 2/2002 | Klint |
| 6,361,547 B1 | 3/2002 | Hieshima |
| 6,364,823 B1 | 4/2002 | Garibaldi et al. |
| 6,368,338 B1 | 4/2002 | Konya et al. |
| 6,375,606 B1 | 4/2002 | Garibaldi et al. |
| 6,375,628 B1 | 4/2002 | Zadno-Azizi et al. |
| 6,375,668 B1 | 4/2002 | Gifford et al. |
| 6,375,669 B1 | 4/2002 | Rosenbluth et al. |
| 6,379,329 B1 | 4/2002 | Naglreiter et al. |
| 6,379,374 B1 | 4/2002 | Hieshima et al. |
| 6,383,146 B1 | 5/2002 | Klint |
| 6,383,205 B1 | 5/2002 | Samson et al. |
| 6,409,721 B1 | 6/2002 | Wheelock et al. |
| 6,416,535 B1 | 7/2002 | Lazarus |
| 6,416,541 B2 | 7/2002 | Denardo |
| 6,423,085 B1 | 7/2002 | Murayama et al. |
| 6,425,914 B1 | 7/2002 | Wallace et al. |
| 6,428,557 B1 | 8/2002 | Hilaire |
| 6,428,558 B1 | 8/2002 | Jones et al. |
| 6,454,780 B1 | 9/2002 | Wallace |
| 6,458,119 B1 | 10/2002 | Berenstein et al. |
| 6,458,127 B1 | 10/2002 | Truckai et al. |
| 6,458,137 B1 | 10/2002 | Klint |
| 6,464,699 B1 | 10/2002 | Swanson |
| 6,475,169 B2 | 11/2002 | Ferrera |
| 6,475,227 B2 | 11/2002 | Burke et al. |
| 6,494,884 B2 | 12/2002 | Gifford, III et al. |
| 6,500,149 B2 | 12/2002 | Gandhi et al. |
| 6,500,190 B2 | 12/2002 | Greene, Jr. et al. |
| 6,506,204 B2 | 1/2003 | Mazzocchi |
| 6,514,264 B1 | 2/2003 | Naglreiter |
| 6,530,934 B1 | 3/2003 | Jacobsen et al. |
| 6,533,801 B2 | 3/2003 | Wallace et al. |
| 6,537,293 B1 | 3/2003 | Berryman et al. |
| 6,540,657 B2 | 4/2003 | Cross, III et al. |
| 6,544,163 B2 | 4/2003 | Wallace et al. |
| 6,544,225 B1 | 4/2003 | Lulo et al. |
| 6,544,268 B1 | 4/2003 | Lazarus |
| 6,544,275 B1 | 4/2003 | Teoh |
| 6,547,804 B2 | 4/2003 | Porter et al. |
| 6,551,305 B2 | 4/2003 | Ferrera et al. |
| 6,554,849 B1 | 4/2003 | Jones et al. |
| 6,569,179 B2 | 5/2003 | Teoh et al. |
| 6,572,628 B2 | 6/2003 | Dominguez et al. |
| 6,575,994 B1 | 6/2003 | Marin et al. |
| 6,585,748 B1 | 7/2003 | Jeffree |
| 6,589,227 B2 | 7/2003 | Klint |
| 6,589,230 B2 | 7/2003 | Gia et al. |
| 6,589,236 B2 | 7/2003 | Wheelock et al. |
| 6,589,265 B1 | 7/2003 | Palmer et al. |
| 6,592,605 B2 | 7/2003 | Lenker et al. |
| 6,602,261 B2 | 8/2003 | Greene, Jr. et al. |
| 6,602,269 B2 | 8/2003 | Wallace et al. |
| 6,603,994 B2 | 8/2003 | Wallace et al. |
| 6,607,539 B1 | 8/2003 | Hayashi et al. |
| 6,610,085 B1 | 8/2003 | Lazarus |
| 6,613,074 B1 | 9/2003 | Mitelberg et al. |
| 6,623,493 B2 | 9/2003 | Wallace et al. |
| 6,632,241 B1 | 10/2003 | Hancock et al. |
| 6,635,068 B1 | 10/2003 | Dubrul et al. |
| 6,638,293 B1 | 10/2003 | Makower et al. |
| 6,656,173 B1 | 12/2003 | Palermo |
| 6,656,218 B1 | 12/2003 | Denardo et al. |
| 6,656,351 B2 | 12/2003 | Boyle |
| 6,660,020 B2 | 12/2003 | Wallace et al. |
| 6,663,607 B2 | 12/2003 | Slaikeu et al. |
| 6,685,653 B2 | 2/2004 | Ehr et al. |
| 6,685,696 B2 * | 2/2004 | Fleischhacker et al. ...... 604/526 |
| 6,689,141 B2 | 2/2004 | Ferrera et al. |
| 6,692,510 B2 | 2/2004 | West |
| 6,702,844 B1 | 3/2004 | Lazarus |
| 6,716,238 B2 | 4/2004 | Elliott |
| 6,723,112 B2 | 4/2004 | Ho et al. |
| 6,743,236 B2 | 6/2004 | Barry et al. |
| 6,743,251 B1 | 6/2004 | Eder |
| 6,767,358 B2 | 7/2004 | Leonhardt et al. |
| 6,811,561 B2 | 11/2004 | Diaz et al. |
| 6,814,748 B1 | 11/2004 | Baker et al. |
| 6,835,185 B2 | 12/2004 | Ramzipoor et al. |
| 6,849,081 B2 | 2/2005 | Sepetka et al. |
| 6,852,116 B2 | 2/2005 | Leonhardt et al. |
| 6,853,418 B2 | 2/2005 | Suzuki et al. |
| 6,855,153 B2 | 2/2005 | Saadat |
| 6,855,155 B2 | 2/2005 | Denardo et al. |
| 6,860,893 B2 | 3/2005 | Wallace et al. |
| 6,860,901 B1 | 3/2005 | Baker et al. |
| 6,872,218 B2 | 3/2005 | Ferrera et al. |
| 6,878,163 B2 | 4/2005 | Denardo et al. |
| 6,905,503 B2 | 6/2005 | Gifford, III et al. |
| 6,913,618 B2 | 7/2005 | Denardo et al. |
| 6,945,956 B2 | 9/2005 | Waldhauser et al. |
| 6,958,061 B2 | 10/2005 | Truckai et al. |
| 6,958,068 B2 | 10/2005 | Hieshima |
| 6,984,240 B1 | 1/2006 | Ken et al. |
| 6,994,711 B2 | 2/2006 | Hieshima et al. |
| 7,014,645 B2 | 3/2006 | Greene, Jr. et al. |
| 7,029,486 B2 | 4/2006 | Schaefer et al. |
| 7,029,487 B2 | 4/2006 | Greene, Jr. et al. |
| 7,033,374 B2 | 4/2006 | Schaefer et al. |
| 7,058,456 B2 | 6/2006 | Pierce |
| 7,060,083 B2 | 6/2006 | Gerberding |
| 7,070,607 B2 | 7/2006 | Murayama et al. |
| 7,169,161 B2 | 1/2007 | Bonnette et al. |
| 7,182,774 B2 | 2/2007 | Barry et al. |
| 7,331,973 B2 | 2/2008 | Gesswein et al. |
| 7,344,558 B2 | 3/2008 | Lorenzo et al. |
| 7,410,482 B2 | 8/2008 | Murphy et al. |
| 7,473,266 B2 | 1/2009 | Glaser |
| 7,485,122 B2 | 2/2009 | Teoh |
| 7,485,317 B1 | 2/2009 | Murayama et al. |
| RE41,029 E | 12/2009 | Guglielmi et al. |
| 7,691,124 B2 | 4/2010 | Balgobin |
| 7,708,755 B2 | 5/2010 | Davis, III et al. |

(56) References Cited

U.S. PATENT DOCUMENTS

| | | |
|---|---|---|
| 7,722,636 B2 | 5/2010 | Farnan |
| 7,722,637 B2 | 5/2010 | Barry et al. |
| 7,766,933 B2 | 8/2010 | Davis, III et al. |
| 7,811,305 B2 | 10/2010 | Balgobin et al. |
| 7,841,994 B2 | 11/2010 | Skujins et al. |
| 7,883,526 B2 | 2/2011 | Jones et al. |
| 7,896,899 B2 | 3/2011 | Patterson et al. |
| 7,901,444 B2 | 3/2011 | Slazas |
| 7,901,704 B2 | 3/2011 | Richard |
| 7,918,872 B2 | 4/2011 | Mitelberg et al. |
| 7,938,845 B2 | 5/2011 | Aganon et al. |
| 7,955,272 B2 | 6/2011 | Rooney et al. |
| 8,002,789 B2 | 8/2011 | Ramzipoor et al. |
| 8,007,509 B2 | 8/2011 | Buiser et al. |
| 2002/0052613 A1 | 5/2002 | Ferrera et al. |
| 2002/0065529 A1 | 5/2002 | Laurent et al. |
| 2002/0072712 A1 | 6/2002 | Nool et al. |
| 2002/0072791 A1 | 6/2002 | Eder et al. |
| 2002/0082620 A1 | 6/2002 | Lee |
| 2002/0087184 A1 | 7/2002 | Eder et al. |
| 2002/0120297 A1 | 8/2002 | Shadduck |
| 2002/0128671 A1 | 9/2002 | Wallace et al. |
| 2002/0138095 A1 | 9/2002 | Mazzocchi et al. |
| 2002/0143349 A1 | 10/2002 | Gifford et al. |
| 2002/0169473 A1 | 11/2002 | Sepetka et al. |
| 2003/0045901 A1 | 3/2003 | Opolski |
| 2003/0083676 A1 | 5/2003 | Wallace |
| 2003/0130689 A1 | 7/2003 | Wallace et al. |
| 2003/0169473 A1 | 9/2003 | Cotter et al. |
| 2003/0176857 A1 | 9/2003 | Lee |
| 2003/0181927 A1 | 9/2003 | Wallace |
| 2003/0216772 A1 | 11/2003 | Konya et al. |
| 2004/0002731 A1 | 1/2004 | Aganon et al. |
| 2004/0002732 A1 | 1/2004 | Teoh et al. |
| 2004/0006354 A1 | 1/2004 | Schaefer et al. |
| 2004/0006362 A1 | 1/2004 | Schaefer et al. |
| 2004/0006363 A1 | 1/2004 | Schaefer |
| 2004/0024394 A1 | 2/2004 | Wallace et al. |
| 2004/0034363 A1 | 2/2004 | Wilson et al. |
| 2004/0034378 A1 | 2/2004 | Monstadt et al. |
| 2004/0078050 A1 | 4/2004 | Monstadt et al. |
| 2004/0082879 A1 | 4/2004 | Klint |
| 2004/0181256 A1 | 9/2004 | Glaser |
| 2004/0193178 A1 | 9/2004 | Nikolchev |
| 2004/0193206 A1 | 9/2004 | Gerberding et al. |
| 2004/0220563 A1 | 11/2004 | Eder |
| 2004/0220585 A1 | 11/2004 | Nikolchev |
| 2004/0225279 A1 | 11/2004 | Raymond |
| 2004/0236344 A1 | 11/2004 | Monstadt et al. |
| 2004/0260384 A1 | 12/2004 | Allen |
| 2005/0021023 A1 | 1/2005 | Guglielmi et al. |
| 2005/0021074 A1 | 1/2005 | Elliott |
| 2005/0079196 A1 | 4/2005 | Henkes et al. |
| 2005/0171572 A1 | 8/2005 | Martinez |
| 2005/0177185 A1 | 8/2005 | Becker et al. |
| 2005/0187564 A1 | 8/2005 | Jayaraman |
| 2006/0025801 A1 | 2/2006 | Lulo et al. |
| 2006/0025802 A1 | 2/2006 | Sowers |
| 2006/0036281 A1 | 2/2006 | Patterson et al. |
| 2006/0079926 A1 | 4/2006 | Desai et al. |
| 2006/0106417 A1 | 5/2006 | Tessmer et al. |
| 2006/0116711 A1 | 6/2006 | Elliott et al. |
| 2006/0116714 A1 | 6/2006 | Sepetka et al. |
| 2006/0200190 A1 | 9/2006 | Lorenzo et al. |
| 2006/0276824 A1 | 12/2006 | Mitelberg et al. |
| 2007/0055302 A1 | 3/2007 | Henry et al. |
| 2007/0083226 A1 | 4/2007 | Buiser et al. |
| 2007/0142893 A1 | 6/2007 | Buiser et al. |
| 2007/0150045 A1 | 6/2007 | Ferrera |
| 2007/0173757 A1 | 7/2007 | Levine et al. |
| 2007/0185524 A1 | 8/2007 | Diaz et al. |
| 2007/0225738 A1 | 9/2007 | Pal |
| 2007/0239193 A1 | 10/2007 | Simon et al. |
| 2007/0239199 A1 | 10/2007 | Jayaraman |
| 2007/0282425 A1 | 12/2007 | Kleine et al. |
| 2007/0299461 A1 | 12/2007 | Elliott |
| 2008/0046092 A1 | 2/2008 | Davis et al. |
| 2008/0046093 A1 | 2/2008 | Davis et al. |
| 2008/0097462 A1 | 4/2008 | Mitelberg et al. |
| 2008/0103585 A1 | 5/2008 | Monstadt et al. |
| 2008/0125855 A1 | 5/2008 | Henkes et al. |
| 2008/0228215 A1 | 9/2008 | Strauss et al. |
| 2008/0300616 A1 | 12/2008 | Que et al. |
| 2008/0306504 A1 | 12/2008 | Win et al. |
| 2008/0319532 A1 | 12/2008 | Monstadt et al. |
| 2009/0048631 A1* | 2/2009 | Bhatnagar et al. ............ 606/246 |
| 2009/0069836 A1 | 3/2009 | Labdag et al. |
| 2009/0149864 A1 | 6/2009 | Porter |
| 2009/0182268 A1 | 7/2009 | Thielen et al. |
| 2009/0254169 A1 | 10/2009 | Spenser et al. |
| 2009/0270877 A1 | 10/2009 | Johnson et al. |
| 2009/0312748 A1 | 12/2009 | Johnson et al. |
| 2010/0004673 A1 | 1/2010 | Denison et al. |
| 2010/0004675 A1 | 1/2010 | Wilson et al. |
| 2010/0030200 A1 | 2/2010 | Strauss et al. |
| 2010/0030319 A1 | 2/2010 | Weber |
| 2010/0076479 A1 | 3/2010 | Monstadt |
| 2010/0174269 A1 | 7/2010 | Tompkins et al. |
| 2011/0022003 A1 | 1/2011 | Tekulve |
| 2011/0098814 A1 | 4/2011 | Monstadt et al. |
| 2011/0118777 A1 | 5/2011 | Patterson et al. |
| 2011/0172700 A1 | 7/2011 | Bose et al. |
| 2011/0184454 A1 | 7/2011 | Barry et al. |
| 2011/0213406 A1 | 9/2011 | Aganon et al. |
| 2011/0245861 A1 | 10/2011 | Chen et al. |
| 2011/0313447 A1 | 12/2011 | Strauss et al. |
| 2013/0253572 A1 | 9/2013 | Molaei et al. |

FOREIGN PATENT DOCUMENTS

| | | |
|---|---|---|
| CA | 2265062 | 9/1999 |
| CA | 2265062 A1 | 9/1999 |
| CN | 1668250 A | 9/2005 |
| DE | 4445715 | 6/1996 |
| DE | 69627243 | 1/1997 |
| DE | 19547617 | 9/1997 |
| DE | 19607451 | 9/1997 |
| DE | 19610333 | 9/1997 |
| DE | 19647280 | 5/2001 |
| DE | 19952387 | 5/2001 |
| DE | 10010840 | 9/2001 |
| DE | 10118017 | 10/2002 |
| DE | 10155191 | 5/2003 |
| EP | 707830 | 4/1996 |
| EP | 711 532 | 5/1996 |
| EP | 717969 A2 | 6/1996 |
| EP | 720838 | 7/1996 |
| EP | 765636 A3 | 4/1997 |
| EP | 0792623 | 9/1997 |
| EP | 0792623 A1 | 9/1997 |
| EP | 820 726 | 1/1998 |
| EP | 830 873 | 3/1998 |
| EP | 829236 | 3/1998 |
| EP | 853 955 | 7/1998 |
| EP | 865 773 | 9/1998 |
| EP | 882 428 | 9/1998 |
| EP | 904 737 | 3/1999 |
| EP | 914 807 | 5/1999 |
| EP | 941 700 | 9/1999 |
| EP | 941 701 | 9/1999 |
| EP | 992 220 | 4/2000 |
| EP | 1005837 A2 | 6/2000 |
| EP | 1 120 088 | 8/2001 |
| EP | 1 125 553 | 8/2001 |
| EP | 1 129 666 | 9/2001 |
| EP | 1 142 535 | 10/2001 |
| EP | 1 169 969 | 1/2002 |
| EP | 1 188 413 | 3/2002 |
| EP | 1 188 414 | 3/2002 |
| EP | 1295563 | 3/2003 |
| EP | 1 312 312 | 5/2003 |
| EP | 1 316 293 | 6/2003 |
| EP | 1 358 850 | 11/2003 |
| EP | 1374801 | 1/2004 |

(56) References Cited

FOREIGN PATENT DOCUMENTS

| | | |
|---|---|---|
| EP | 1 669 032 | 6/2006 |
| EP | 1738698 A2 | 1/2007 |
| EP | 832 607 | 4/2008 |
| EP | 2260800 A2 | 12/2010 |
| EP | 2292147 | 3/2011 |
| JP | 6-246004 | 9/1994 |
| JP | 7-155331 | 6/1995 |
| JP | 7-265431 | 10/1995 |
| JP | 7-284534 | 10/1995 |
| JP | 9-168541 A | 6/1997 |
| JP | 10-201766 | 8/1998 |
| JP | 11-47138 | 2/1999 |
| JP | 11-76249 | 3/1999 |
| JP | 2001-513389 A | 9/2001 |
| JP | 2002-523172 A | 7/2002 |
| JP | 2004-500929 A | 1/2004 |
| JP | 2006-051349 A | 2/2006 |
| JP | 2008-525113 A | 7/2008 |
| KR | 10-2010-0107255 | 10/2010 |
| KR | 10-20100107255 | 10/2010 |
| KR | 10-1014547 | 2/2011 |
| WO | WO-88/03817 | 6/1988 |
| WO | WO-89/06984 | 8/1989 |
| WO | WO-90/12616 | 11/1990 |
| WO | WO-91/13592 | 9/1991 |
| WO | WO-92/14408 | 9/1992 |
| WO | WO-92/21400 | 12/1992 |
| WO | WO-93/11719 | 6/1993 |
| WO | WO-93/16650 | 9/1993 |
| WO | WO-94/06502 A2 | 3/1994 |
| WO | WO-94/06503 | 3/1994 |
| WO | WO-94/10936 | 5/1994 |
| WO | WO-94/11051 | 5/1994 |
| WO | WO-94/26175 | 11/1994 |
| WO | WO-95/12367 | 5/1995 |
| WO | WO-96/18343 | 6/1996 |
| WO | WO-96/32153 | 10/1996 |
| WO | WO-96/39950 | 12/1996 |
| WO | WO-97/27888 | 8/1997 |
| WO | WO-97/42881 | 11/1997 |
| WO | WO-98/09570 | 3/1998 |
| WO | WO-98/17183 | 4/1998 |
| WO | WO-98/33452 | 8/1998 |
| WO | WO-98/34546 | 8/1998 |
| WO | WO-98/39048 A2 | 9/1998 |
| WO | WO-98/58590 | 12/1998 |
| WO | WO-99/02094 | 1/1999 |
| WO | WO-99/05977 | 2/1999 |
| WO | WO-99/07292 | 2/1999 |
| WO | WO-99/09893 | 3/1999 |
| WO | WO-99/32037 | 7/1999 |
| WO | WO-99/42038 | 8/1999 |
| WO | WO-99/44538 | 9/1999 |
| WO | WO-99/49812 | 10/1999 |
| WO | WO-99/56636 | 11/1999 |
| WO | WO-00/13593 | 3/2000 |
| WO | WO-00/25680 | 5/2000 |
| WO | WO-00/44306 | 8/2000 |
| WO | WO-00/72781 A2 | 12/2000 |
| WO | WO-01/32085 | 5/2001 |
| WO | WO-01/45571 A1 | 6/2001 |
| WO | WO-01/56500 A2 | 8/2001 |
| WO | WO-01/58365 | 8/2001 |
| WO | WO-01/58382 A2 | 8/2001 |
| WO | WO-01/087184 | 11/2001 |
| WO | WO-01/93937 A2 | 12/2001 |
| WO | WO-02/02018 | 1/2002 |
| WO | WO-02/13705 | 2/2002 |
| WO | WO-02/13706 A2 | 2/2002 |
| WO | WO-02/032496 | 4/2002 |
| WO | WO-02/39911 A2 | 5/2002 |
| WO | WO-02/41753 A2 | 5/2002 |
| WO | WO-02/45596 A2 | 6/2002 |
| WO | WO-02/054943 A2 | 7/2002 |
| WO | WO-02/054980 A2 | 7/2002 |
| WO | WO-02/072168 A2 | 9/2002 |
| WO | WO-02/087449 | 11/2002 |
| WO | WO-02/087651 | 11/2002 |
| WO | WO-02/089676 A2 | 11/2002 |
| WO | WO-02/096273 A2 | 12/2002 |
| WO | WO-02/096301 | 12/2002 |
| WO | WO-03/001970 A2 | 1/2003 |
| WO | WO-03/007823 | 1/2003 |
| WO | WO-03/034927 | 5/2003 |
| WO | WO-03/039624 A2 | 5/2003 |
| WO | WO-03/053257 | 7/2003 |
| WO | WO-03/053281 | 7/2003 |
| WO | WO-03/073914 A2 | 9/2003 |
| WO | WO-03/077776 | 9/2003 |
| WO | WO-03/077984 | 9/2003 |
| WO | WO-03/082128 | 10/2003 |
| WO | WO-03/086240 | 10/2003 |
| WO | WO-03/092547 | 11/2003 |
| WO | WO-03/099370 | 12/2003 |
| WO | WO-2004/008974 | 1/2004 |
| WO | WO-2004/010878 A1 | 2/2004 |
| WO | WO-2004/014239 | 2/2004 |
| WO | WO-2004/069059 | 8/2004 |
| WO | WO-2004/073529 | 9/2004 |
| WO | WO-2005/065556 | 7/2005 |
| WO | WO 2005/065556 A1 | 7/2005 |
| WO | WO-2006/058042 A2 | 6/2006 |
| WO | WO-2006/069123 | 6/2006 |
| WO | WO-2007/121405 | 10/2007 |
| WO | WO-2008/112435 | 9/2008 |
| WO | WO-2008/112436 | 9/2008 |
| WO | WO-2008/127328 | 10/2008 |
| WO | WO-2008/127328 A1 | 10/2008 |
| WO | WO-2010/092174 A2 | 8/2010 |
| WO | WO-2010/117883 | 10/2010 |
| WO | WO-2010/123821 | 10/2010 |
| WO | WO-2010/134914 | 11/2010 |
| WO | WO-2010/134914 A1 | 11/2010 |
| WO | WO-2011/030820 | 3/2011 |
| WO | WO-2011/030820 A1 | 3/2011 |
| WO | WO-2012/161953 A2 | 11/2012 |

\* cited by examiner

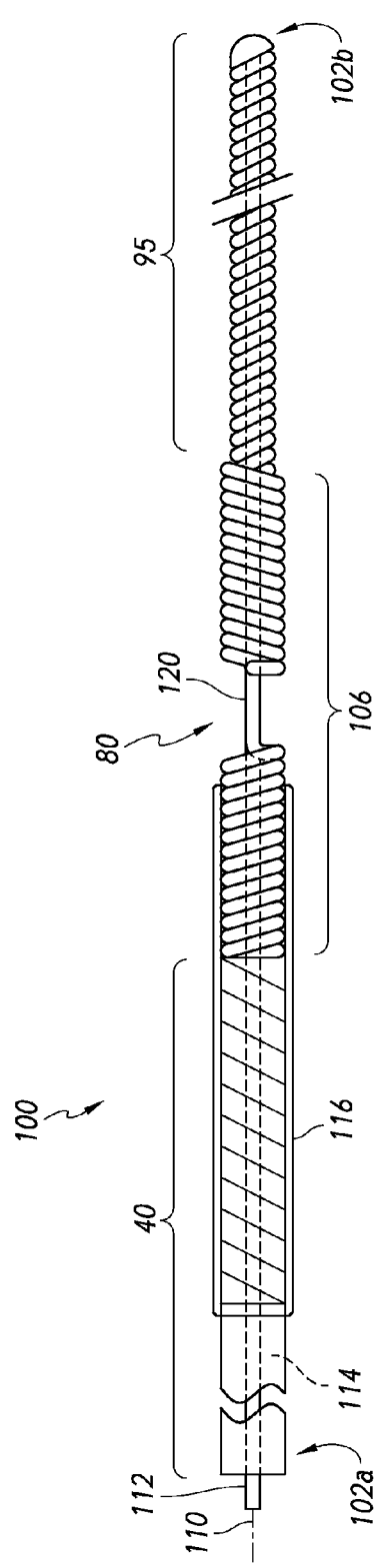
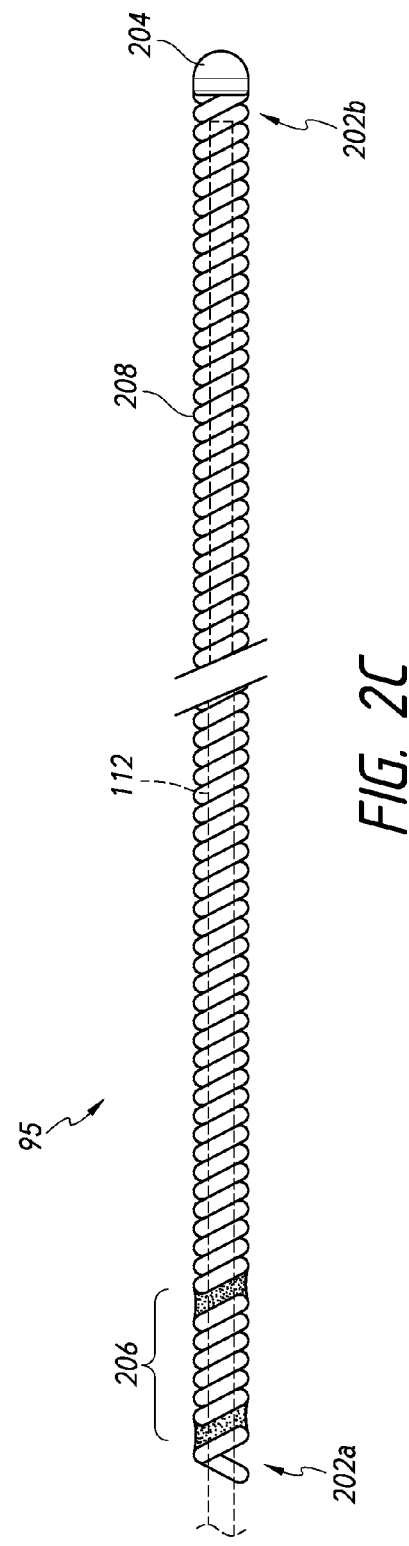
FIG. 2B
FIG. 2C

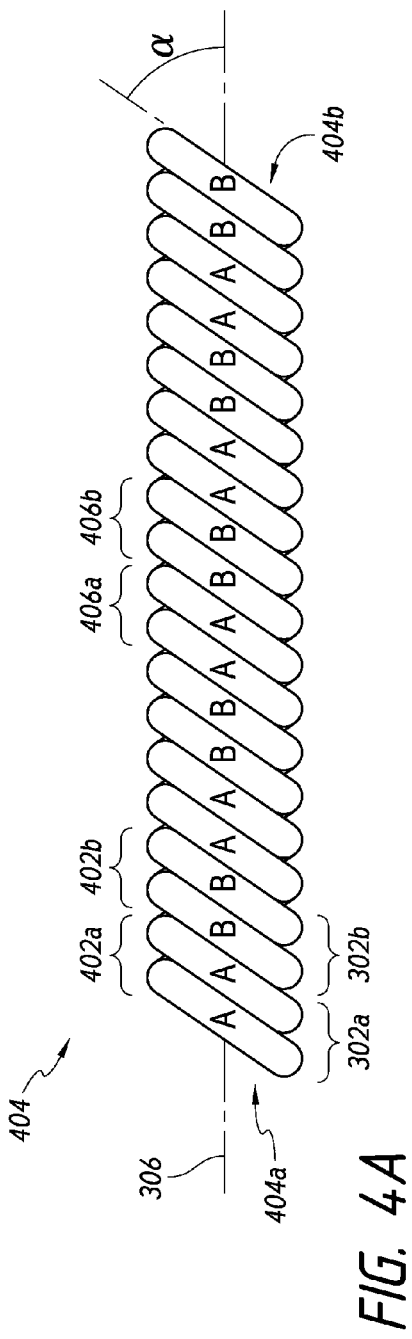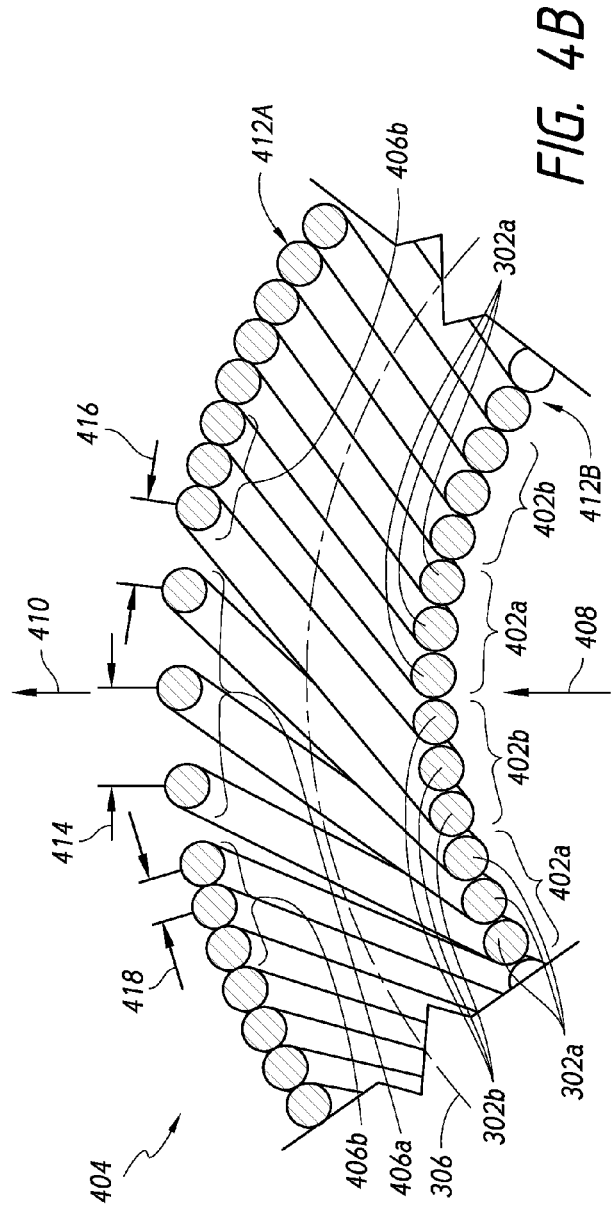

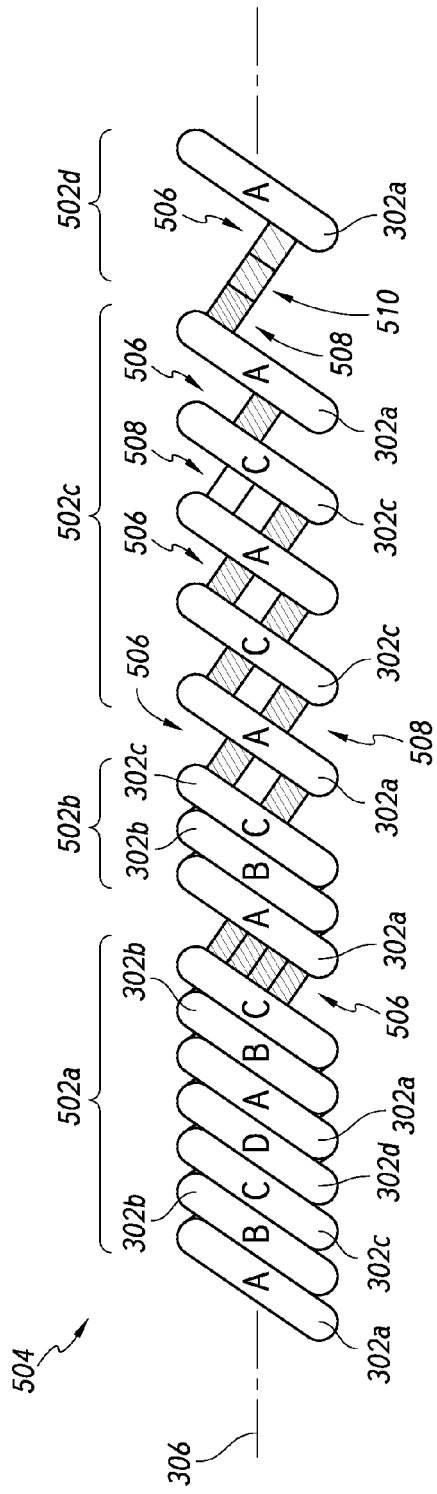
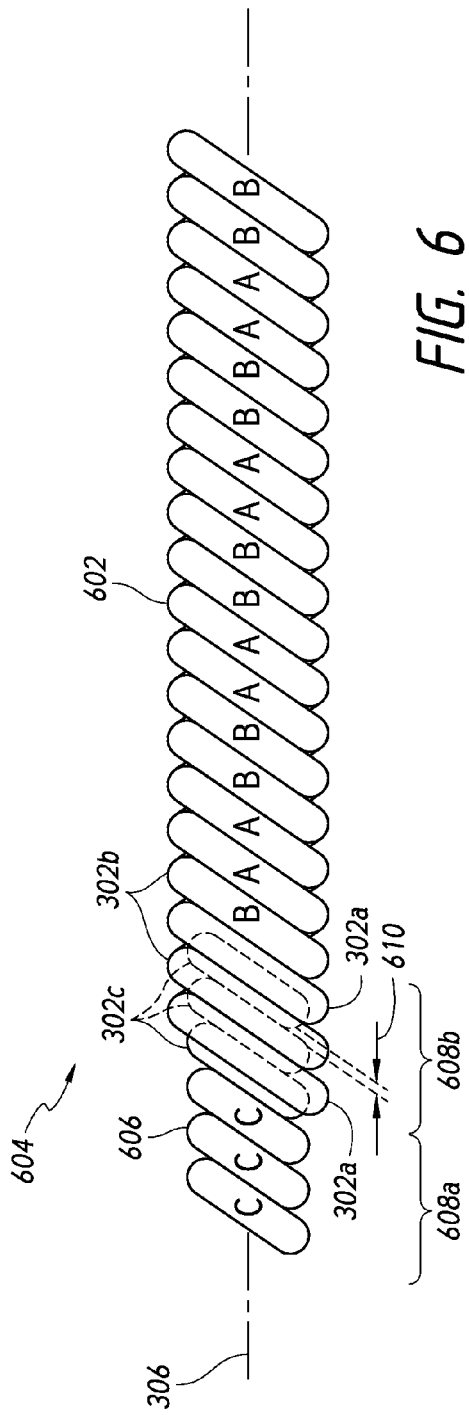
FIG. 5
FIG. 6

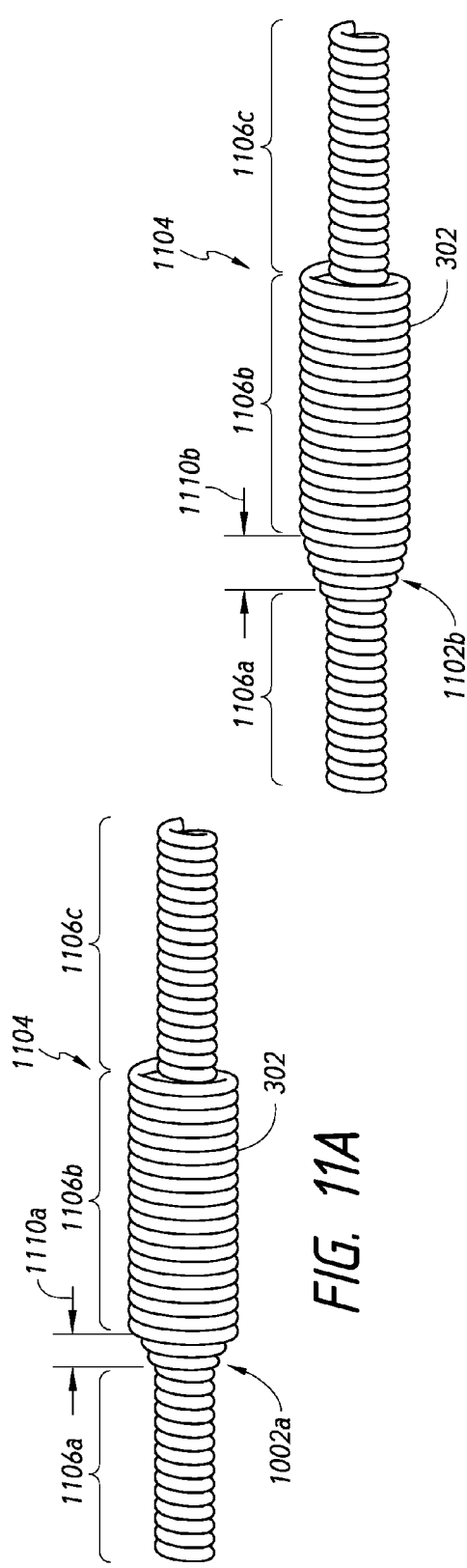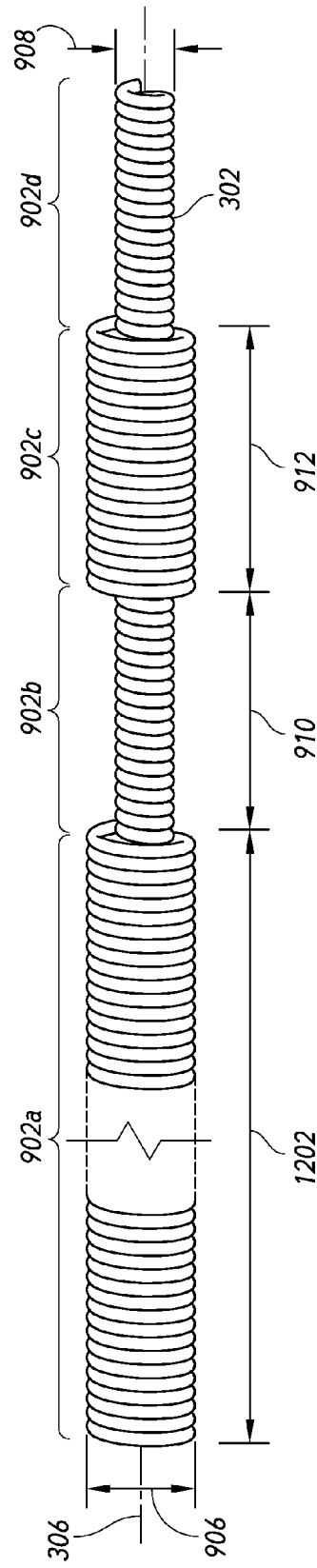
FIG. 11A
FIG. 11B
FIG. 12

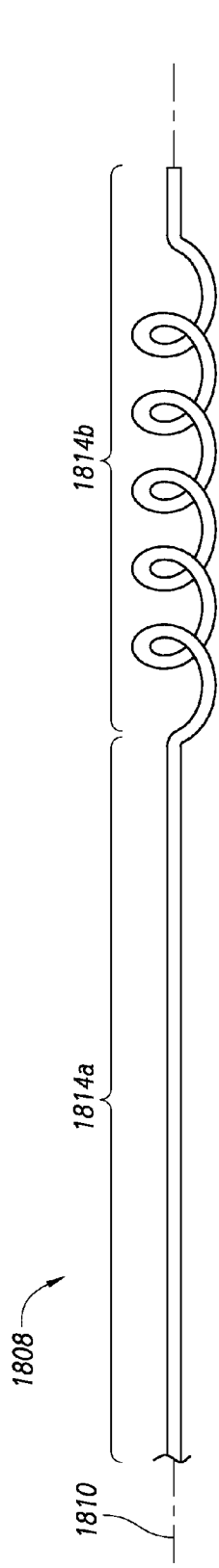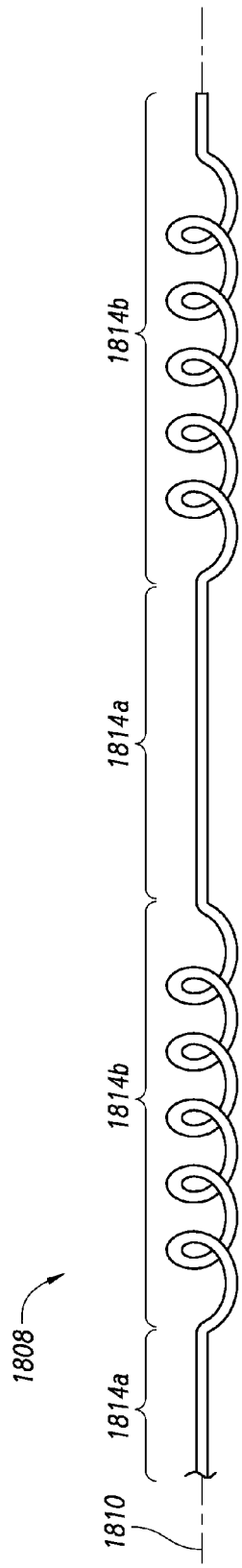

ANEURYSM TREATMENT COILS

FIELD

The subject technology generally relates to a medical implant device. More particularly, the subject technology relates to medical implant devices in the form of at least one elongated filament.

BACKGROUND

Lumens in the body, e.g., blood vessels or the gastrointestinal tract, can change in size, shape, and/or patency, and such changes can present complications or affect associated body functions. For example, the walls of the vasculature, particularly arterial walls, may develop a pathological dilatation called an aneurysm. Aneurysms are observed as a ballooning out of a wall of an artery. This is a result of the vessel wall being weakened by disease, injury or a congenital abnormality. Aneurysms have thin, weak walls, have a tendency to rupture, and are often caused or made worse by high blood pressure. Aneurysms can be found in different parts of the body; the most common being abdominal aortic aneurysms and cerebral (brain) aneurysms. The mere presence of an aneurysm is not always life threatening, but they can have serious heath consequences such as a stroke if one should rupture in the brain. Additionally, a ruptured aneurysm can also result in death.

SUMMARY

In clinical situations it is often desirable to fully or partially occlude blood vessels or portions of blood vessels for various reasons, such as the control or prevention of bleeding, the prevention of blood supply to tumors, treatment of arteriovenous malformations (AVMs), and the blocking of blood flow within an aneurysm. Embolization of blood vessels has been performed by employing certain polymer compositions, particulates, and/or scelerosing material including silicone balloons, metallic coils, PVA particles, gelatin, and the like, selectively to block blood flow in the blood vessels.

Intracranial aneurysms are abnormal blood-filled dilations of a blood vessel wall that may rupture, causing significant bleeding and damage to surrounding brain tissue or death. In some cases, intracranial aneurysms can be surgically clipped to reduce the risk of rupture by placing a metal clip around the neck of the aneurysm to cut off and prevent further blood flow to the aneurysm. Many aneurysms cannot be treated surgically because of either the location or configuration of the aneurysm or because the condition of the patient does not permit intracranial surgery.

Aneurysms may also be treated endovascularly, e.g., with embolic coils. The coils are placed in the aneurysm by extending a catheter endovascularly to the site of the aneurysm and passing single or often multiple metallic coils such as platinum, stainless steel, or tungsten coils through the catheter into the aneurysm. The coils placed within the aneurysm encourage a thrombus to form in the aneurysm which occludes the aneurysm and prevents further blood flow into the aneurysm. The treatment of intracranial aneurysms with coils isolates the aneurysm from arterial circulation, helping to guard against rupture and further growth of the aneurysm.

The subject technology is illustrated, for example, according to various aspects described below. Various examples of aspects of the subject technology are described as embodiments. These are provided as examples and do not limit the subject technology. It is noted that these embodiments may be combined in any combination.

According to various embodiments of the subject technology, a multifilar coil is disclosed and includes a first plurality of adjacent first filaments helically wound about a long axis, each of the first filaments having a substantially equal first filament lateral flexibility. The multifilar coil may also include a second plurality of adjacent second filaments, wound adjacent to the first plurality about the long axis, at least two of the second filaments having a second filament lateral flexibility, less than the first filament flexibility. A first region of the coil may have a first coil flexibility that permits bending at the first region in a first direction relative to the long axis. In one or more embodiments, the first coil flexibility is greater than a second coil flexibility that permits bending, in the first direction, of a second region of the coil that is (i) spaced apart from the first region along the long axis and (ii) sized equal to the first region.

In some embodiments, the multifilar coil may have between 6 and 50, between 8 and 40, or between 10 and 30 filaments. Except for the distalmost two filaments in the multifilar coil, each filament at its terminal distal end may be flanked by an immediately adjacent filament on each of its proximal and distal sides. In other embodiments, except for the distalmost two filaments, each filament at its terminal distal end is flanked by an immediately adjacent filament on each of its proximal and distal sides. In some embodiments, each of the plurality of second filaments has a substantially equal second filament lateral flexibility. In some embodiments, the first filament flexibility is between about 2×, about 3×, about 5×, and about 10× the second filament flexibility. In other embodiments, the first filament may be about 50×, 100×, 500×, 1000×, 2000×, or more than 2000× the second filament flexibility. In some aspects, the first filament flexibility may at least partly be determined, in the one or more first filaments, by at least one of a filament diameter, a material composition, and a heat treatment. The first coil flexibility may be more than at least one of about 2×, about 3×, about 5×, and about 10× the second coil flexibility.

In at least one embodiment, a proximal end region of the multifilar coil couples to a delivery device, and the first region is proximal to the second region thereby providing a greater flexibility proximal to the second region to provide a break point about which the coil can bend or break. In some embodiments, each of at least one of (a) the plurality of first filaments and (b) the plurality of second filaments has a distal end at a point separated, along the long axis, from distal ends of others of the first and second filaments. In one or more embodiments, one or more of first and/or second filaments comprises a ribbon having a substantially rectangular cross-sectional sectional shape. In some embodiments, at least one of the second filaments has a smaller cross-sectional dimension than a cross-sectional dimension of at least one of the plurality of first filaments.

In some embodiments of the present disclosure, another multifilar coil is disclosed and includes a first plurality of adjacent first filaments helically wound about a long axis, each of the first filaments having a substantially equal first lateral flexibility. The multifilar coil may further include a second plurality of adjacent second filaments, the second plurality wound adjacent, along the long axis, to the first plurality, each of the second filaments having a respective lateral flexibility less than the first flexibility. In one or more embodiments, upon application to the coil of a force normal to the long axis, the coil may tend to preferentially bend at a first coil region that is helically oriented about the long axis and defined by the first plurality.

In some embodiments, the ratio of the number of filaments of the first plurality to the number of filaments of the second plurality is greater than one. In other embodiments, the ratio of the number of filaments of the first plurality to the number of filaments of the second plurality is less than one or equal to one. In certain embodiments, the number of filaments of the first plurality to the number of filaments of the second plurality may be 2:3, 3:6, 2:4, 2:10, 3:2, 4:2, 8:2, or 8:4.

According to some aspects of the present disclosure, another multifilar coil is disclosed and includes a first plurality of adjacent first filaments helically wound about a long axis, each of the first filaments having a substantially equal first lateral flexibility. The multifilar coil further includes a second plurality of adjacent second filaments, the second plurality wound adjacent, along the long axis, to the first plurality, each of the second filaments having a respective lateral flexibility less than the first flexibility. The coil may bend to a degree defined by the first plurality, in a first direction at a first coil region, helically oriented about the long axis and, upon application of a force less than necessary to bend the coil to the degree in the first direction, to a second degree defined by the second plurality at a second coil region, which is also helically oriented about the long axis.

In some embodiments, upon application of the force, (i) at least two adjacent filaments of the first plurality may separate from each other by a first distance and (ii) a filament of the first plurality and an adjacent filament of the second plurality may separate from each other by a second distance, less than the first distance. In certain embodiments, upon application of the force, (i) at least two adjacent filaments of the first plurality may separate from each other by a first distance and (ii) at least two adjacent filaments of the second plurality may separate from each other by a second distance, less than the first distance.

According to one or more embodiments, a coiled implant is disclosed and includes a multifilar outer coil including (i) one or more first filaments, each having a first stiffness and being helically wound about a long axis, and (ii) one or more second filaments, each having a second stiffness less than the first stiffness and being wound about the long axis. The coiled implant may further include a unifilar inner coil concentric within the outer coil, the inner coil being formed of an inner filament wound about the long axis, wherein a first region of the inner coil has gaps between adjacent windings of the inner filament, and adjacent windings of the inner filament contact each other in an optional second region of the inner coil.

In some embodiments, a first region of the outer coil may have a first flexibility permitting bending at the first region in a first direction relative to the long axis. The first flexibility may be greater than a second flexibility permitting bending, in the first direction, of a second region of the outer coil that is (i) spaced apart from the first region along the long axis and (ii) sized equal to the first region. In some embodiments, a width of at least one of the gaps is at least about 20%, about 40%, about 60%, about 80%, about 100%, about 150%, or about 200% of a width of the inner filament. In some embodiments, one of the outer coil and the inner coil may be dextrorotary and the other of the outer coil and the inner coil may be levorotary. In one or more embodiments, one or more of the second filaments may be interwound, about the long axis, with some of the first filaments. In some embodiments, the outer coil defines gaps between adjacent windings of the first and/or second filaments. In some embodiments, a pitch of the inner coil may be at least twice a pitch of the outer coil.

According to one or more aspects of the present disclosure, a coiled implant is disclosed that may include a multifilar outer coil comprising (i) one or more first filaments, each having a first stiffness and being helically wound about a longitudinal axis, and (ii) one or more second filaments, each having a second stiffness, less than the first stiffness and being wound about the longitudinal axis. The coiled implant may further include a multifilar inner coil concentric within the outer coil. The inner coil may be formed of at least one group of adjacent inner filaments wound about the longitudinal axis. Moreover, the inner coil may have a gap between adjacent windings of the at least one group of adjacent inner filaments. In one or more embodiments, a width of at least one of the gaps is about 20%, about 40%, about 60%, about 80%, about 100%, about 150%, or about 200% of a width of the at least one of the inner filaments. Moreover, a pitch of the inner coil may be at least twice a pitch of the outer coil.

According to some aspects, another coiled implant is disclosed that may include a multifilar outer coil comprising (i) one or more first filaments, each having a first stiffness and being helically wound about a longitudinal axis, and (ii) one or more second filaments, each having a second stiffness, less than the first stiffness and being wound about the longitudinal axis. The coiled implant may further include a multifilar inner coil concentric within the outer coil, the inner coil being formed of at least one group of adjacent inner filaments wound about the longitudinal axis. The filaments of the inner coil may have a pitch that is at least about twice the pitch of the outer coil. In some embodiments, the pitch of the inner coil filaments is at least 3×, at least 4×, or at least 6× the pitch of the outer coil.

In some embodiments, a first region of the outer coil may have a first flexibility permitting bending at the first region in a first direction relative to the long axis. The first flexibility may be greater than a second flexibility permitting bending, in the first direction, of a second region of the outer coil that is (i) spaced apart from the first region along the long axis and (ii) sized equal to the first region. In some embodiments, one of the outer coil and the inner coil may be dextrorotary and the other of the outer coil and the inner coil may be levorotary.

According to one or more aspects of the present disclosure, a coil is disclosed and may include a primary filament winding having (a) a first shape of a first cross-section of a first segment of the coil, and (b) a second shape of a second cross-section of a second segment of the coil. The first and second cross-sections may be orthogonal to a long axis of the coil, and the first and second segments may be spaced apart along the long axis. Moreover, the second shape may be different from the first shape, irrespective of (a) an angular orientation, about the long axis, of the first shape with respect to the second shape, and (b) relative sizes of the first and second shapes.

In some embodiments, the second segment may have a different lateral flexibility than the first segment. The first shape may be curved and the second shape may be polygonal. In certain embodiments, the first shape may be circular or oval and the second shape may be polygonal. In some embodiments, the second shape is triangular. In certain embodiments, the first shape is polygonal and the second shape is polygonal, different from the first shape. In at least one embodiment, the second shape is triangular. In some embodiments, the first shape may be circular and the second shape may be elliptical.

According to one or more aspects of the present disclosure, a coil is disclosed that may include at least one filament arranged in a helical primary winding. The coil may have a cross-section, orthogonal to a longitudinal axis of the coil, that tapers over a region that extends at least one-fourth of an entire longitudinal length of the coil.

According to one or more aspects of the present disclosure, a coil is disclosed that may include at least one filament arranged in a helical primary winding. The filament may have a first cross-sectional dimension, orthogonal to a longitudinal axis of the filament, that is tapered over a region of at least two 360° turns of the winding. In some embodiments, the region is at an end portion of the coil. In certain embodiments, the region is at a distal end. In yet other embodiments, the region is at a proximal end. In some embodiments, the taper is nonlinear. In certain embodiments, however, the taper may include at least one stepwise change in the first cross-sectional dimension along the axis. The coil may further include inner and outer cross-sectional dimensions. The inner cross-sectional dimension may surround a lumen within the coil and does not substantially taper over the at least two turns.

According to one or more aspects of the present disclosure, a coiled implant is disclosed that may include an outer coil arranged in a first winding having a circular or oval cross-sectional shape, and an inner coil concentric within the outer coil and arranged in a second winding having a polygonal cross-sectional shape. In some embodiments, a direction of the first winding and a direction of the second winding direction are opposite. In some embodiments, the polygonal shape is triangular or rectangular. In at least one embodiment, a rotational orientation of the inner coil cross-sectional shape may vary along a long axis of the inner coil. The coiled implant may further include a first region that has a first flexibility permitting bending at the first region in a first direction relative to the long axis. The first flexibility may be greater than a second flexibility permitting bending, in the first direction, of a second region of the implant that is spaced apart from the first region along a long axis of the implant.

According to one or more aspects of the present disclosure, a coiled implant is disclosed that may include an outer coil arranged in a first winding having a first polygonal cross-sectional shape, and an inner coil concentric within the outer coil and arranged in a second winding having a second polygonal cross-sectional shape. In some embodiments, a direction of the first winding and a direction of the second winding direction are opposite. In one or more embodiments, at least one of the first and second polygonal shapes is triangular or rectangular. In some embodiments, however, the first and second shapes are the same. Moreover, a rotational orientation of the inner coil cross-sectional shape may vary along a longitudinal axis of the inner coil. The coiled implant may further include a first region that has a first flexibility permitting bending at the first region in a first direction relative to the long axis. The first flexibility may be greater than a second flexibility permitting bending, in the first direction, of a second region of the implant that is spaced apart from the first region along a long axis of the implant.

According to one or more aspects of the present disclosure, a method of deploying a coil implant is disclosed. The method may include advancing at least a portion of a coil implant into an aneurysm. The coil implant may include a plurality of concentric coils, each having a respective winding direction. The winding directions of two of the coils may be opposite each other. The method may further include providing torque to at least one of the concentric coils such that at least one of the coils radially expands or contracts and transfers a portion of the torque to a radially adjacent coil. In some embodiments, providing torque includes rotating the implant while positioning the implant in the aneurysm. In some embodiments, rotating the implant may cause the implant to form a loop by overlapping with itself.

In some embodiments, providing torque may include rotating a delivery system attached to the implant. The delivery system may be attached to the implant by a coupling that restricts relative rotation between the implant and the delivery system. In at least one embodiment, the relative rotation may be limited to less than 360°, 180°, 120°, 90°, 60°, 45°, 30°, 20° 10°, 5°, or 2° of rotation. In some embodiments, the rotating results in expansion of the implant to a configuration that contacts a wall of the aneurysm at multiple points. In certain embodiments, rotating the implant increases a packing density of the implant in the aneurysm. In some embodiments, at least one of the coils may be unifilar. Some embodiments provide that at least one of the coils is multifilar.

Methods of manufacturing a coiled implant are disclosed that, in some instances, include winding a first filament to form a first coil, and heat treating the first coil. The method may further include winding a second filament to form a second coil, and inserting one of the first and second coils into a lumen of the other of the first and second coils after the heat treating. In some embodiments, the heat treating of the first coil is at a condition that would change at least one of physical, chemical, and/or biological characteristic of the second coil and thereby render the second coil unsuitable for treatment of the patient. In some instances, changing a physical characteristic of the second coil and thereby rendering the second coil unsuitable for treatment of a patient can include, without limitation, melting, annealing, evaporating, sublimating, singeing, causing a phase transition of, rendering inert, charring, and rendering non-biocompatible a material of the second coil. In at least one embodiment, heat treating may form the first coil into at least one of a primary shape and a secondary shape.

In some embodiments, at least one of the first and the second filament is wound into a substantially helical tubular shape. In some embodiments, one of the first and the second filament may be wound about a mandrel, and the filament wound about the mandrel is inserted, on the mandrel, into the lumen of the other of the first and second coils. The method may further include separating the mandrel from the other of the first and second coils. In some embodiments, the first filament may include a different material than the second filament. In some embodiments, the first filament is a metal. In some embodiments, the second coil may be heat treated at a condition that would not at least one of melt, anneal, evaporate, singe, cause a phase transition of, render inert, and render non-biocompatible the material of the second coil.

According to one or more aspects of the present disclosure, another method of manufacturing a coiled implant is disclosed. The method may include winding a first filament to form a first coil, and heat treating the first coil. The method may also include winding a second filament onto the first coil after the heat treating to form a second, outer coil. Heat treating the first coil may be at a condition that would at least one of melt, anneal, evaporate, singe, cause a phase transition of, render inert, and render non-biocompatible a material of the second coil. Moreover, heat treating of the first coil may form the first coil into at least one of a primary shape and a secondary shape. In at least one embodiment, the second coil may be heat treated at a condition that would not at least one of melt, anneal, evaporate, singe, cause a phase transition of, render inert, and render non-biocompatible the material of the second coil. In some embodiments, the first filament may be made of a different material than the second filament. In at least one embodiment, however, the first filament is made from a metal.

According to one or more aspects of the present disclosure, methods of manufacturing a coiled implant are disclosed that provide winding a first filament to form a first coil having a helical gap in the winding and heat treating the first coil. The method may further include winding a second filament into the gap after the heat treating, thereby forming a second coil interwound with the first coil. The first filament may be made from a different material than the second filament. In some embodiments, heat treating the first coil may form the coil into at least one of a primary shape and a secondary shape. Moreover, heat treating of the first coil may be at a condition that would change at least one of a physical, chemical, and biological characteristic of the second coil and thereby render the second coil unsuitable for treatment of the patient. In other embodiments, heat treating of the first coil is at a condition that would at least one of melt, anneal, evaporate, singe, cause a phase transition of, render inert, and render non-biocompatible a material of the second coil. In yet other embodiments, the second coil is heat treated at a condition that would not at least one of melt, anneal, evaporate, singe, cause a phase transition of, render inert, and render non-biocompatible the material of the second coil In some methods described herein of manufacturing a coiled implant for implantation in, and treatment of, a patient, the methods include winding a first filament to form a first coil; heat treating the first coil; winding a second filament to form a second coil; and inserting one of the first and second coils into a lumen of the other of the first and second coils after the heat treating. In some instances, the heat treating of the first coil is at a condition that would change at least one of a physical, chemical, and biological characteristic of the second coil and thereby render the second coil unsuitable for treatment of the patient. In some instances, the heat treating is performed in a manner so as not to compromise performance of a coil. For example, various heat treating processes may melt, anneal, evaporate, singe, cause a phase transition of, render inert, and/or render non-biocompatible a material of the second coil, all of which may compromise performance of the coil. As a result, for example, the second coil may be heat treated at a condition that would not at least one of melt, anneal, evaporate, singe, cause a phase transition of, render inert, and render non-biocompatible the material of the second coil.

According to one or more aspects of the present disclosure, a coil is disclosed that may include a coil winding having a first material and a second material. The first material may receive heat treatment, after being formed into a first coil, under conditions that would change at least one of a physical, chemical, and biological characteristic of the second coil and thereby render the second coil unsuitable for treatment of the patient. For example, the conditions may melt, anneal, evaporate, singe, destroy, alter, render non-biocompatible, or otherwise compromise the properties of the second material. In some embodiments, the coil may have a primary coil winding (e.g., a helical winding). In some embodiments, after the coil is formed to have the primary coil winding, the coil may further be formed into a secondary coil shape (e.g., a shape formed by wrapping or folding the coil into a spherical or other shape).

The heat treatment may impart one of a primary shape and a secondary shape to the primary coil winding. The heat treatment may be configured to impart one of a primary shape and a secondary shape to the secondary coil winding. In some embodiments, the first coil may be made from the first material and the second material forms a second coil, the first and second coils being interwound. The second coil may be interwound with the first coil after the heat treatment. In one or more embodiments, the second coil may be coaxial with the first coil. In some embodiments, one of the first coil and the second coil may be dextrorotary and the other of the first coil and the second coil may be levorotary.

According to one or more aspects of the present disclosure, a coil is disclosed that may include a first coil winding having a first secondary shape, and a second coil winding wound over the first coil winding and having a second secondary shape, different from the first secondary shape. In some embodiments, the second coil winding may not be heat treated into either a primary shape or the secondary shape. The first coil winding, however, may be formed by heat treatment into the first secondary shape. In some embodiments, the second coil winding may be wound over the first coil winding after the heat treatment.

According to one or more aspects of the present disclosure, a system for treating vascular disease is disclosed. The system may include a coil implant that has at least one filament wound about, and having a lumen extending along, a coil long axis. The system may further include a securing member, coupled to the implant, and having a member long axis and extending within the lumen in a direction of the coil long axis. The member may have a first transverse axis and a second transverse axis normal to the first transverse axis, both transverse axes being normal to the coil long axis. The member may have (a) a first resistance to bending away from the coil long axis toward the first transverse axis, and (b) a second resistance to bending away from the coil long axis toward the second transverse axis, the first resistance to bending greater than the second resistance to bending.

In some embodiments, the member may be helically twisted along the member long axis. The member may have a shape of a cross-section, normal to the member long axis, that is substantially polygonal. In some embodiments, the shape is substantially rectangular. In other embodiments, however, the member may have a shape of a cross-section, normal to the member long axis, that is substantially oval.

Additional features and advantages of the technology will be set forth in the description below, and in part will be apparent from the description, or may be learned by practice of the disclosure. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the technology and together with the description serve to explain the principles of the disclosure.

FIG. 1b shows a closer view of a portion of FIG. 1a.

FIG. 2b illustrates a side view of another exemplary positioning system, according to one or more embodiments disclosed.

FIG. 2c illustrates an enlarged view of an exemplary coiled implant as shown in FIG. 2b, according to one or more embodiments disclosed.

FIG. 4a illustrates a side view of another exemplary multifilar coil that may be used in conjunction with the system of FIG. 2a or 2b, in accordance with various embodiments of the subject technology.

FIG. 4b illustrates a cross-sectional side view of the multifilar coil of FIG. 4a, according to one or more embodiments.

FIG. 5 illustrates a side view of another exemplary multifilar coil that may be used in conjunction with the system of FIG. 2a or 2b, in accordance with various embodiments of the subject technology.

FIG. 6 illustrates a side view of another exemplary multifilar coil that may be used in conjunction with the system of FIG. 2a or 2b, in accordance with various embodiments of the subject technology.

FIGS. 11a and 11b illustrate side views of exemplary coils that may be used in conjunction with the system of FIG. 2a or 2b, in accordance with various embodiments of the subject technology.

FIG. 12 illustrates a side view of another exemplary coil that may be used in conjunction with the system of FIG. 2a or 2b, in accordance with various embodiments of the subject technology.

FIGS. 19a and 19b illustrate side views of exemplary configurations of the securing member depicted in FIG. 18, in accordance with various embodiments of the subject technology.

FIGS. 19c and 19d illustrate cross-sectional views of exemplary configurations of the securing member depicted in FIG. 18, in accordance with various embodiments of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the description.

In one or more embodiments, the systems and devices disclosed herein may be used in veterinary or human medicine and, more particularly, for the endovascular treatment of intracranial aneurysms and acquired or innate arteriovenous blood vessel malformations and/or fistulas and/or for the embolization of tumors by thromboembolization. For this purpose, components of the various systems and devices disclosed herein may be designed as a stent, a coil implant, a filter, and the like, but may as well possess any other superimposed configuration as may be expedient. In one or more embodiments, the systems and devices disclosed herein may provide various designs and configurations for an aneurysm coil, as especially appropriate for the occlusion of intracranial aneurysms.

Figure 1A:
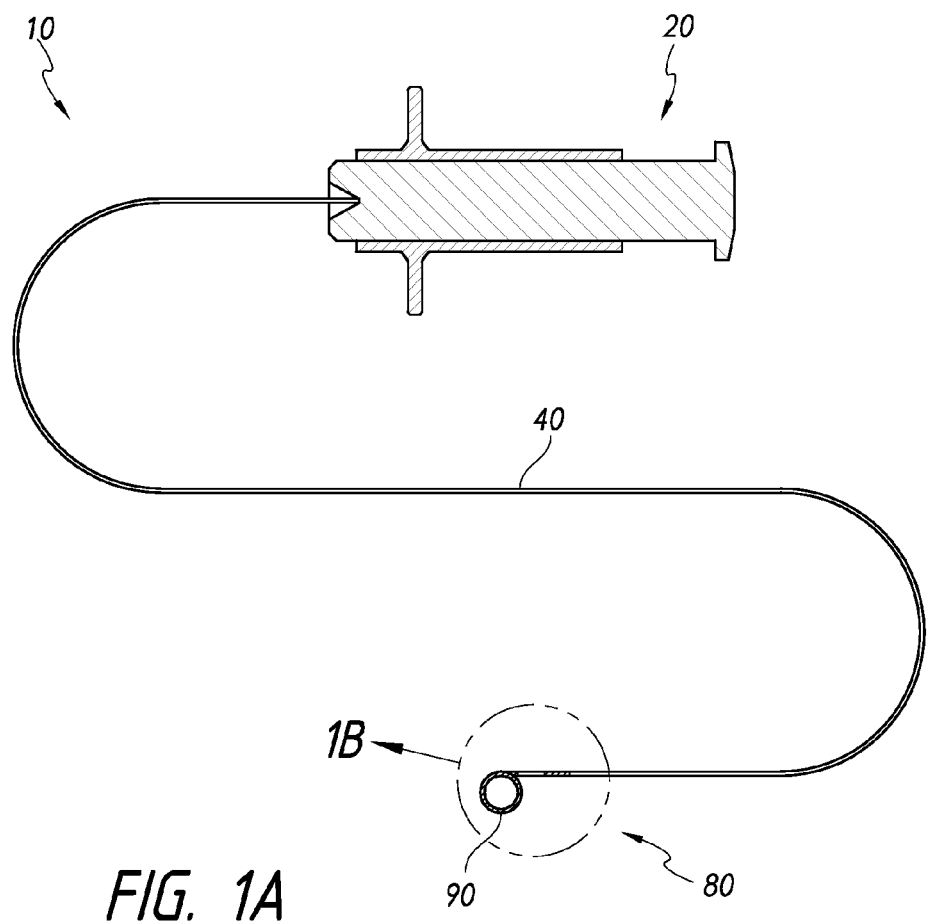
FIG. 1a shows a plan view of the positioning system in accordance with some embodiments of the subject technology, and a plan view of an exemplary implant in accordance with some embodiments of the subject technology.
Figure 1B:
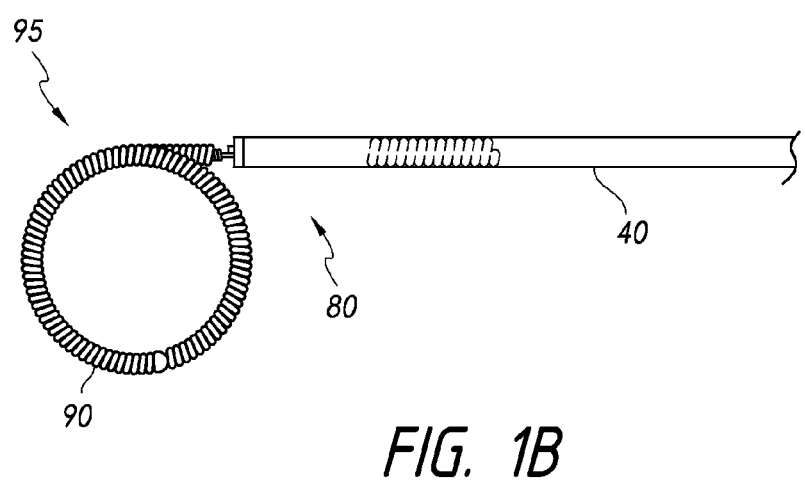

A vascular implant device may be a positioning system 10 such as the one shown in FIGS. 1a-1b. The positioning system 10 shown in FIGS. 1a-1b includes an actuator 20, a positioner 40 coupled with the actuator 20, and an implant interface 80 at the distal end of the positioner 40. A portion of the implant interface 80 may engage a complementary portion of an implant 95 in order to control the delivery (i.e., securing and detaching) of the implant 95 at the desired location. While the implant is shown or described in several embodiments as comprising an embolic coil 90, any implant or device that is compatible with the subject technology may be used in lieu of or in conjunction with the coil 90 in accordance with the embodiments described herein. Suitable implants and devices include, but are not limited to, stents, filters, thrombectomy devices, atherectomy devices, flow restoration devices, embolic coils, embolic protection devices, or other devices, and the like. Moreover, it will be appreciated that both detachable and non-detachable implants and/or devices may be used with the delivery or positioning system 10.

Figure 1C:
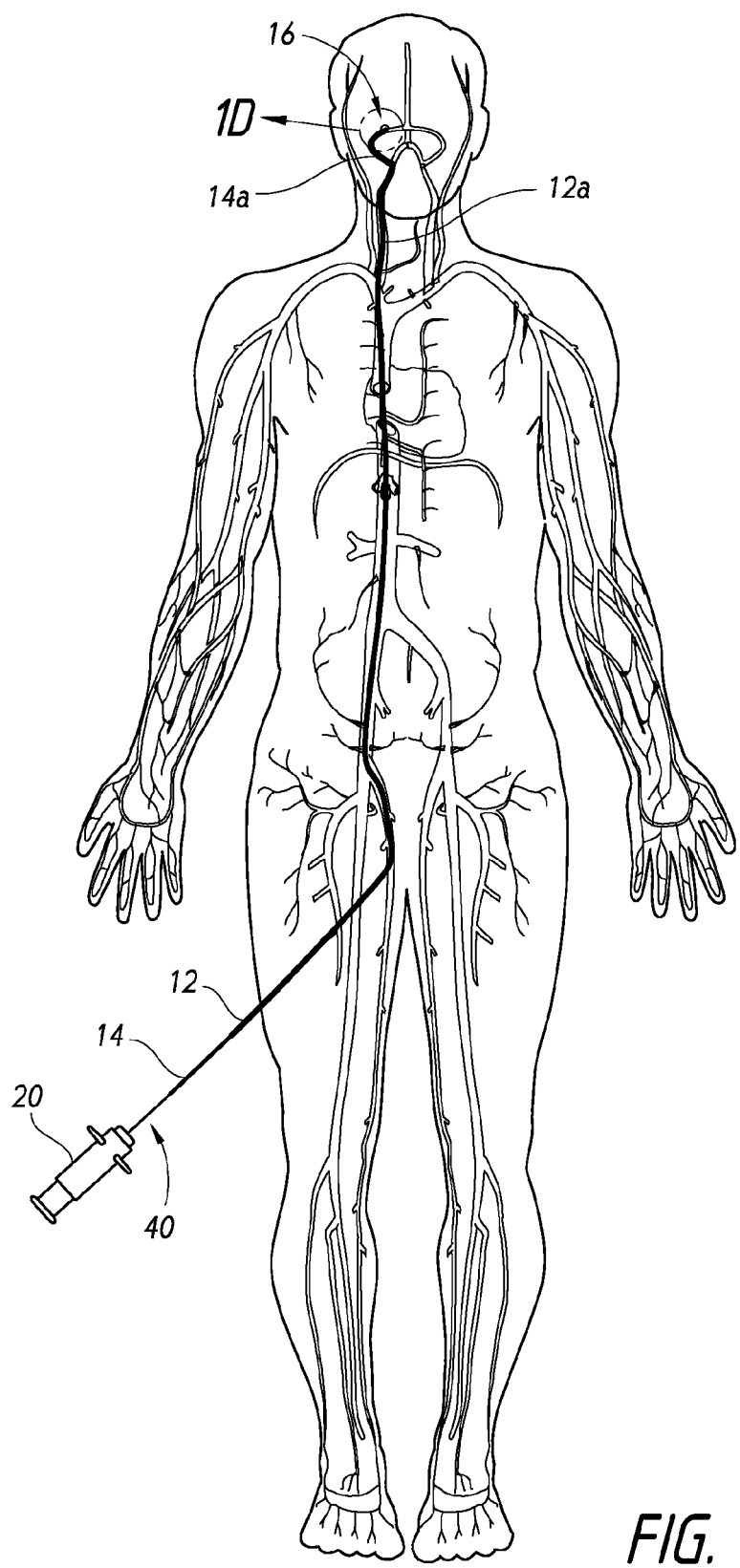
FIG. 1c shows a plan view of the position system of FIG. 1a within the human body.

FIG. 1c shows the positioning system 10 of FIGS. 1a-1b used inside a patient's vasculature. In the embodiment shown in FIG. 1c, an operator uses a guide tube or guide catheter 12 to position a delivery tube or microcatheter 14 in a patient's vasculature. This procedure involves inserting the guide catheter 12 into the patient's vasculature through an access point such as the groin, and directing the distal end 12a of the guide catheter 12 through the vascular system until it reaches the carotid artery. After removing a guide wire (not shown) from the guide catheter 12, a microcatheter 14 may be inserted into the guide catheter 12 and the distal end 14a of the microcatheter 14 subsequently exits the guide catheter distal end 12a and may be positioned near the target site 16, such as an aneurysm in the patient's brain.

Figure 1D:
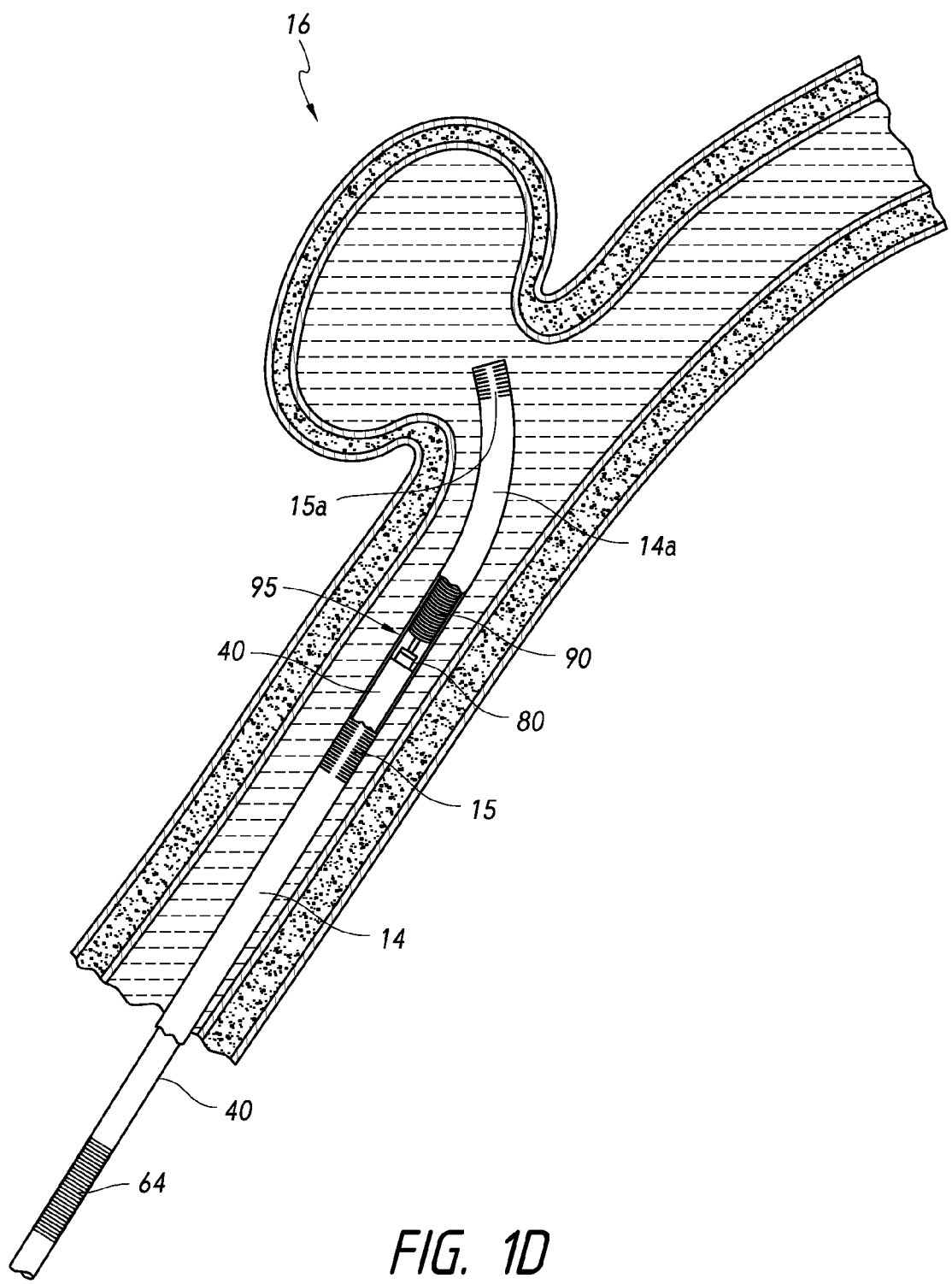
FIG. 1d shows a closer view of a portion of FIG. 1c showing the positioning system in partial cross-section and an exemplary implant in accordance with some embodiments of the subject technology in a position within the human body.
Figure 1E:
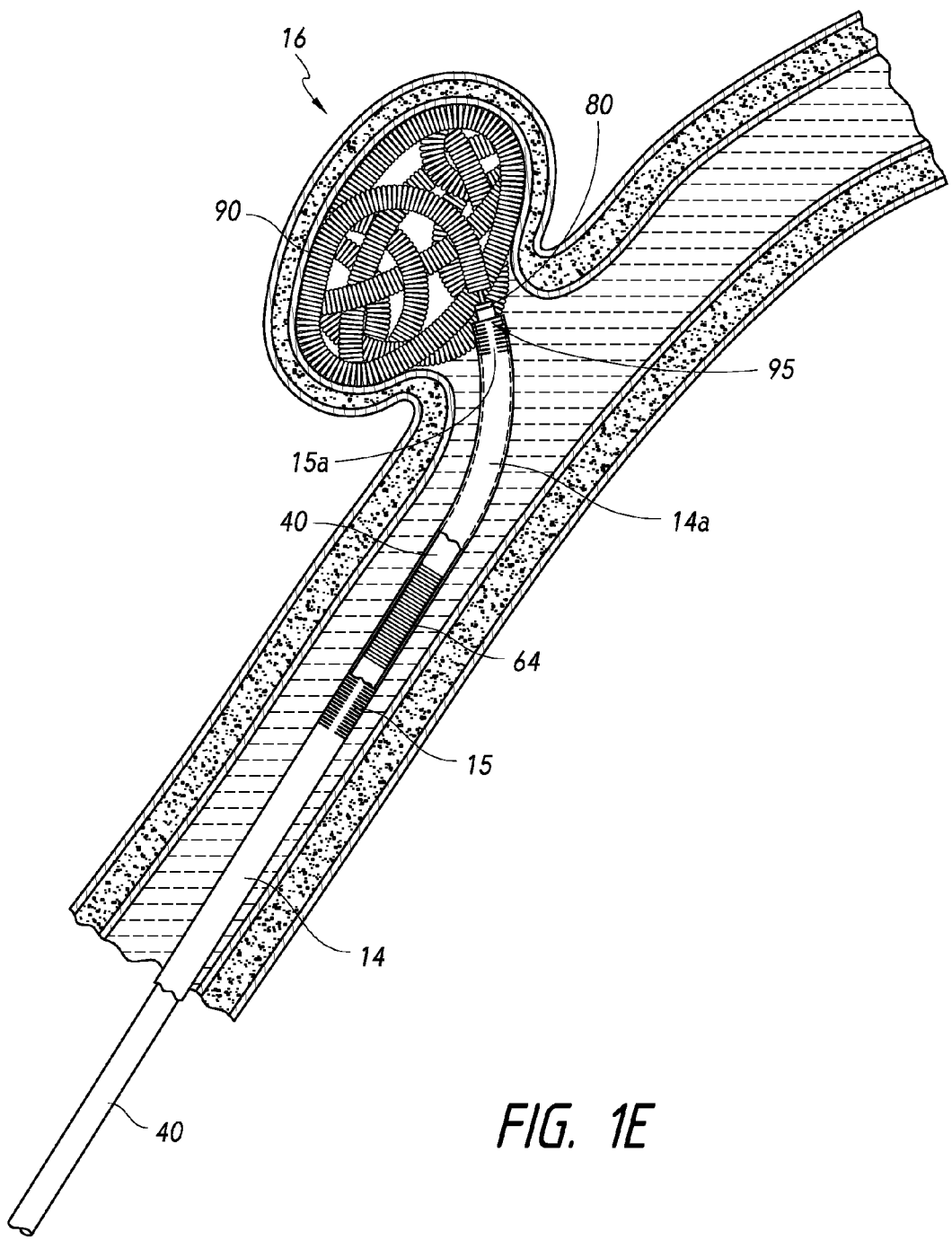
FIG. 1e shows a closer view of a portion of FIG. 1c showing the positioning system in partial cross-section and an exemplary implant in accordance with some embodiments of the subject technology in another position within the human body.

In the embodiments illustrated in FIGS. 1d and 1e, the microcatheter 14 can include microcatheter markers 15 and 15a that facilitate imaging of the distal end 14a of the microcatheter 14 with common imaging systems. After the distal end 14a reaches the target site 16, the positioning system 10 of the illustrated embodiment is then inserted into the microcatheter 14 to position the implant interface 80 at the distal end of the positioner 40 near the target site 16, as illustrated in FIG. 1d. The implant 95 can be attached to the implant interface 80 prior to inserting the positioning system 10 into the microcatheter 14. This mode of implant delivery is illustrated in FIGS. 1c-1e. The delivery of the implant 95 is facilitated by disposing the microcatheter marker 15a near the target site 16, and aligning the microcatheter marker 15 with a positioner marker 64 in the positioner 40 which, when the two markers (markers 15 and 64) are aligned with each other as illustrated in FIG. 1e, indicates to the operator that the implant interface 80 is in the proper position for the release of the implant 95 from the positioning system 10.

Referring to FIGS. 1a-1b, the implant interface 80 is a portion of the positioning system 10 that allows the operator to mechanically control the engagement and disengagement of the implant 95 to the positioner 40, and allows the positioner 40 to retain the implant 95 in a way that minimally contacts the implant 95, that permits movement of the implant relative to the positioner in some or all of axial, tilt, and rotational directions, and that allows the implant 95 to move axially and without radial movement when engaging and disengaging the implant interface 80.

Figure 2A:
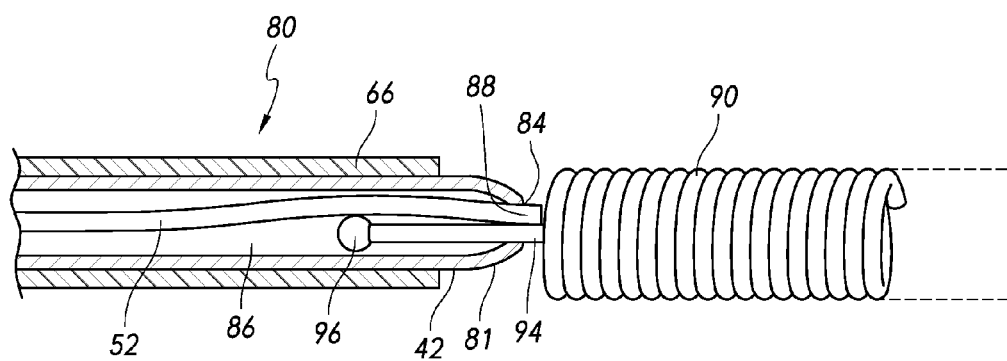
FIG. 2a illustrates a partial cross-sectional view of an exemplary positioning system, according to one or more embodiments disclosed.

Referring now to FIG. 2a, illustrated is an enlarged view of an exemplary implant interface 80, according to one or more embodiments. The positioner 40 as generally described above may include an elongate positioner tube 42 which houses a wire or cord 52 that is translatable within the tube 42 when moved by an operator. The distal end of the positioner tube 42 engages the implant interface 80 and may terminate at an end cap or dome 81. In other embodiments, the end cap 81 can be replaced by a partial or whole loop, ring, or eyelet, and/or carried by a stiffening member disposed at a distance from the positioner tube 42. The end cap 81 may have a port 84 through which positioner tube 42 communicates with the exterior environment of the positioner 40 or the interior of the microcatheter 14 (FIGS. 1c-e), depending on the position of the positioner 40 in relation to the microcatheter 14. Enclosed about the longitudinal length of the positioner tube 42 is a positioner tube sleeve 66 that provides a sliding exterior surface to the positioner tube 42 that facilitates the insertion and sliding of the positioner tube 42 into and through the microcatheter 14. The positioner tube sleeve 66 increases lubricity between the positioner tube 42 and the inner lumen surface of the microcatheter 14 and increases the structural integrity of the positioner tube 42.

The implant interface 80, may be configured to allow the operator to mechanically control the engagement and disengagement of the implant 95, such as the coil 90, to the positioner 40 in various ways. The interface 80 further allows the positioner 40 to retain the implant 95 in a way that minimally contacts the implant 95, that permits movement in all directions of motion and rotationally, and that allows the implant 95 to move axially and without radial movement when engaging and disengaging the positioner 40. In one or more embodiments, the implant interface 80, in conjunction with the positioner 40, provides mechanical control of the engagement and disengagement of the implant 95 by retaining a member (e.g., rod 94) that engages the implant 95. The member may be introduced into the implant interface 80 through an opening (e.g., port 84) in the positioning system 10, and retained at the implant interface 80 by obstructing the opening at least in part, or fully, so as to physically prevent the complete exit of the member back through the opening.

In one or more embodiments, obstruction is achieved with a movable elongate member (e.g., the cord 52) disposed along the length of the positioning system 10 with a distal end that obstructs the opening. By obstructing the opening and not fixedly restraining the implant 95, the implant 95 remains free to move according to the limitations defined by the implant interface 80, which includes movement in the axial and radial directions compared to the axis of the positioning system 10, rotational movement about an axis of the implant 95, and angular movement that disposes the implant 95 at an angle as compared to the axis of the positioning system 10. Furthermore, by obstructing the opening and not directly restraining the implant 95, the contact between the implant interface 80 and the implant 95 may be minimized.

Referring specifically to the exemplary embodiment shown in FIG. 2a, the cord 52 may be disposed at the implant interface 80. A distal tip 88 of the cord 52 is positioned in the port 84 of the end cap 81 so that it partially obstructs the port 84 when the cord 52 is at its most distally advanced position in the positioner tube 42. The positioner tube 42 and the end cap 81 cooperatively define a cavity 86 within the implant interface 80. The distal tip 88 of the cord 52 is disposed within the port 84 in the end cap 81 and prevents an enlarged portion, e.g., a ball 96, carried by a rod 94 engaged by the implant 95 to move distally through the port 84. In some instances, the cord 52 can extend distally of the ball 96, and in some embodiments, the cord 52 can terminate radially adjacent the ball 96. In some embodiments, the cross-sectional dimension of the ball 96 coupled with the cross-sectional dimension of the cord 52 is too large for the ball 96 to pass through the port 84. In such embodiments, the cord 52 and ball 96 obstruct the port by their engagement with one another proximally of the port 84.

To detach the implant 95 from the positioner 40 at the implant interface 80, the cord 52 is moved in the proximal direction relative to the positioner tube 42 such that the distal tip 88 of the cord 52 is proximal of the port 84 in the end cap 81 and no longer obstructs the port 84. At this point, the ball 96 carried by the rod 94 and engaging the implant 95 is free to move distally through the port 84 or, alternatively, the positioner tube 42 or the entire positioner 40 can be moved in the proximal direction to allow the ball 96 to exit the positioner tube 42. In one or more embodiments, the proximal edges of the end cap 81 at the port 84 are rounded or chamfered to facilitate the exit of the ball 96 from the implant interface 80.

In another exemplary embodiment, the distal tip 88 of the cord 52 is not disposed in the port 84 of the end cap 81 but instead abuts against an interior surface of the end cap 81. The diameter or thickness of the distal tip 88 may be sufficient to obstruct the port 84 such that the ball 96 carried by the rod 94 is not able to freely move distally through the port 84. Proximal movement of the distal tip 88 removes the obstruction from the proximal edge of the port 84, thereby providing a means for the ball 96 carried by the rod 94 to exit the port 84 and detach the implant 95.

As will be appreciated by those skilled in the art, several methods or processes of mechanically detaching the implant 95 from the positioner 40 at the implant interface 80 are possible. In some embodiments, such as is described briefly above, the implant 95 is detached or otherwise released from the positioner 40 through proximal translation of the cord 52. For example, the cord 52 may be pulled proximally with respect to the implant interface 80. In other embodiments, the positioner 40 may be pushed distally such that the implant interface 80 moves distally with respect to the cord 52. In one or more embodiments, detaching the implant 95 from the positioner 40 includes breaking a portion of the cord 52 free from mechanical, welded, or adhesive engagement with the ball 96 or the rod 94. In other embodiments, detaching the implant 95 from the positioner 40 includes plastically deforming one of the cord 52, the ball 96, or the rod 94 such that mutual engagement between such components is eliminated and the implant 95 is thereby freed. In yet other embodiments, detaching the implant 95 from the positioner 40 includes removing frictional engagement between the cord and one or both of the ball 96 and the rod 94.

In yet further embodiments, detaching the implant 95 from the positioner 40 at the implant interface 80 may be realized through an electrolytic process. For instance, referring now to FIGS. 2b and 2c, illustrated is another exemplary positioning system 100, according to one or more embodiments disclosed. The system 100 has a proximal end 102a and a distal end 102b and may include the implant 95, such as a coiled implant, arranged at or adjacent the distal end 102b. The system 100 may further include the positioner 40 extending from the user in conjunction with the implant interface 80. In one or more embodiments, the implant interface 80 may include a severance module 106 coupled to or otherwise arranged adjacent the implant 95. As illustrated, the system 100 may be a generally elongate structure having a long axis or longitudinal axis 110 where each of the implant 95, the severance module 106, and the positioner 40 are axially-offset along said longitudinal axis 110. As used herein, "long axis" and "longitudinal axis" are used interchangeably.

A retaining element 112 may be configured to generally extend along the longitudinal axis 110 of the system 100 from the proximal end 102a to the distal end 102b. In one or more embodiments, the retaining element 112 may be coupled on one end to the distal end 102b and to the rod 94 on an opposite end. In some embodiments, the retaining element 112 may extend through the implant 95 in order to substantially prevent the implant 95 from elongating axially. In one or more embodiments, the retaining element 112 extends within contiguous lumens defined within each of the implant 95 and the implant interface 80. As used herein, the terms "proximal" and "distal" are understood in such a way that "proximal" refers to a point situated in a direction away from the target treatment site, that is towards the user interface (for example, the actuator) for the surgeon or user, whereas "distal" points to the treatment site within the organism, i.e., away from the user interface.

Referring to FIG. 2c, with continued reference to FIG. 2b, illustrated is an enlarged view of the exemplary implant 95, according to one or more embodiments. The implant 95 may have a proximal end 202a and a distal end 202b. As illustrated, the distal end 202b may include a distal tip 204 coupled or otherwise attached thereto. In one embodiment, the distal tip 204 is designed as an atraumatic head that prevents damage to the vasculature of the patient while the implant 95 traverses within the patient or otherwise prevents the implant 95 from binding against the inner walls of the vasculature. Simultaneously, the distal tip 204 may serve as a distal implant marker enabling the implant 95 to be placed in position under radiographic observance. To this end, in at least one embodiment, the distal tip 204 is made of a platinum/iridium alloy or other radiopaque material, but may be made of other materials or combinations of materials without departing from the scope of the disclosure. For example, in at least one embodiment, the distal tip 204 is made of non-radiopaque polypropylene.

At its proximal end 202a, the implant 95 may be coupled to the positioner 40 via the severance module 106 and/or the implant interface 80 (FIG. 2b). In some embodiments, the proximal end 202a is welded at one or more seams 206 in order to be coupled to the severance module 106. In other embodiments, however, the seams 206 may include a mechanical or adhesive attachment means enabling the implant 95 to be coupled or otherwise attached to the positioner 40 via the severance module 106. In some embodiments the coil implant 95 is electrically isolated from the severance module 106, in one example, by using polymer adhesive as the coupling. According to one or more embodiments, the implant 95 may be coated with one or more medically-effective substances such as, for example, a thrombogenic agent.

In some embodiments, the implant 95 is made of a wire 208 that has been wound multiple times to form a generally tubular structure. In at least one embodiment, the wire 208 is wound so as to form a spiral helix, for example, a spiral helix forming several contiguous loops or windings having a pitch that is constant or alternatively varies over the length of the implant 95. As will be described below, however, the wire 208 may be formed or otherwise wound into several alternative configurations without departing from the scope of the disclosure. In one or more embodiments, the wire 208 may be made of a nickel-titanium alloy (e.g., nitinol) which possesses both mechanical and thermal shape memory characteristics. In other embodiments, however, the wire 208 may be made of any material exhibiting mechanical and/or thermal shape memory characteristics or, alternatively, platinum, platinum alloys, tungsten, tungsten alloys, or other like materials.

In some embodiments, after detachment the implant 95 may assume a predetermined, superimposed configuration. As used herein, the term "superimposed" may refer to a shape or configuration that the implant 95 is configured to assume as preprogrammed through one or more heat treatment processes or methods undertaken by the wire 208. As discussed in more detail below, the superimposed configuration may include the implant 95 assuming a primary and/or a secondary shape. In some embodiments, the retaining element 112 extends through the implant 95 and operates to limit longitudinal stretching of the implant 95. For example, the retaining element 112 may have a length that is shorter than a length that the implant 95 may be stretched to which would thereby cause plastic deformation or general unwinding of the implant 95. Many such embodiments are described in U.S. Patent Pub. No. 2010/0030200, the contents of which are hereby incorporated by reference to the extent not inconsistent with the present disclosure.

To properly position the implant 95 at the treatment site, the implant 95 is coupled to, or at least manipulated by, the positioner 40 and implant interface 80 (FIG. 2b) and maneuvered towards the treatment site using the delivery catheter, such as a micro-catheter 14 (FIG. 1c). In some embodiments, the positioner 40 and the retaining element 112 may be sized such that they can be separately manipulated by the user. In one or more embodiments, the positioner 40 and the retaining element 112 are designed as straightforward linear elements that extend proximally through the micro-catheter and ultimately to the user who can simultaneously manipulate them together with the micro-catheter. Having reached the treatment site, the implant 95 accommodating the retaining element 112 is pushed out of the micro-catheter distally and placed in position. Accuracy of the placement may be verified under radiographic observance.

As will be appreciated, the predetermined, superimposed configuration of the implant 95 may vary depending on the application or to suit the respective purposes for the system 100 (FIG. 2b). For example, the superimposed configuration of the implant 95 may be basket-shaped or tubular, which configurations are particularly effective in occluding vascular malformations. In other embodiments, however, the superimposed configuration provides a generally tubular structure which may be employed, for example, as a stent or an aneurysm coil. Accordingly, the superimposed configuration may constitute a coil or spring, such as a spiral helix or helical spring. These structures exhibit an essentially tubular structure, which is typical of stents and aneurysm coils, and are also advantageously flexible and stable. Nevertheless, the implant 95 may also exhibit other shapes and/or profiles such as, but not limited to, a profiled section or a folded form. Several variations and configurations of the implant 95 are described in detail below.

In applications where the implant 95 is to be delivered to fine intracranial or cerebral vessels, implants having a coiled or spring structure may be particularly suited. As can be appreciated, the specific sizing of the implant 95 may be governed by the size of the treatment site or destination vessel and may be easily determined by those skilled in the art. For example, in some embodiments, the primary shape of the implant 95 may have an outer diameter ranging between about 0.5 mm and about 10 mm. In other embodiments, however, the outer diameter of the implant 95 may be less than about 0.5 mm and greater than about 10 mm, without departing from the scope of the disclosure.

As discussed above, the wire 208 forming the implant 95 may be of a material that exhibits mechanical and/or thermal shape memory characteristics. In some embodiments, the wire 208 may be made of platinum or platinum alloys that have undergone a stress relief anneal process configured to help the wire 208 "remember" the superimposed or primary wound shape and automatically expand thereto. Wire 208 made of platinum and platinum alloys, or of similar materials, may also undergo stress relief annealing in order to better remember a secondary shape of the implant 95. In other embodiments the wire may be a nickel-titanium alloy and undergo a heat treatment configured to help the alloy remember a preprogrammed shape. Such a heat treatment may be comprised of restraining the wire in the desired shape, heat treating the restrained wire, then releasing the restraint. In one or more embodiments, the diameter of the wire 208 may range between about 0.03 mm and about 0.3 mm. In other embodiments, the diameter of the wire 208 may range between about 0.05 mm and about 0.2 mm. In at least one embodiment, diameter of the wire 208 may be about 0.06 mm. In yet other embodiments, the diameter of the wire 208 may range from dimensions below about 0.03 mm and above about 0.3 mm, without departing from the scope of the disclosure.

As described above, the implant 95 may be formed as a spiral helix forming several contiguous loops having a pitch that may vary over the length of the implant 95. In applications where it is desired to occlude an aneurysm and/or otherwise provide areas of differing or preferred bending or flexibility, the pitch of the loops may be reduced from the middle of the implant 95 towards the ends 202a,b such that there will be a denser loop arrangement in the middle and a less dense loop arrangement at the ends 202a,b. Such embodiments, and variations thereof, are generally explained below with reference to FIG. 14.

Referring again to FIG. 2b, the positioner 40 (in conjunction with the implant interface 80) may introduce the implant 95 into body vessels and cavities. In some embodiments, the positioner 40 is a tubular structure or some other linear element that defines an inner lumen 114. As briefly described above, the positioner 40 and the implant 95 may be connected via the severance module 106 included in the implant interface 80. As will be appreciated, however, any connection that can be effectively detached from the implant 95 may be suitable for use as the implant interface 80. The severance module 106, for instance, may be suited for any kind of implant detachment or severance. For example, the severance module 106 may be designed for, but not limited to, mechanical, thermal, or electrochemical (e.g., electrolytic) detachment. Various exemplary mechanical detachment embodiments that may be used in conjunction with the system 100 are described in U.S. patent application Ser. No. 12/297,419, which published as U.S. Patent Pub. No. 2010/0030200, the contents of which are incorporated by reference, as stated above.

In applications designed for electrochemical severance of the implant 95 from the positioner 40, the severance module 106 may require a voltage source and a cathode. The positioner 40 may include an insulating sleeve 116 shrink-fitted onto the outer surface of the positioner 40 and used, for example, to prevent the positioner 40 from corroding electrolytically. The implant 95 may serve as an anode and be slidably-arranged within the catheter. The severance module 106 has a severance location 120 that is electrolytically-corrodible so that when in contact with a bodily fluid or the like, the implant 95 will be detached by electrolytic processes.

It will be appreciated that the sizing of the severance module 106 and/or of the helix forming the implant 95 may be selected such that it only represents a minimum length of the implant 95 and in this way will not impede the placement process. At the treatment site, such as at an aneurysm the implant 95 is positioned in front of the aneurysm entry point by slidingly moving the positioner 40 within the vasculature (not shown). Once the fully-shaped implant 95 has been optimally positioned, it may be detached from the positioner 40. The implant 95 will then remain in the aneurysm, causing the aneurysm to be occluded.

Figure 3:
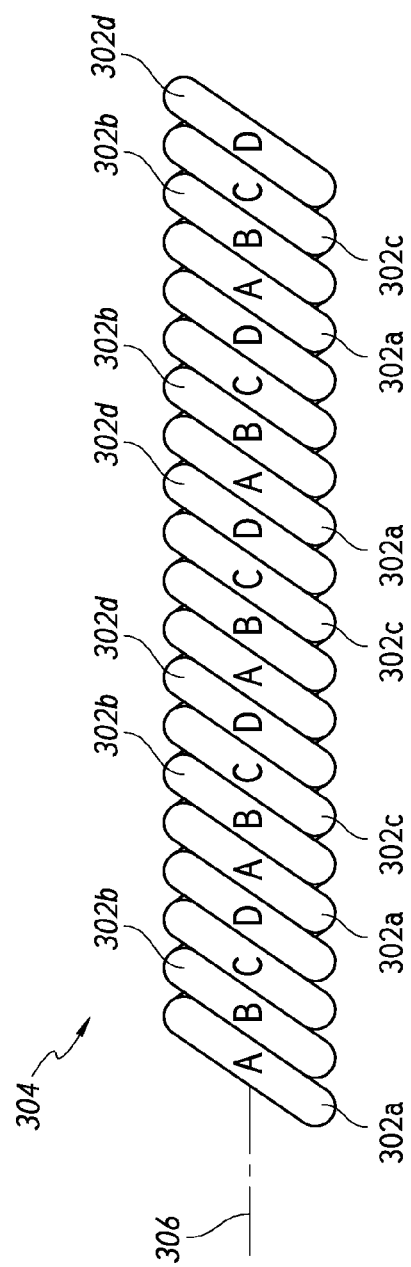
FIG. 3 illustrates a side view of an exemplary multifilar coil that may be used in conjunction with the system of FIG. 2a or 2b, in accordance with various embodiments of the subject technology.

Referring now to FIG. 3, illustrated is a multifilar coil 304, according to one or more embodiments. The multifilar coil 304 may be similar in some respects to the coil implant 95 generally described above with reference to FIGS. 2a-c. As such, the multifilar coil 304 may be adapted to replace or otherwise supplement the previously-described coil implant 90, and thereby be used in conjunction with the systems 10, 100 generally described herein. Accordingly, the multifilar coil 304 and its application may be best understood with reference to the discussion surrounding FIGS. 2a-c.

In one or more embodiments, the multifilar coil 304 may be made from multiple filaments 302 consecutively and helically wound about a longitudinal axis 306. In the illustrated example, the multifilar coil 304 is quadrafilar, i.e., having four different types, configurations, and/or lengths of filaments 302 wound together as a group, namely, a first filament 302A, a second filament 302B, a third filament 302C, and a fourth filament 308D. The grouping of filaments 302A-D may be consecutively wound in a helical pattern around the longitudinal axis 306. As will be appreciated, however, other embodiments may include more or less than four filaments 302A-D. For instance, the multifilar coil 304 may equally be bifilar, trifilar, or include more than four types or configurations of filaments 302, without departing from the scope of the disclosure.

The filaments 302A-D may be substantially similar to the wire 208 described above with reference to FIG. 2c, such as lengths of wire wound multiple times to form a generally tubular structure. The filaments 302A-D may be made of shape memory materials, such as nitinol. In other embodiments, however, one or more of the filaments 302A-D may be made of metals or metal alloys, such as platinum, and may be coated with one or more medically-effective substances such as, for example, a thrombogenic agent. In yet other embodiments, one or more of the filaments 302 may be made of a biologically-active material. For example, at least one filament 302 may include a fibrin-coated strand to encourage speedier tissue overgrowth, or more speedy or complete clotting at the treatment site. In other embodiments, other filaments 302A-D may be made of biologically-active (e.g., biodegradable, bioerodible, etc.) materials, such as polyglycolic acid (PGA) or polyglycolide, or poly(lactic) acid (PLA) or polylactide or polycaprolactone. One or more of the filaments 302A-D may be made of a combination of materials, for example an alloy of PGA/PLA, intended to facilitate similar goals.

As will be appreciated by those skilled in the art, filaments 302 made of biologically-active materials may be too pliant or soft to form a suitable unifilar coil. However, such materials may be viable components and/or additions to a multifilar coil 304 having one or more other rigid filaments 302 that serve to form a structurally-acceptable coil. The incorporation of a filament 302 made of biologically-active materials may confer suitable biological properties over the length of the multifilar coil 304.

In some embodiments, each of the filaments 302A-D are made of platinum wire. In other embodiments the first, second, and third filaments 302A-C are made of platinum wire, and the fourth filament 302D is made of a PGA, PLA, or PGA/PLA monofilament. In other embodiments, the first, third, and fourth filaments 302A,C,D are made of platinum wire, and the second filament 302B is platinum wire coated with one or more medically-effective substances. In other embodiments, the first, second, and fourth filaments 302A,B,D are made of a nitinol wire, and the third filament 302C is made of a platinum wire. In yet other embodiments, the first and third filaments 302A,C are made of a platinum wire, the second filament 302B is made of nitinol, and the fourth filament 302D is a PGA, PLA, or PGA/PLA monofilament. As will be appreciated, many other configurations of materials for each filament 302A-D may be employed, without departing from the scope of the disclosure.

Moreover, the cross-sectional shape or diameter of each filament 302A-D may be the same or varied when compared with adjacent filaments 302A-D or any of the filaments within the grouping of filaments 302A-D. In other embodiments, however, the filaments 302A-D may be lengths of ribbon having a substantially rectangular cross-sectional shape. In either event, as illustrated, the filaments 302A-D may be consecutively arranged substantially adjacent to each other along the length of the multifilar coil 304. For example, with the exception of the ends of the multifilar coil 304, the first filament 302A generally interposes the fourth and second filaments 302D, 302B, the second filament 302B generally interposes the first and third filaments 302A, 302C, the third filament 302C generally interposes the second and fourth filaments 302B, 302D, and the fourth filament 302D generally interposes the third and first filaments 302C, 302A. Accordingly, the filaments 302A-D are arranged in a repeating A-B-C-D winding pattern along the length of the multifilar coil 304.

Several characteristics of the filaments 304A-D may affect the performance, flexibility, or bendability of the multifilar coil 304. For example, the material, cross-sectional shape, diameter, surface finish, shape, and/or size of each filament 304A-D may be manipulated in order to optimize flexibility of the coil 304. Whether the filament 302A-D has undergone one or more heat treatment processes may also be a factor affecting flexibility. Various cross-sectional shapes of the filaments 302A-D may be used such as, but not limited to, oval, round, star, or polygonal. In some embodiments, these characteristics may be the same or varied in each filament 304A-D in order to achieve a desired flexibility of the multifilar coil 304. Moreover, varying and optimizing these characteristics of the filaments 304A-D may also serve to achieve a desired increase in the axial stretch resistance of the multifilar coil 304, and a reduction in the respective axial bending and buckling resistances of the multifilar coil 304.

The pitch between adjacent filaments 302 may also be varied in order to adjust the flexibility of the multifilar coil 304. As illustrated in FIG. 3, the adjacent filaments 302A-D may be in contact with each other along the length of the multifilar coil 304. In other embodiments, however, the pitch between adjacent filaments 302A-D may be increased such that a gap is formed therebetween. Such an embodiment is generally described in more detail below with respect to FIG. 14. For the purposes of this disclosure, the term "adjacent" does not necessarily mean "contacting," but may mean near but not in biasing engagement. It will be appreciated that multifilar coils may have a increased pitch length as compared to conventional unifilar coils and, therefore, for a given primary wire diameter, may be stiffer than unifilar coils. Also, multifilar coils generally offer additional design flexibility as compared to unifilar coils.

Referring now to FIG. 4a, illustrated is another exemplary multifilar coil 404, according to one or more embodiments. The multifilar coil 404 may be substantially similar to the multifilar coil 304 described above with reference to FIG. 3 and may therefore be best understood with reference to FIG. 3, where like numerals and references refer to like components that will not be described again in detail. The multifilar coil 404 may be characterized generally as a quadrifilar coil that includes two interwound bifilar coils and/or lengths of filaments 302. In particular, the multifilar coil 404 may include an arrangement of the first and second filaments 302A and 302B, respectively, where a plurality 402a of adjacent first filaments 302A is followed by a plurality 402b of adjacent second filaments 302B in a repeating configuration along the length of the multifilar coil 404. It will be appreciated, however, that the multifilar coil 404 may include the use of more than two interwound multifilar filaments 302 and therefore include more than two corresponding and repeating pluralities 402. In one or more embodiments, for example, the multifilar coil 404 may include between about two and about twelve filament 302 types or configurations, without departing from the scope of the disclosure.

As can be appreciated, determining the appropriate number of filaments 302 will have a direct impact on the lateral bending characteristics of the multifilar coil 404, and the other coils and implants described herein. As illustrated, the filaments may be arranged at an angle α with respect to the longitudinal axis 306. Multifilar coils that have lateral bending characteristics that are more coil-like will have filaments arranged at angle α≥45° to the longitudinal axis 306. Multifilar coils that have lateral bending characteristics that are more beam-like, however, will have filaments arranged at angle α<45° to the longitudinal axis 306.

At 45° to the longitudinal axis 306 there is a maximum number of filaments 302 that will fit, shoulder to shoulder, around the perimeter, e.g., circumference, of the coil or implant. This maximum number can be calculated or otherwise derived from the primary coil diameter and the filament diameter. Assuming that all of the filaments 302 are of the same circular diameter, several non-limiting examples of approximate maximum numbers of filaments 302 are presented in Table 1 below.

TABLE 1

| Coil Primary Diameter | Filament Diameter | Max. Filament No. at 45° |
| --- | --- | --- |
| 0.010" | 0.001" | 19.99 |
| 0.010" | 0.0015" | 12.58 |
| 0.010" | 0.002" | 8.88 |
| 0.010" | 0.0025" | 6.66 |
| 0.014" | 0.0015" | 18.51 |
| 0.014" | 0.002" | 13.32 |
| 0.014" | 0.0025" | 10.21 |
| 0.018" | 0.0015" | 24.43 |
| 0.018" | 0.002" | 17.77 |
| 0.018" | 0.0025" | 13.77 |
| 0.018" | 0.003" | 11.10 |
| 0.035" | 0.0015" | 49.59 |
| 0.035" | 0.0018" | 40.96 |
| 0.035" | 0.002" | 36.64 |
| 0.035" | 0.0025" | 28.87 |
| 0.035" | 0.003" | 23.69 |

In embodiments where the resulting calculation determines that a fractional number of filaments 302 is appropriate for a 45° angle to the longitudinal axis 306, the coil designer has several choices: a) round the number of filaments 30 to the integer below, thereby reducing the coil primary diameter; b) round the number of filaments 302 to the integer below and also increase the filament diameter in order to preserve the coil primary diameter; c) round the number of filaments 302 to the integer above, thereby increasing the coil primary diameter; and d) round the number of filaments 302 to the integer above and reduce the filament diameter in order to preserve the coil primary diameter. It will be appreciated that filaments 302 having differing diameters from one to another and non-circular cross sectional shapes may also be used, without departing from the scope of the disclosure. The number of such filaments 302 may be calculated according to the principles discussed herein for circular cross-section filaments 302.

As illustrated, the first plurality 402a may include two consecutive and adjacent loops or coils of first filaments 302A, and the second plurality 402b may include two consecutive and adjacent loops or coils of second filaments 302B. Accordingly, the filaments 302A-B may be arranged in a repeating A-A-B-B loop or winding pattern along the length of the multifilar coil 404, and the pluralities 402a,b correspondingly repeat this pattern contiguously. It will be appreciated that more than two windings of each filament 302A-B may be included in each plurality 402a,b, respectively, without departing from the scope of the disclosure. Moreover, in some embodiments, at least one of the pluralities 402a,b may include a solitary filament 302 while the other plurality includes a solitary filament or multiple filaments 302.

Embodiments contemplated herein further include more than two pluralities 402a,b of adjacent filaments 302 extending contiguously and repeating along the length of the multifilar coil 404. For example, embodiments are contemplated where there are continuous pluralities 402 of adjacent filaments 302 that include multiple loops or windings of each of the filaments 302A-D (FIG. 3) disclosed herein, or additional filaments not particularly disclosed herein. As a result, there is practically no limit to the possible plurality combinations or loop patterns that may be arranged along the length of the multifilar coil 404.

In some embodiments, the first filaments 302A may exhibit a substantially equal first filament lateral flexibility and at least two of the second filaments 302B may have a second lateral flexibility. As used herein, "lateral flexibility" may refer to a relative bendability of a filament away from its longitudinal axis and may also include a relative bendability of one or more helically wound filaments as they bend away from a central longitudinal axis of a helically wound coil made of the one or more filaments. Lateral flexibility may be tested, for example, by standard tests such as a 3-point bending test. The first filaments 302A may exhibit a different flexibility or bendability when compared with the second filaments 302B. For example, the first filament lateral flexibility of the first filaments 302A may be different than the second filament lateral flexibility of the second filaments 302B, such that the second filament lateral flexibility is less than the first filament lateral flexibility. As described above, the respective flexibilities may be at least partially based on several factors including, but not limited to, the diameter of the filament 302A-B, the material composition of the filament 302A-B, whether the filament 302A-B has undergone heat treatment, etc. As a result, the first filament lateral flexibility of the first filaments 302A may be greater than the second filament lateral flexibility of the second filaments 302B, such as by about two times greater, about three times greater, about five times greater, or about ten times greater. In some embodiments, as shown below, the first filament lateral flexibility of the first filaments 302A may be greater than the second filament lateral flexibility of the second filaments 302B by about 50×, 100×, 500×, 1000×, 2000×, or more than 2000× the second filament flexibility. As will be appreciated, however, the differences in respective filament lateral flexibilities may be adjusted or otherwise designed to meet specific application parameters and are not to be limited to only the multiples disclosed herein.

In some embodiments, a useful index or formula that may be used to determine filament flexibility is E*I, where E is the Young's Modulus of the filament material, I is the second moment of area of the particular filament 302, and E*I is the mathematical product of the two. For example, the Young's Modulus for various materials is tabulated below in Table 2:

TABLE 2

| Material | Young's Modulus, E (GPa) |
| --- | --- |
| Gold | 78 |
| Nitinol (Austenitic) | 75-83 |
| Platinum | 168 |
| Tungsten | 411 |

TABLE 2-continued

| Material | Young's Modulus, E (GPa) |
|---|---|
| Tantalum | 186 |
| Stainless Steel | 199 |
| PGA | 0.24 |
| PLA | 0.35-2.8 |
| Polycaprolactone | 0.3 |
| Polyester | 3 |

The filament flexibilities of two filaments can be compared using the formula $(E_1*I_1)/(E_2*I_2)$; where $E_1$ and $E_2$ are the corresponding Young's Modulus for the first and second filaments, respectively, and $I_1$ and $I_2$ are the second moment of area for the first and second filaments, respectively.

In embodiments where the two filaments have the same cross-sectional shape and size, then they will have the same second moment of area. If the two filaments are made of different materials then the two wires will exhibit different moduli, and the comparative expression would be reduced to $E_1/E_2$. Accordingly, using this expression, platinum has a filament flexibility that is 700 times less (168/0.24) than that of PGA. Similarly, tungsten has a filament flexibility that is 2.4 times less (411/168) than that of platinum. If the two filaments have a different cross-sectional shape and/or size then the second moment of area in lateral bending will need to be calculated for each of the two filaments, and the results can be entered into the equation above.

As a result of the differences in filament lateral flexibilities in the filaments 302A-B, each plurality 402a,b may correspondingly provide a distinct region along the length of the multifilar coil 404 that exhibits a discrete flexibility analogous to the filament lateral flexibility of its respective component filaments 302A-B. For example, a first region 406a along the length of the multifilar coil 404 may be a helically wound region that is defined by at least a portion of the helically wound first filaments 302A, and this first region 406a may exhibit a first coil flexibility over the axial length corresponding to the first region 406a, or the first region's 406a helical axial length. A second region 406b, juxtaposed adjacent the first region 406a, may be a helically wound region that is defined by at least a portion of the helically wound second filaments 302B, and this second region 406b may exhibit a second coil flexibility over the axial length corresponding to the second region 406b. The first and second regions 406a,b may be sized substantially equally, e.g., having substantially equal length, along the long axis of the coil 404. In some embodiments, the regions 406a,b may have the same number of filaments having the same diameter, or regions 406a,b may have different numbers of filaments and/or different diameters. But in other embodiments, the first and second regions 406a,b may be sized differently along the length of the coil 404. For example, the lengths and/or diameters of the regions 406a,b can be different from each other, and/or the numbers of filaments employed may be different.

In some embodiments, the first coil flexibility corresponding to the first region 406a may be greater than the second coil flexibility corresponding to the second region 406b, depending on the characteristics of the filaments 302A,B, and thereby permitting the helically wound first region 406a to bend or flex to a greater degree than the helically wound second region 406b. In one or more embodiments, the first coil flexibility may be greater than the second coil flexibility, such as by about two times greater, about three times greater, about five times greater, or about ten times greater. As a result, the helical axial length of the first region 406a may have a greater tendency to bend or flex than the helical axial length of the second region 406b when a force is applied to the coil 404. Consequently, the coil will have a direction of easy lateral bending, along the helical axial length, that corresponds to a radial direction from the axis toward the first pluralities 2006a.

Referring now to FIG. 4b, with continued reference to FIG. 4a, illustrated is a cross-sectional view of the multifilar coil 404, according to one or more embodiments. As illustrated, the multifilar coil 404 may include a series of contiguous first and second pluralities 402a,b spanning a portion of the axial length of the coil 404, and thereby providing a corresponding series of first and second coil regions 406a,b, respectively. Moreover, each of the first and second pluralities 402a,b may include three adjacent filaments 302A,B, respectively. A force 408 applied to the multifilar coil 404 will cause the coil 404 to bend or flex. In some embodiments, the force 408 is a lateral force applied normal to the longitudinal axis 306, thereby forcing the multifilar coil 404 to bend in a first direction 410 and result in a generally convex radial portion 412a and a generally concave radial portion 412b.

As a result of the increased filament lateral flexibility of the first filament(s) 302A in the first pluralities 402a with respect to the filament lateral flexibility of the second filament(s) 302B in the second pluralities 402b, the first regions 402a in the concave portion 412b will preferentially bend or flex (in torsion) before the second regions 402b bend or flex. As the coil 404 bends in the first direction 410, the adjacent filaments 302A begin to separate from each other by a first distance 414 in the convex portion 412a. Moreover, adjacent filaments 302A,B in adjacent first and second pluralities 402a,b, respectively, may also begin to separate from each other by a second distance 416. In some embodiments, the second distance 416 may be less than the first distance 414. In yet other embodiments, as the coil 404 bends in the first direction 410, adjacent filaments 302B in an adjacent second plurality 402b may begin to separate from each other by a third distance 418, where the third distance 418 may be less than the first distance 414 and may be less than the second distance 416.

Referring again to FIG. 4a, the multifilar coil 404 may include a proximal end region 404a and a distal end region 404b. In one or more embodiments, the proximal end region 404a couples to a delivery device (not shown), such as the positioner 40 in conjunction with the implant interface 80 described above with reference to FIGS. 2a-c, or other devices known in the art or otherwise described herein.

Referring now to FIG. 5, illustrated is another exemplary multifilar coil 504, according to one or more embodiments. The multifilar coil 504 may be substantially similar to the multifilar coils 304 and 404 described above with reference to FIGS. 3 and 4, respectively and therefore may be best understood with reference to FIGS. 3 and 4, where like numerals and references refer to like components that will not be described again. As illustrated, the multifilar coil 504 may be formed from multiple filaments 302A-D wrapped helically about the longitudinal axis 306. As with prior embodiments, more or less than the four distinct filaments 302A-D shown in FIG. 5 may be employed, without departing from the scope of the disclosure.

The multifilar coil 504 may include multiple bending regions extending along the length of the coil 504. For example, the multifilar coil 504 may include a first bending region 502a, a second bending region 502b, a third bending region 502c, and a fourth bending region 502d. The first bending region 502a may include one or more loops formed from each of the first, second, third, and fourth filaments 302A-D contiguously arranged and repeating a predetermined loop pattern, such as A-B-C-D. It will be appreciated that several variations in the number of filaments 302A-D and corresponding loops or windings may be included in the first bending region 502a. Moreover, the loop pattern resulting from the combination of filaments 302A-D may be repeated multiple times, without departing from the scope of the disclosure. Moreover, the pitch between adjacent filaments 302A-D may be manipulated (e.g., increased or decreased) so as to adjust or otherwise optimize the bendability or flexibility across the first bending region 502a.

In at least one embodiment, one or more of the filaments 302A-D in the first bending region 502a may terminate distally and thereafter cease to wind contiguously with the remaining filaments 302A-D. For example, as illustrated in FIG. 5, the fourth filament 302D may terminate at the distal end of the first bending region 502a and as a result is not present thereafter in the second, third, or fourth bending regions 502b-d, but instead leaves a gap 506 between the first and second bending regions 502a,b and in subsequent bending regions, such as between the second and third bending regions 502b,c.

Since the fourth filament 302D terminates at the distal end of the first bending region 502a, the second bending region 502b may include one or more loops formed from each of the first, second, and third filaments 302A-C contiguously arranged and repeating a predetermined loop pattern, such as A-B-C. While only one occurrence of the loop pattern A-B-C is depicted in FIG. 5, it will be appreciated that the loop pattern A-B-C may be repeated multiple times within the second bending region 502b. As a result, the gap 506 formed by the termination of the fourth filament 302D may also be repeated a corresponding number of times within the second bending region 502b, while the pitch of the remaining filaments 302A-C remains constant.

In some embodiments, one or more of the filaments 302A-C in the second bending region 502b may terminate at the distal end of 502b and thereafter cease to wind contiguously with the remaining filaments 302A&C. For example, the second filament 302B may be configured to terminate at the distal end of the second bending region 502b and thereafter is not present in the third or fourth bending regions 502c,d but instead leaves one or more gaps 508. As a result, the third bending region 502c may include one or more loops formed from each of the first and third filaments 302A,C contiguously arranged and repeating a predetermined loop pattern A-C-A-C, while the pitch of the first and third filaments 302A,C remains constant.

As illustrated in FIG. 5, the third filament 302C terminates at the distal end of the third bending region 502c, such that the fourth bending region 502d is formed by a monofilament loop of the first filament 302A. Termination of the third filament 302C results in the formation of one or more gaps 510 being formed contiguously with the gaps 506 and 508 formed by the termination of the fourth and second filaments 302D and 302B, respectively. While only one loop of the first filament 302A is depicted in the fourth bending region 502d, it will be appreciated that several first filament 302A loops or windings may be repeated multiple times within the fourth bending region 502d, without departing from the scope of the disclosure. In another embodiment one or more of the gaps 506, 508, 510 can be reduced in width or can be eliminated by axially compressing the coil 504. In such an embodiment of the coil 504 having no gaps, the filaments 302A-D may be in contact with or substantially adjacent to each other.

Referring now to FIG. 6, illustrated is an exemplary coiled implant 604, according to one or more embodiments disclosed. The coiled implant 604 may be similar in some respects to the implant 95 disclosed in FIGS. 2a-2c and the multifilar coils 304, 404, and 504 disclosed in FIGS. 4a, 4b, and 5, respectively. Accordingly, the coiled implant 604 may be best understood with reference to FIGS. 2a-5, where like numerals and references correspond to like components that will not be described again.

As illustrated, the coiled implant 604 may include an outer coil 602 and an inner coil 606, where the inner coil 606 may be at least partially nested within the outer coil 602 and concentric therewith about the longitudinal axis 306. In some embodiments, the outer coil 602 may be characterized as a multifilar coil, having at least two distinct filaments 302, such as first and second filaments 302A,B, extending helically about the longitudinal axis 306 along the length of the outer coil 602. In other embodiments, however, the outer coil 602 may be characterized as an unifilar coil having a solitary monofilament or may include more than two filaments 302A, B. The first and second filaments 302A,B may be made of the same or different materials or otherwise exhibit the same or different structural characteristics, as described above. As a result, the first and second filaments 302A,B may exhibit the same or different filament lateral flexibilities or stiffness. For example, in at least one embodiment, the first filament 302A may be more rigid or stiff than the second filament 302B, but in other embodiments, the second filament 302B may be more rigid than the first filament 302A.

The pitch between adjacent loops or filaments 302A,B may also affect the flexibility of the outer coil 602. While the filaments 302A,B are depicted in FIG. 6 as being in close contact one with another, embodiments contemplated herein include a greater pitch between adjacent filament 302A,B loops or windings. In some embodiments, the pitch of the inner coil 606 is sufficiently different relative to the pitch of the outer coil 602 such that the turns of the outer coil 602 are substantially prevented from radially slipping past one another and into the volume enclosed by the outer coil 602. In order to provide this functionality, the inner coil 606 may be wound in a more axial direction than the winding direction of the outer coil 602, otherwise the turns of the outer coil 602 may risk radially slipping in between the turns of the inner coil 606. In one or more embodiments, this can be accomplished where the pitch of the inner coil 606 is at least 2 times more (e.g., 3 times, 4 times, 5 times, 6 times, etc.) than the pitch of the outer coil 602. Accordingly, one turn of an inner coil 606 filament (e.g., filament 302C) may be configured to span several outer coil 602 filaments 302A,B, and they will cross at sufficient non-parallel angles to prevent or reduce the likelihood of radial passage of the outer coil 602 filament 302A,B into the volume enclosed by the outer coil 602.

It will be appreciated that more than two filaments 302A,B may be used in the outer coil 602, without departing from the scope of the disclosure. And while the first and second filaments 302A,B are depicted as alternating single loops along the length of the outer coil 602, it will further be appreciated that the filaments 302A,B may be arranged into groupings or pluralities, such as the pluralities 406a,b described above with reference to FIGS. 4a and 4b. Specifically, the outer coil 602 may be configured to bend in a manner substantially similar to the coil 404, as described above with reference to FIG. 4b where the outer coil 602 has regions of varying flexibilities that permit bending relative to the long axis to different degrees, depending on the lateral filament flexibility of the filaments 302 spanning the regions.

In some embodiments, the inner coil 606 may be characterized as a unifilar coil made of a single filament 302, such as the third filament 302C, wound helically about the longitudinal axis 306. As will be appreciated, however, the inner coil 606 may equally be characterized as a multifilar coil having more than one type or configuration of filament 302 forming contiguous or alternating windings along the longitudinal axis 306. The inner coil 606 may include a first region 608a and a second region 608b. The first region 608a may be arranged substantially outside of the outer coil 602 and the second region 608b may be arranged substantially inside the outer coil 602.

In one or more embodiments, the pitch between adjacent windings of the filament 302C may be substantially the same across the length of the inner coil 606. In some embodiments, however, the pitch between adjacent windings of the filament 302C in the first region 608a may be different than the pitch between adjacent windings in the second region 608b. For example, the windings of the filament 302C in the second region 608b may have a pitch that results in the formation of a gap 610 between each adjacent winding. Depending on the application, the width of the gap 610 may be varied. In some embodiments, for instance, the width of the gap 610 may be about 20% of the width of the third filament 302C. In other embodiments, the width of the gap 610 may be about 40%, about 60%, about 80%, about 100%, about 150%, or about 200% of the width of the third filament 302C. In yet other embodiments, the pitch or gap 610 of the inner coil 606 may be at least twice the pitch of the outer coil 602.

In one or more embodiments, the inner coil 606 biases the inner surface of the outer coil 602 across the second region 608b. Mutual engagement between the inner surface of the outer coil 602 and the outer surface of the inner coil 606 may provide several advantages. For example, mutual engagement may allow for or otherwise provide a torquable coil 604. Furthermore, mutual engagement may also prevent radial coil slippage and also provide a helically changing direction of easier lateral bending. In some embodiments, the inner coil 606 is dextrorotary and the outer coil 602 is levorotary. In other embodiments, the inner coil 606 is levorotary and the outer coil 602 is dextrorotary.

It is also contemplated herein to have more than one inner coil 606 arranged within the outer coil 602. For example, one or more inner coils 606 may be arranged with the outer coil 602 such that one inner coil 606 is partially nested within one end of the outer coil 602 and another inner coil 606 is partially nested within the opposing end of the outer coil 602. In yet other embodiments, the inner coil 606 may have another inner coil (not shown) arranged at least partially within the inner coil 606. It will be appreciated that the inner coil 606 may be formed in various configurations including, but not limited to, those described herein below, especially in FIGS. 7-17 and 20a-d.

Figure 7C:
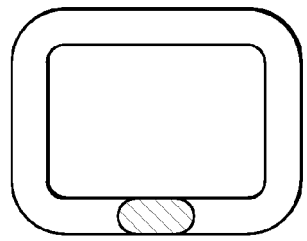
FIGS. 7a, 7b, and 7c illustrate cross-sectional views of exemplary filament winding shapes, according to one or more embodiments disclosed.
Figure 7B:
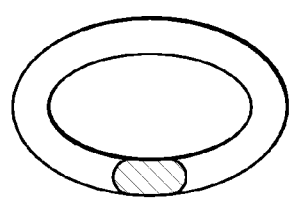
Figure 7A:
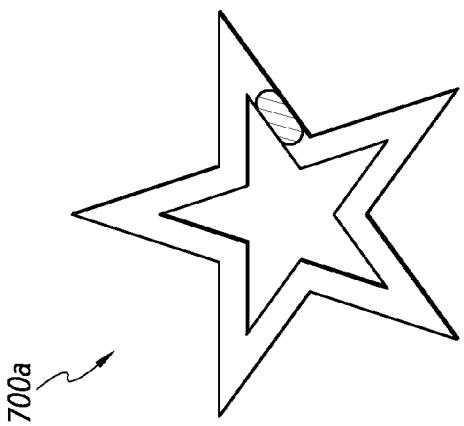

Referring now to FIGS. 7a, 7b, and 7c, illustrated are exemplary filament winding shapes, according to one or more embodiments disclosed. Specifically, FIG. 7a depicts a star filament winding shape 700a, FIG. 7b depicts a generally oval filament winding shape 700b, and FIG. 7c depicts a generally rectangular filament winding shape 700c. Each filament winding shape 700a-c may be generally orthogonal to the longitudinal axis 306 (FIG. 3) and indicative of the cross-sectional tubular shape that one or more of the coil implants 95, 604 or multifilar coils 304, 404, 504, or any of the other implants or coils generally described herein, may exhibit. As will be appreciated, however, the filament winding shapes 700a-c are shown merely by example, and should not be considered as the only filament winding shapes contemplated. In alternative embodiments, for example, any rounded, polygonal, combination rounded/polygonal, or multi-faceted shape may be used as a filament winding shape, without departing from the scope of the disclosure. Exemplary filament winding shapes may include, but are not limited to, triangular shapes, curved shapes, circular shapes, oval shapes, elliptical shapes, combinations thereof, or the like.

Different filament winding shapes 700a-c provide corresponding different advantages to the application requiring the use of coil implants 95, 604 and/or multifilar coils 304, 404, 504. For example, the star filament winding shape 700a is formed in the general shape of a five-pointed star. Operating as an aneurysm coil, for instance, the coil implant 95, 604 and/or multifilar coil 304, 404, 504 exhibiting the star filament winding shape 700a may be able to provide more material within a given diameter, and as a result there will be greater volume filling of the aneurysm for a given primary diameter of the filament used. Moreover, the star filament winding shape 700a uses more filament wire length per unit length as compared to other filament winding shapes, which translates into more softness along the axial length of the coil implant 95, 604 and/or multifilar coil 304, 404, 504.

Figure 8:
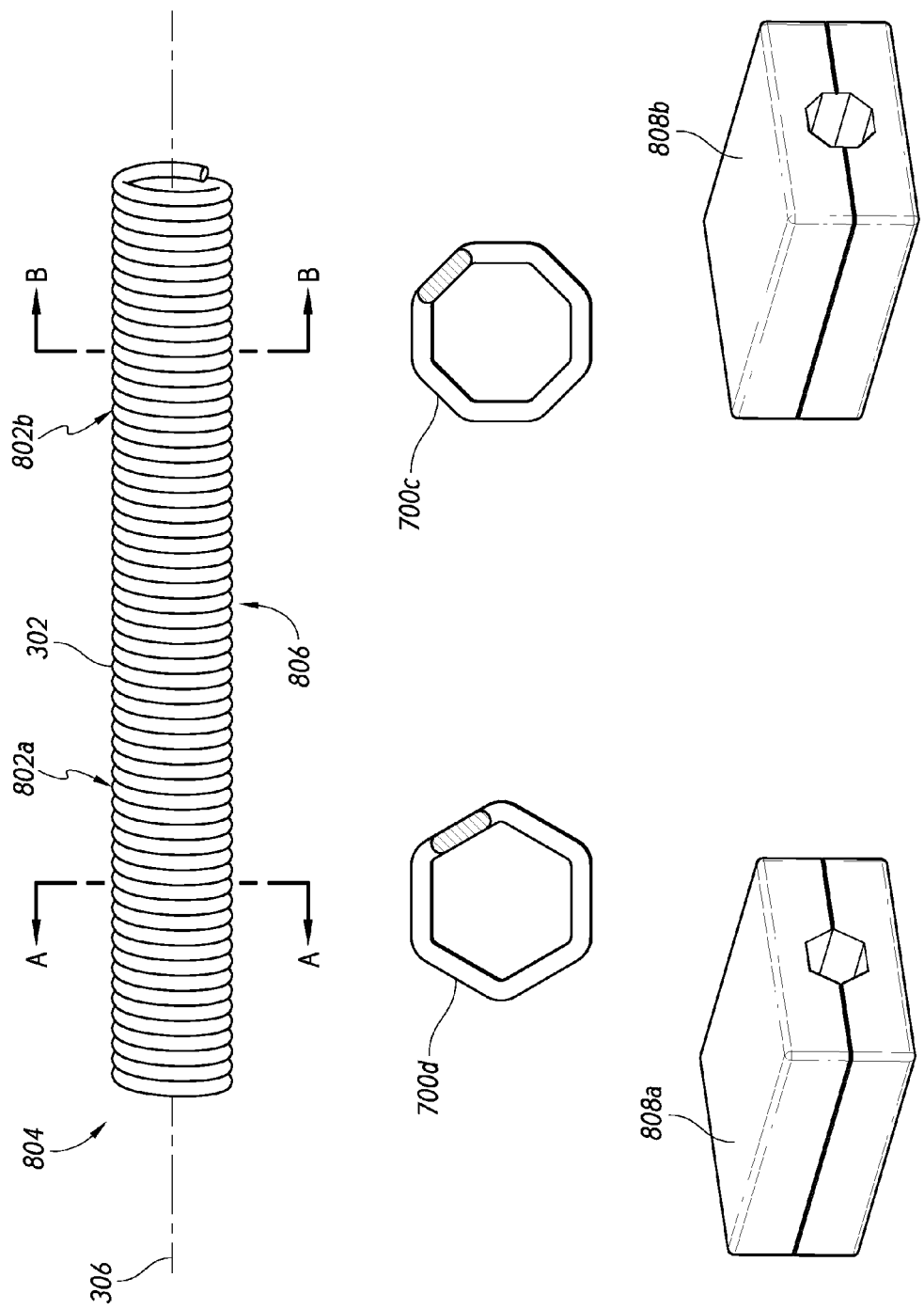
FIG. 8 illustrates side and cross sectional views of an exemplary coil that exhibit two or more filament winding shapes along its axial length, and corresponding crimping dies to make the filament winding shapes, according to one or more embodiments of the disclosure.

Referring to FIG. 8, with continued reference to FIGS. 7a-7c, illustrated is an exemplary coil 804 that may exhibit or otherwise provide two or more filament winding shapes along its axial length, according to one or more embodiments of the disclosure. The coil 804 may be substantially similar to, or at least exemplary of, one or more of the coil implants 95, 604 and/or multifilar coils 304, 404, 504 described herein. Accordingly, the following description equally applies to the coil implants 95, 604 and/or multifilar coils 304, 404, 504, or any of the subsequently described implants and coils, where like numerals represent like components that will not be described again. The coil 804 may be formed by a plurality of windings of one or more filaments 302 about the longitudinal axis 306. In one embodiment, the coil 804 may define a first segment 802a and a second segment 802b. The first and second segments 802a,b may be spaced apart along the longitudinal axis 306, but may nonetheless be contiguously connected as integral portions of the coil 804. As will be appreciated, the coil 804 may include more than two segments 802a,b, without departing from the scope of the disclosure.

The first segment 802a may have a filament winding shape that is different than the filament winding shape of the second segment 802b. Specifically, the first segment 802a may define a first filament winding shape 700d and the second segment 802b may define a second filament winding shape 700e. In the illustrated example, the first filament winding shape 700d is formed in a generally hexagonal shape, as shown taken along lines A-A, and the second filament winding shape 700e is formed in a generally octagonal shape, as shown taken along lines B-B. The first filament winding shape 700d may transition to the second filament winding shape 700e at a central point or location 806 along the length of the coil 804 such that the windings or loops of the filament 302 axially continue uninterrupted along the length of the coil 804. The location 806 of transition may be varied to fit any particular application. In at least one embodiment, the second filament winding 700e may be different than the first filament winding shape 700d, irrespective of the angular orientation about the longitudinal axis 306 of the first filament winding shape 700d with respect to the second filament winding shape 700e, and irrespective of the relative sizes of the first and second filament winding shapes 700d,e.

The respective profiles of each of the filament winding shapes 700a-e may be formed in various ways. In one embodiment, for example, the shapes may be formed by winding the filament 302 using a mandrel-less winder (not shown). In other embodiments, however, the shape may be achieved by crimping the filaments 302 using, for example, a crimping die. As shown in FIG. 8, the first filament winding shape 700d may be formed by crimping the filament 302 of the first segment 802a using a first crimping die 808a, which corresponds to the desired filament shape over the first segment 802a (e.g., hexagonal). The second filament winding shape 700e may be formed by crimping the filament 302 of the second segment 802b using a second crimping die 808b, which corresponds to the desired filament shape over the second segment 802b (e.g., octagonal). In some embodiments, the crimping dies 808a,b are used in conjunction with heat treatment techniques in order to ensure a properly formed filament winding shape 700a-e. In other embodiments, the dies 808a,b may be applied randomly or otherwise used at various discrete points along the length of the coil 804 in order to form varying segments of shaped filaments 302.

As can be appreciated, varying the filament winding shapes 700a-e along the length of the coil 804 may result in a varied lateral flexibility of the coil 804. In other words, the overall flexibility of the coil 804 may be manipulated in the axial direction depending on the specific filament winding shape 700a-e used or otherwise applied. In some embodiments, the filament winding shapes 700a-e may be continuously variable along the length of the coil 804.

Figure 9:
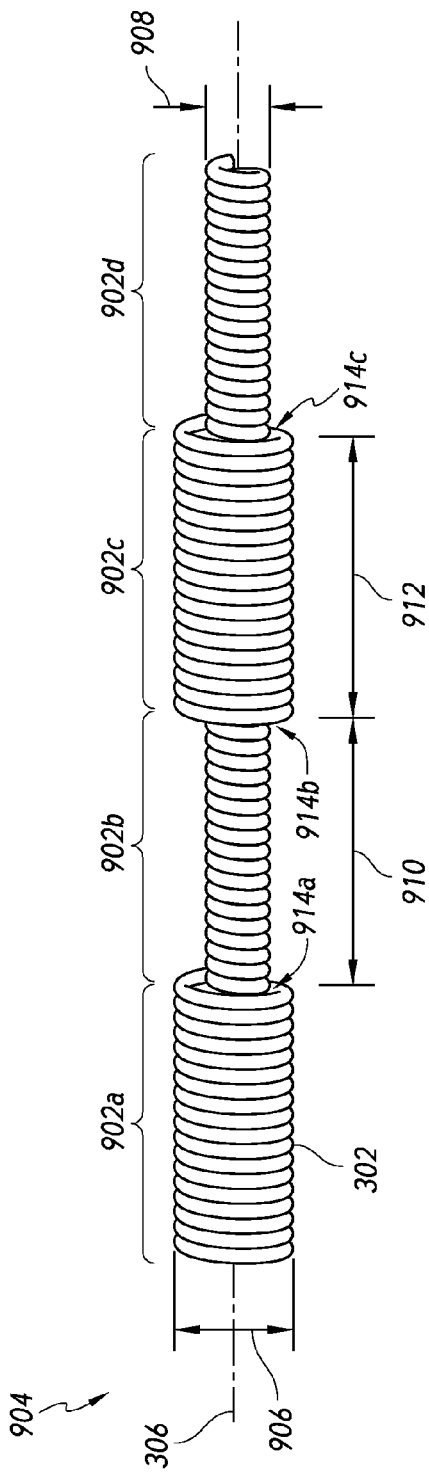
FIG. 9 illustrates a side view of another exemplary coil that may be used in conjunction with the system of FIG. 2a or 2b, in accordance with various embodiments of the subject technology.

Referring now to FIG. 9, illustrated is another exemplary coil 904 that may be used in conjunction with the systems 10, 100 (FIGS. 2a-c), according to one or more embodiments. The coil 904 may be substantially similar to, or at least exemplary of, one or more of the coil implants 95, 604 and/or coils 304, 404, 504, 804 described herein. Accordingly, the following description equally applies to the various embodiments of coil implants 95, 604 and/or multifilar coils 304, 404, 504, 804 described herein, or any of the subsequently described implants and coils. Moreover, like numerals and references used from prior figures will not be described again in detail. The coil 904 may be formed by a plurality of windings of one or more filaments 302 about the longitudinal axis 306. The filaments 302 may be wound singularly, in duplicate, triplicate, etc., or in groupings or pluralities as described above with reference to FIG. 4a, without departing from the scope of the disclosure.

As illustrated, the coil 904 may include one or more regions having varying cross-sectional diameters. Specifically, the coil 904 may include a first region 902a, a second region 902b, a third region 902c, and a fourth region 902d axially-spaced along the length of the coil 904. In one or more embodiments, the regions 902a-d are contiguous portions of the coil 904, such that the windings or loops of the filament 302 axially continue uninterrupted along the length of the coil 904. The regions 902a-d form a pattern that may be repeated along the length of the coil 904. In particular, the repeating pattern may include a larger diameter region, such as the first or third regions 902a,c, followed by a smaller diameter region, such as the second or fourth regions 902b,d, and repeated multiple times to a desired coil 904 length.

The first region 902a may exhibit a first cross-sectional diameter 906 and the fourth region 902d may exhibit a second cross-sectional diameter 908. In some embodiments, the third region 902c may also exhibit the first cross-sectional diameter 906 and the second region 902b may also exhibit the second cross-sectional diameter 908. In other embodiments, however, the respective cross-sectional diameters for the first and third regions 902a,c may be different, and the respective cross-sectional diameters for the second and fourth regions 902b,d may be different. In either case, however, the cross-sectional diameters for the first and third regions 902a,c may be greater than the cross-sectional diameters for the second and fourth regions 902b,d. As can be appreciated, several variations in the respective cross-sectional diameters for each region 902a-d are possible, without departing from the scope of the disclosure.

Each region 902a-d may also exhibit a respective axial length. For example, the second region 902b may exhibit a first axial length 910 and the third region 902c may exhibit a second axial length 912. In some embodiments, the first and fourth regions 902a,d may also exhibit either the first or second axial lengths 910, 912, but in other embodiments, the first and fourth regions 902a,d may exhibit respective axial lengths that are different than either the first or second axial lengths 910, 912, and either the same or different from each other. As can be appreciated, several variations in respective axial lengths for each region 902a-d are possible, without departing from the scope of the disclosure.

Since the cross sectional diameter of the first region 902a is greater than the cross-sectional diameter of the second region 902b, a transition region 914a is defined therebetween. Similar transition regions 914b, 914c may be defined at the transitional interface between the second region 902b and the third region 902c, and between the third region 902c and the fourth region 902d, respectively. In the illustrated embodiment, each transition region 914a-c may provide an abrupt or sudden transition from either the first cross-sectional diameter 906 to the second cross-sectional diameter 908, or from the second cross-sectional diameter 908 to the first the cross-sectional diameter 906. The abrupt transition of each transition region 914a-c may occur over an axial length spanning one or two or more windings of the filament 302. As a result, the abrupt transition may be considered a step-wise transition in some applications.

In some embodiments, the transition regions 914a-c may be configured to provide an added amount of softness or flexibility to the coil 904 along its axial length. The transition regions 914a-c may also provide break points where the coil 904 may be segmented for use at the proposed treatment site. In some embodiments, the larger-diameter regions along the length of the coil 904, such as the first and third regions 902a,c, may be configured to provide the break points in the coil 904, and the smaller diameter regions along the length of the coil 904, such as the second and fourth regions 902b,d, may be configured to find spaces to fill within the volume of the deployed coil 904. Moreover, it will be appreciated that the pitch of the coil 904 may be constant or varied along its entire length, depending on the application, in order to vary the overall flexibility of the coil 904.

In one or more embodiments, the coil 904 may further be able to provide an added amount of axial flexibility apart from the lateral flexibility exhibited. For example, the respective diameters for the first and third regions 902a,c may be sufficiently large to be able to at least partially receive the second and fourth regions 902b,d, respectively, therein. As a result, in the event the coil 904 is axially compressed, the second and fourth regions 902b,d may be able to be axially pressed a distance into the respective inner lumens defined by the first and third regions 902a,c.

Figure 10:
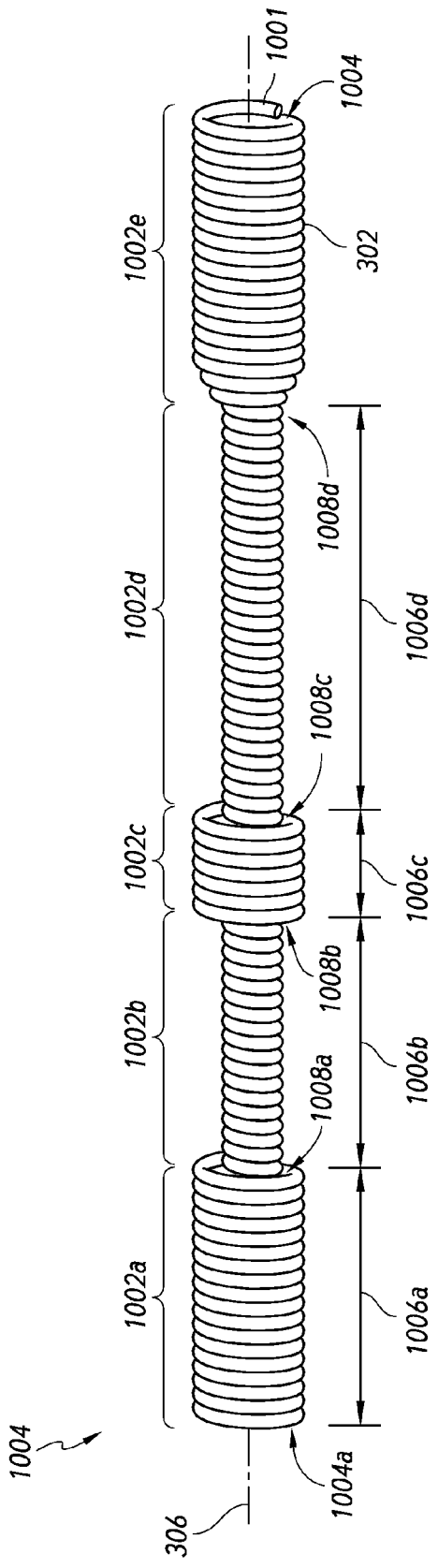
FIG. 10 illustrates a side view of another exemplary coil that may be used in conjunction with the system of FIG. 2a or 2b, in accordance with various embodiments of the subject technology.

Referring now to FIG. 10, illustrated is another exemplary coil 1004 that may be used in conjunction with the systems 10, 100, according to one or more embodiments. The coil 1004 may be similar in some respects to the coil 904 described above in FIG. 9 and therefore may be best understood with reference to FIG. 9, where like numerals represent like components that will not be described again in detail. Similar to the coil 904 described above, the coil 1004 may be formed by a plurality of windings of one or more filaments 302 about the longitudinal axis 306, and may define one or more regions having varying cross-sectional diameters. Specifically, the coil 1004 may include a first region 1002a, a second region 1002b, a third region 1002c, a fourth region 1002d, and a fifth region 1002e, where each region 1002a-e is axially-spaced along the length of the coil 1004 and exhibits the same or differing cross-sectional diameters. In one or more embodiments, the regions 1002a-e are contiguous portions of the coil 1004, such that the windings or loops of the filament 302 axially continue uninterrupted along the length of the coil 1004.

The coil 1004 may have a proximal side 1004a and a distal side 1004b. As depicted, the distal side 1004b may be the distal end or tip of the coil 1004, and the distal end 1001 of the filament 302 may be turned into the interior of the coil 1004. Alternatively, the side 1004b may be the proximal end of the coil 1004.

Also similar to the coil 904, each region 1002a-e in the coil 1004 may exhibit an axial length, such as a first axial length 1006a as exhibited by the first region 1002a, a second axial length 1006b as exhibited by the second region 1002b, a third axial length 1006c as exhibited by the third region 1002c, and a fourth axial length 1006d as exhibited by the fourth region 1002d. As illustrated, the respective axial lengths 1006a-d may be varied. In other embodiments, however, one or more of the axial lengths 1006a-d may be same or substantially the same. Again, as can be appreciated, several variations in respective axial lengths 1006a-d for each region 1002a-e are possible, without departing from the scope of the disclosure.

The coil 1004 may further define transition regions 1008a, 1008b, 1008c, and 1008d between the first and second regions 1002a,b, between the second and third regions 1002b,c, between the third and fourth regions 1002c,d, and between the fourth and fifth regions 1002d,e, respectively. Similar to the transition regions 914a-c described above with reference to FIG. 9, the transition regions 1008a-c may be characterized as abrupt transition regions where the cross-sectional diameter of one of the regions 1002a-d suddenly changes to a smaller or larger cross-sectional diameter of an adjacent region 1002a-d. The transition region 1008d between the fourth and fifth regions 1002d,e, however, may provide a tapering or gradual transition between adjacent regions 1002d,e.

Referring now to FIGS. 11a and 11b, with continued reference to FIG. 10, illustrated are exemplary transition regions 1102a (FIG. 11a) and 1102b (FIG. 11b) along the length of a coil 1104, according to one or more embodiments. The transition regions 1102a,b may be somewhat similar to the transition region 1008d of FIG. 10 in that there is a tapering or otherwise gradual transition from one region to another along the length of the coil 1104. Specifically, the transition regions 1102a,b provide a tapering transition from a proximal region 1106a to a middle region 1106b formed on the coil 1104. It will be appreciated, however, that the transition regions 1102a,b may be formed between any region on the coil 1104, without departing from the scope of the disclosure. For example, the tapering regions 1102a,b may be formed between the middle region 1106b and an adjacent distal region 1106c. In other embodiments, the tapering regions 1102a,b may be formed on a distal end portion of the coil 1104 or a proximal end portion of the coil 1104, in one example thereby tapering one or more ends of the coil 1104 to a generally closed configuration. In yet other embodiments, opposing tapering regions 1102a,b may be arranged throughout middle portions 1106b of the coil 1104 along its length, thereby providing an undulating middle portion 1106b.

In FIG. 11a, the transition region 1102a may extend over or otherwise span a first axial distance 1110a along the length of the coil 1104. In FIG. 11b, the transition region 1102b may extend over or otherwise span a second axial distance 1110b along the length of the coil 1104. As depicted, the first and second axial distances 1110a,b may be different. For example, the first transition region 1102a may taper across the axial span of approximately two filament 302 windings or otherwise over at least two 360° turns of the winding. In contrast, the second transition region 1102b may be configured to provide a gradual transition that spans across at least three filament 302 windings or otherwise over at least three 360° turns of the winding. Accordingly, the second axial distance 1110b will generally be greater than the first axial distance 1110a, assuming the same size of filament 302 is used to form the coils 1104.

In some embodiments, the tapering transition spanning the transition regions 1102a,b may be generally linear. In other embodiments, however, the tapering transition spanning the transition regions 1102a,b may be generally non-linear, such as, but not limited to, following an exponential, quadratic, or square root function as it tapers between the adjacent regions 1106a,b. In at least one embodiment, one or both of the transition regions 1102a,b may taper over an extended length of the coil 1104, such as over a fourth, a third, or half of the entire axial length of the coil 1104. In yet further embodiments, the transition regions 1102a,b may include at least one step-wise change (not shown) across the axial length 1106a,b.

Referring now to FIG. 12, illustrated is another exemplary coil 1204 that may be used in conjunction with the systems 10, 100 (FIGS. 2a-c), according to one or more embodiments. The coil 1204 may be similar in some respects to the coil 904 described above with reference to FIG. 9. Accordingly, the coil 1204 may be best understood with reference to FIG. 9, where like numerals represent like components that will not be described again in detail. Similar to the coil 904 described above, the coil 1204 may be formed by a plurality of windings of one or more filaments 302 about the longitudinal axis 306, and define the first, second, third, and fourth regions 902a-d having varying cross-sectional diameters 906, 908 and providing contiguous portions of the coil 1204, such that the windings or loops of the filament 302 axially continue uninterrupted along the length of the coil 1204.

The first region 902a may be characterized as a proximal region, or at least closer to the surgeon than the other identified regions 902b-d. Moreover, the first region 902a may have an axial length 1202 that spans a larger distance than the other axial lengths 910, 912. As a result of the increased diameter 906, the first region 902a may exhibit a flexibility that is greater than the remaining regions 902b,d. As can be appreciated by those skilled in the art, this may prove advantageous especially when deploying the coil 1204 as a finishing coil within an aneurysm. As a finishing coil, the coil 1204 may need to be more flexible at its proximal region so that the proximal region is better able to flex, bend, and fill in the interstitial spaces within the aneurysm left by the more stiff distal regions of the coil 1204.

Figure 13:
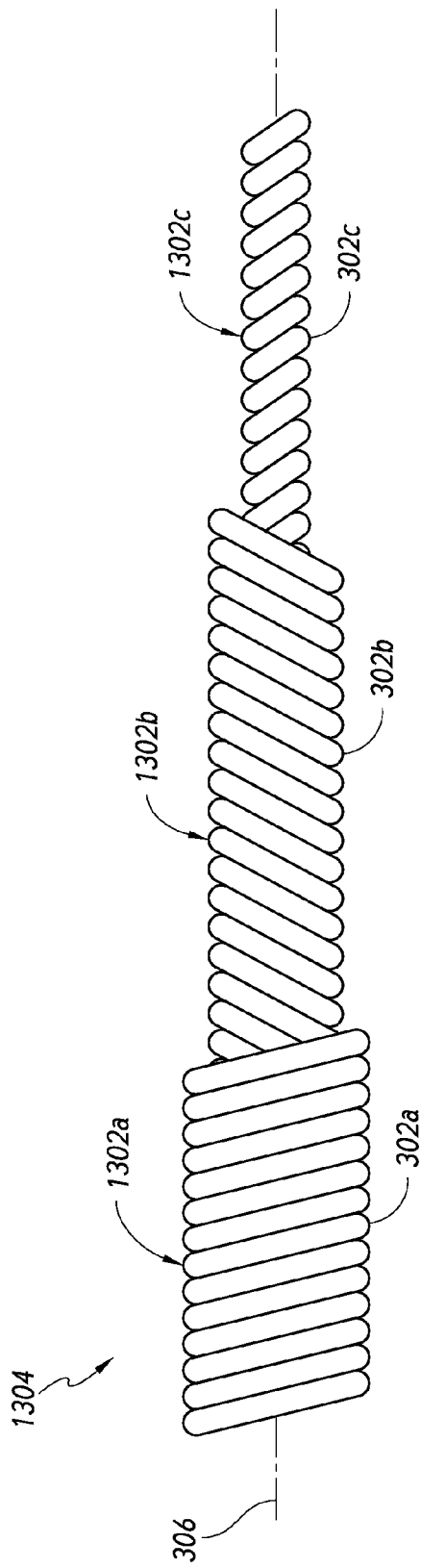
FIG. 13 illustrates a side view of an exemplary coiled implant that may be used in conjunction with the system of FIG. 2a or 2b, in accordance with various embodiments of the subject technology.

Referring now to FIG. 13, illustrated is another exemplary coiled implant 1304, according one or more embodiments of the disclosure. The coiled implant 1304 may be used in conjunction with the systems 10, 100 described herein with reference to FIGS. 2a-c and may be similar in some respects to the coiled implant 604 described above with reference to FIG. 6. Accordingly, the coiled implant 1304 may be best understood with reference to FIG. 6 and other figures discussed herein, where like numerals refer to like components that will not be described again in detail. The coiled implant 1304 may include a plurality of coils, wherein at least one coil is nested within another coil. In particular, the coiled implant 1304 may include a first coil 1302a, a second coil 1302b, and a third coil

1302c, where each coil 1302a-c extends axially along the longitudinal axis 306. As illustrated, the second coil 1302b may be concentric with the first coil 1302a and configured to at least partially nest within the first coil 1302a, and the third coil 1302c may be concentric with the second coil 1302b and configured to at least partially nest within the second coil 1302b. As a result, the first and third coils 1302a,c may also be considered concentrically-disposed with respect to each other. In one or more embodiments, the coiled implant 1304 may consist of only two coils, such as the first and second coils 1302a,b. In other embodiments, the coiled implant 1304 may include more than the three coils 1302a-c, without departing from the scope of the disclosure.

The first coil 1302a may be made from the first filament 302A wound multiple times about the longitudinal axis 306. In like manner, the second and third coils 1302b,c may be made from the second and third filaments 302B and 302C, respectively, and likewise wound multiple times about the longitudinal axis 306. As with prior embodiments, however, the first, second, and third coils 1302a-c may be unifilar or multifilar, without departing from scope of the disclosure. In some embodiments, the filaments 302A-C may be made of the same material and, besides having different respective cross-sectional diameters to facilitate the indicated nested relationship, otherwise exhibit substantially the same structural characteristics. In other embodiments, however, one or all of the filaments 302A-C may be different in one or more filament characteristics, thereby providing different filament lateral flexibilities along different axial regions of the coiled implant 1304.

For example, in one or more embodiments, the windings of the first filament 302A may be formed in a generally circular or oval cross-sectional shape, and the windings of the second filament 302B may be formed in a generally polygonal cross-sectional shape, such as a triangular or a rectangular cross-sectional shape. In other embodiments, each filament 302A,B may be formed using different circular or oval cross-sectional shapes or different polygonal cross-sectional shapes. It will be appreciated that any variation of cross-sectional shapes may be used, without departing from the scope of the disclosure. Moreover, it will further be appreciated that the third filament 302C may equally be formed using varying circular or oval cross-sectional shapes or varying polygonal cross-sectional shapes when interacting with the second coil 1302b and its corresponding filament 302B.

In some embodiments, the general direction of the windings of each of the filaments 302A-C may be the same or may be varied, depending on the application. For example, the direction of the windings of the first and third filaments 302A,C may be in a first direction, such as clockwise, and the direction of the windings of the second filament 302B may be in a second direction, such as counterclockwise. As a result, the coiled implant 1304 may be characterized as a counter-wound coil, where the windings of the second coil 1302b are wound in an opposite sense from the windings of the first and third coils 1302a,c. This configuration may prove advantageous in preserving torqueability of the coiled implant 1304, where, upon torquing the coiled implant 1304, radial expansion of one or more of the filaments 302A-C is substantially resisted by a biased set of adjacent filaments comprising one or more of 302A-C, tending to more tightly compress at least two of coils 1302a-c against each other. In some embodiments, the rotational orientation of the cross-sectional shape of the second coil 1302b may vary along the longitudinal axis 306.

The pitch between adjacent filaments 302A-C in each coil 1302a-c may also vary, depending on the application. In some embodiments, for example, the pitch may be varied such that the engagement between nested coils 1302a-c may be optimized to operate much like nested helical gears. As a result, torqueability between adjacent coils 1302a-c will be maximized.

The coiled implant 1304 may be deployed via several methods. In some embodiments, the coiled implant 1304 may be deployed by first advancing at least a portion of the coiled implant 1304 into a target treatment site, such as an aneurysm. As described above, the coiled implant 1304 may include a plurality of concentric coils 1302a-c. In one or more embodiments, only two coils may be used in the coiled implant 1304, but in other embodiments, more than three coils may be used, without departing from the scope of the disclosure. Moreover, each of the coils 1302a-c may have a respective winding direction, where at least two of the coils 1302a-c have opposing winding directions.

The method may further include providing torque to at least one of the concentrically-nested coils 1302a-c such that at least one of the coils 1302a-c radially expands or contracts and thereby transfers a portion of the applied torque to a radially adjacent coil 1302a-c. In one or more embodiments, providing torque to the coils 1302a-c includes rotating the coiled implant 1304 while positioning the coiled implant 1304 in the aneurysm. In some embodiments, rotating the coiled implant 1304 may cause the coiled implant 1304 to form a loop by overlapping with itself. Rotating the coiled implant 1304 may also result in expansion of the coiled implant 1304 into a configuration that contacts a wall of the aneurysm at multiple points. Rotating the coiled implant 1304 may also result in an increased packing density of the coiled implant 1304 in the aneurysm.

Providing torque to the coils 1302a-c may include rotating a delivery system (not shown) that may be attached or otherwise coupled to the coiled implant 1304. The delivery system may be attached to the coiled implant 1304 by a coupling, for example, that restricts relative rotation between the coiled implant 1304 and the delivery system. For example, the coupling can include an interference fit, a locking engagement, mechanical attachments, welding and/or brazing coupling attachments, adhesive attachments, combinations thereof, or the like between the implant 1304 and the delivery system. In one embodiment, the coupling may be configured to transfer torque from the delivery system to the implant 1304 until being appropriately detached from the delivery system. In one or more embodiments, the relative rotation between the coiled implant 1304 and the delivery system may be limited to less than about 360°, about 180°, about 120°, about 90°, about 60°, about 45°, about 30°, about 20°, about 10°, about 5°, or about 2° of rotation.

In some aspects of the disclosure, a method of manufacturing a coiled implant, such as the coiled implants 604 and/or 1304 described above with reference to FIGS. 6 and 13, is disclosed. It will be appreciated, however, that various facets of the method may equally apply to the manufacture of any of the coils or implants described herein. The method may include winding a first filament to form a first coil, the first coil defining an inner lumen that extends longitudinally. In some embodiments, the first filament may be coupled to or otherwise grouped with another one or more types or configurations of filament, or similar filaments, thereby providing for the manufacture of a multifilar coil. Otherwise, the first coil may be characterized as a unifilar coil. The first filament(s) may be wound into a substantially helical tubular shape, forming a primary coil shape, and subsequently heat treated to retain the first filament in the primary coil shape.

As used herein, a "primary" shape includes, but is not limited to, the initial forming of a filament into a shaped structure, such as a tubular shape. For example, primary shapes may be indicative of the various cross-sectional shapes of the coiled implants or coils generally described herein with reference to FIGS. 7*a-c* and 8. In other embodiments, the primary shape may be a simple cross-sectional shaped coil, such as a coil of circular primary cross-section. Generating a primary shape may also include the heat treating process for the filament, which may result in the forming and setting of the filament into one or more of the disclosed cross-sectional shapes.

The primary coil, formed by the helically wound first filament, may then be formed into a secondary shape. A "secondary" shape is formed using the primary shaped structure and creating a three-dimensional shape by, for example, wrapping the primary shaped structure around a mandrel and heat setting the primary shape in the wrapped disposition so the structure retains its primary coil shape as well as the secondary shape.

Some methods may further include winding a second filament to form a second coil. In some embodiments, the first and second filaments are made of the same material. In other embodiments, however, the first and second filaments may be made of different materials and may further exhibit different cross-sectional diameters. In at least one embodiment, the first filament is made of a metal. To form the second coil, the second filament may be wound about a mandrel and subsequently inserted into the inner lumen defined by the first coil. In at least one embodiment, the second coil is still wound about the mandrel when inserted into the inner lumen of the first coil. Once at least partially inserted within the inner lumen, the mandrel may be removed from engagement with the second coil. Inserting the second coil into the inner lumen of the first coil may occur either before or after the first coil is heat treated. In some embodiments, however, it may be advantageous to insert the second coil into the first coil after the first coil has been heat treated. In some embodiments, the heat treating of the first coil is at a condition that would change a physical, chemical, and/or biological characteristic of the second coil and thereby render the second coil unsuitable for treatment of the patient. In some instances, changing a physical characteristic of the second coil and thereby rendering the second coil unsuitable for treatment of a patient can include, without limitation, melting, annealing, evaporating, sublimating, singeing, causing a phase transition of, rendering inert, charring, and rendering non-biocompatible a material of the second coil. In such embodiments, it may be advantageous to combine the first and second coils after heat treatment of the first coil because subjecting the second coil to the heat treatment of the first coil may melt, anneal, evaporate, singe, cause an undesirable phase transition of, render inert, or otherwise render non-biocompatible the material of the second coil.

In some embodiments, instead of winding the second filament on a mandrel to form the second coil, the method may include winding the second filament directly onto the first coil, such as about its outer circumferential surface. In at least one embodiment, the second filament is wound onto the first coil after the first coil has been heat treated. Otherwise, as described above, the material of the second coil may be melted, annealed, evaporated, singed, forced through an unwanted phase transition, rendered inert, or otherwise rendered non-biocompatible as a result of the heat treatment of the first coil.

In some aspects, another method of manufacturing a coiled implant, such as the coiled implants 604 and/or 1304 described above with reference to FIGS. 6 and 13, is disclosed. It will be appreciated, however, that various facets of this additional method may equally apply to the manufacture of any of the coils or implants described herein, without departing from the scope of the disclosure. The method may include winding a first filament to form a first coil. In some embodiments, the first filament may include more than one filament, thereby providing for the manufacture of a multifilar coil. Otherwise, the first coil may be characterized as a unifilar coil. The first filament may be wound into a substantially helical tubular shape and subsequently heat treated to form one of a primary shape and a secondary shape, such as any of the various cross-sectional shapes generally described herein.

In one or more embodiments, the first filament may be wound such that it has an increased pitch and/or defines a helical gap between one or more of the windings. As will be appreciated, the helical gap(s) along the length of the first coil may vary, depending on the application, and may provide a space for subsequently winding one or more second filaments into the gap. In such coils the size of the gap will be approximately equal to the aggregate width of the one or more second filaments to be wound into the gap. Depending on the application, the width of the resulting gap may be varied. In some embodiments, for instance, the width of the gap may be about 20% of the width of the second filament. In other embodiments, the width of the gap 610 may be about 40%, about 60%, about 80%, about 100%, about 150%, or about 200% of the width of the second filament. The method may further include winding a second filament into the helical gap(s), thereby forming a second coil that is interwound with the first coil. For example, in a 2:8 coil (2 filaments of one type and 8 filaments of another type), the 8 filaments might be wound next to each other with a gap between adjacent turns of the group of 8 filaments. The 8 filaments may then be heat treated, and the remaining 2 filaments can be wound into the gap ("interwound"). In some embodiments, the first and second filaments are made of the same material. In other embodiments, however, the first and second filaments may be made of different materials.

In some embodiments, the second filament is wound into the helical gap(s) after the first coil has been heat treated. Otherwise, as described above, the material of the second coil may be melted, annealed, evaporated, singed, forced through an unwanted phase transition, rendered inert, or otherwise rendered non-biocompatible as a result of the heat treatment of the first coil. In other embodiments, the first and second filaments are heat treated together to form the coil or coiled implant. Heat treating the first filament may impart a primary shape to the first coil, and heat treating the second filament may impart a secondary shape to the second coil.

In some aspects of the disclosure an exemplary coil is disclosed. The coil may be representative of any of the coiled implants or coils disclosed herein. In one or more embodiments, the coil may include a coil winding made of at least a first material and a second material. After being formed or otherwise shaped into a first coil, the first material may be heat treated under conditions that would melt, anneal, evaporate, singe, destroy, alter, render non-biocompatible, or otherwise compromise the properties of the second material. The coil winding may include primary and secondary coil windings, where the heat treatment imparts a primary shape to the primary coil winding and simultaneously imparts a secondary shape to the secondary coil winding.

Whereas the first material is formed to make the first coil, the second material may be formed to make a second coil. In one or more embodiments, the first and second coils may each exhibit an increased pitch or otherwise define helical gaps between adjacent filaments such that the first and second coils may be interwound to form the exemplary coil. In at least one embodiment, the second coil may be interwound with the first coil after the first coil is heat treated.

In some aspects, another exemplary coil is disclosed. Again, the exemplary coil may be representative of any of the coiled implants or coils disclosed herein. The coil may include a first coil winding that has a first secondary shape. In at least one embodiment, the first coil may be heat treated to obtain the first secondary shape. The coil may also include a second coil winding that may be wound over the first coil winding. The second coil winding may exhibit a second secondary shape, where the second secondary shape is different from the first secondary shape. In at least one embodiment, the second coil winding is wound over the first coil winding after the first coil winding is heat treated to obtain the first secondary shape.

Figure 14:
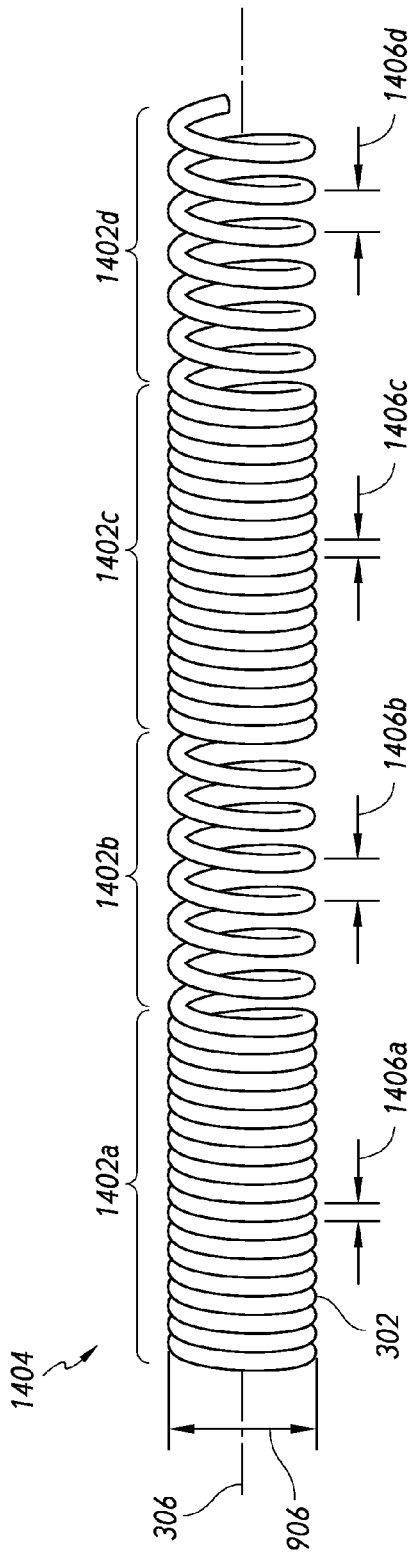
FIG. 14 illustrates a side view of another exemplary coiled implant that may be used in conjunction with the system of FIG. 2a or 2b, in accordance with various embodiments of the subject technology.

Referring now to FIG. 14, illustrated is another exemplary coil 1404 that may be used in conjunction with the systems 10, 100 (FIGS. 2a-c), according to one or more embodiments. The coil 1404 may be similar in some respects to the coils 904, 1204 described above with reference to FIGS. 9 and 12, and one or more of the other coils or coiled implants described herein. Accordingly, the coil 1404 may be best understood with reference to FIGS. 9 and 12, and other figures discussed herein, where like numerals refer to like components that will not be described again. Similar to the coils 904, 1204 described above, the coil 1404 may be formed by a plurality of windings of one or more filaments 302 that are wound about the longitudinal axis 306 to form a generally tubular structure. The coil 1404 may exhibit a cross-sectional diameter 906 across at least a portion of its length. In one embodiment, the cross-sectional diameter 906 is constant along the entire length of the coil 1404.

The coil 1404 may further include a series of contiguous regions, such as a first region 1402a, a second region 1404b, a third region 1404c, and a fourth region 1404d. Each region 1402a-d may be axially-spaced along the length of the coil 1404 such that the windings of the filament 302 continue uninterrupted along the axial length of the coil 1404. As with prior embodiments, it will be appreciated that the coil 1404 may be formed of more or less regions 1402a-d without departing from the scope of the disclosure.

As illustrated, the pitch of the coil 1404 may vary across the length of the coil 1404. For example, the first region 1402a may exhibit a first pitch 1406a between adjacent windings, the second region 1402b may exhibit a second pitch 1406b between adjacent windings, the third region 1402c may exhibit a third pitch 1406c between adjacent windings, and the fourth region 1402d may exhibit a fourth pitch 1406d between adjacent windings. In some embodiments, two or more of the pitches 1406a-d may be the same. In other embodiments, however, each pitch 1406a-d may be different from the other pitches 1406a-d. As will be appreciated by those skilled in the art, varying the pitch 1406a-d along the length of the coil 1404 may impact deliverability of the coil 1404 due to its varying compressibility. Moreover, varying the pitch 1406a-d along the length of the coil 1404 may be configured to vary the softness and create break points (i.e., localized segments of easier lateral bending relative to adjacent coil segments) along the coil 1404.

Figure 15:
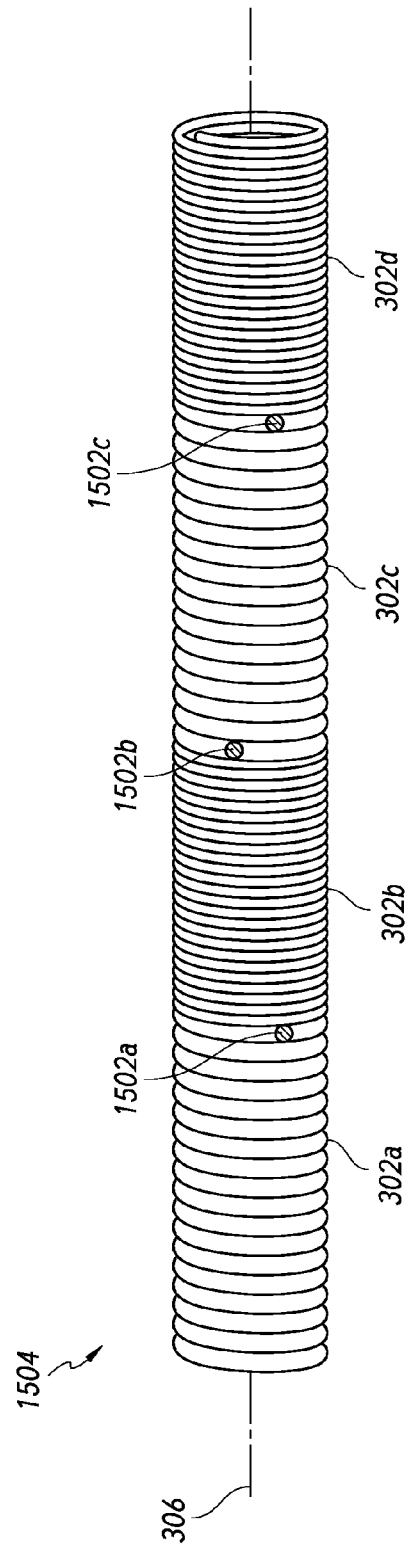
FIG. 15 illustrates a side view of another exemplary coiled implant that may be used in conjunction with the system of FIG. 2a or 2b, in accordance with various embodiments of the subject technology.

Referring now to FIG. 15, illustrated is another exemplary coil 1504 that may be used in conjunction with the systems 10, 100 (FIG. 2a-c), according to one or more embodiments. The coil 1504 may be similar in some respects to the coil 904 described above with reference to FIG. 9, and one or more of the other coils or coiled implants described herein. Accordingly, the coil 1504 may be best understood with reference to FIG. 9, and other figures discussed herein, where like numerals refer to like components that will not be described again in detail. Similar to the coil 904 described above, the coil 1504 may be formed by a plurality of windings of one or more filaments 302 that are wound about the longitudinal axis 306. Specifically, the coil 1504 may be made of at least a first filament 302A, a second filament 302B, a third filament 302C, and a fourth filament 302D, where each filament 302A-D is axially-spaced from each other and contiguous along the length of the coil 1504. As with prior embodiments, the coil 1504 may include more or less than four filaments 302A-D, and may include groupings or pluralities of filaments 302A-D, such as is disclosed above with reference to FIG. 4a.

In some embodiments, the filaments 302A-D may be made of different materials and/or otherwise exhibit different structural characteristics. For example, the material, thickness, or cross-sectional shape of the first filament 302A may be different than that of the second filament 302B, or the third or fourth filaments 302C,D. In other embodiments, other characteristics of the filaments 302A-D may be different or varied. In at least some embodiments, two or more of the filaments 302A-D may exhibit at least some of the same characteristics, such as material, thickness, or cross-sectional shape.

The first filament 302A may be coupled to the second filament 302B at a first coupling location 1502a. Moreover, the second filament 302B may be coupled to the third filament 302C at a second coupling location 1502b, and the third filament 302C may be coupled to the fourth filament 302D at a third coupling location 1502c. In some embodiments, the coupling locations 1502a-c may be welds or weld joints between adjacent filaments 302A-D. In other embodiments, the coupling locations 1502a-c may be mechanical fasteners, adhesives, heat treated zones, combinations thereof, or the like, in order to couple adjacent filaments 302A-D together so as to create a contiguous coil winding. It will be appreciated that different materials, thicknesses, or diameters of the filaments 302A-D may be interspersed along the length of the coil 1504, without departing from the scope of the disclosure.

Figure 16:
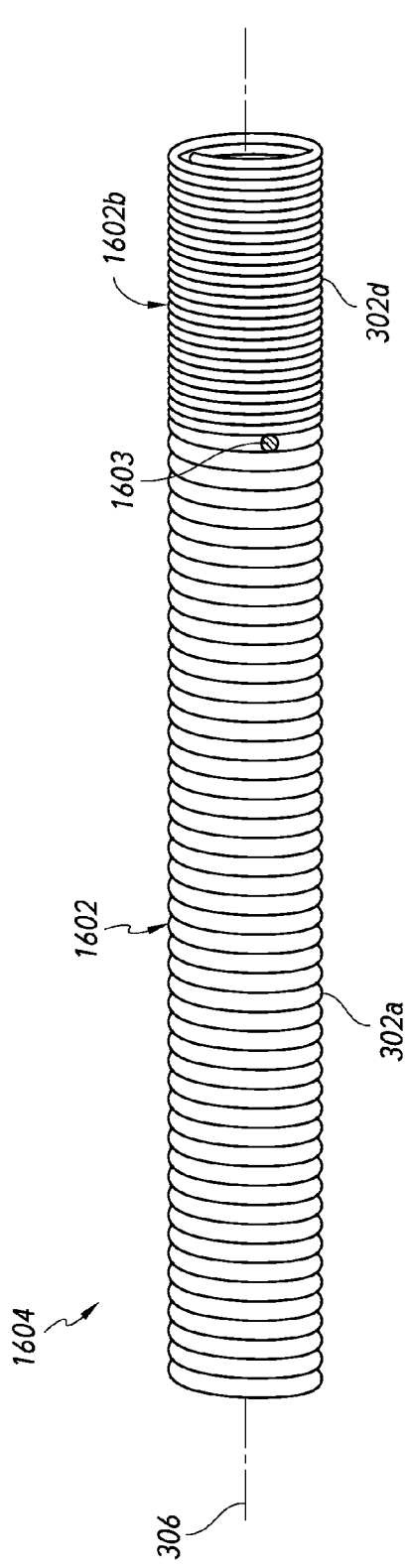
FIG. 16 illustrates a side view of another exemplary coiled implant that may be used in conjunction with the system of FIG. 2a or 2b, in accordance with various embodiments of the subject technology.

Referring to FIG. 16, with continued reference to FIG. 15, illustrated is another exemplary coil 1604, according to one or more embodiments disclosed. The coil 1604 may be similar to the coil 1504 described above with reference to FIG. 15, except that only two filaments 302A,B are shown as being used to form the coil 1602. Specifically, the coil 1604 may include a proximal portion 1602a and a distal portion 1602b, where the first filament 302A makes up the proximal portion 1602a and the second filament 302B makes up the distal portion 1602b. The proximal and distal portions 1602a,b may be coupled together at a coupling location 1603. The coupling location 1603 may be substantially similar to the coupling locations 1502a-c described above, and therefore may consist of welds, mechanical fasteners, adhesives, heat treated zones, combinations thereof, or the like, in order to couple the adjacent filaments 302A,B together so as to create a contiguous coil winding.

In the illustrated embodiment, the filaments 302A,B may be made of different materials or otherwise exhibit different filament characteristics, such as wire diameter. For example, the second filament 302B may exhibit a finer wire diameter than the first filament 302A. As a result, the second filament 302B may be more soft or pliable than the first filament 302A. This may prove advantageous where the second portion 1602b of the coil 1604 is the distal end of the coil 1604 and the softer second filament 302B provides an atraumatic end for the coil 1604 that is designed to prevent injury to the vasculature of the patient as it is moved within the vasculature. This may also prove advantageous where the second portion 1602b of the coil 1604 is the proximal end of the coil 1604 and the softer second filament 302B provides an atraumatic end for the coil 1604 that is easily packed into remaining open interstices of the deployed coil.

Figure 17:
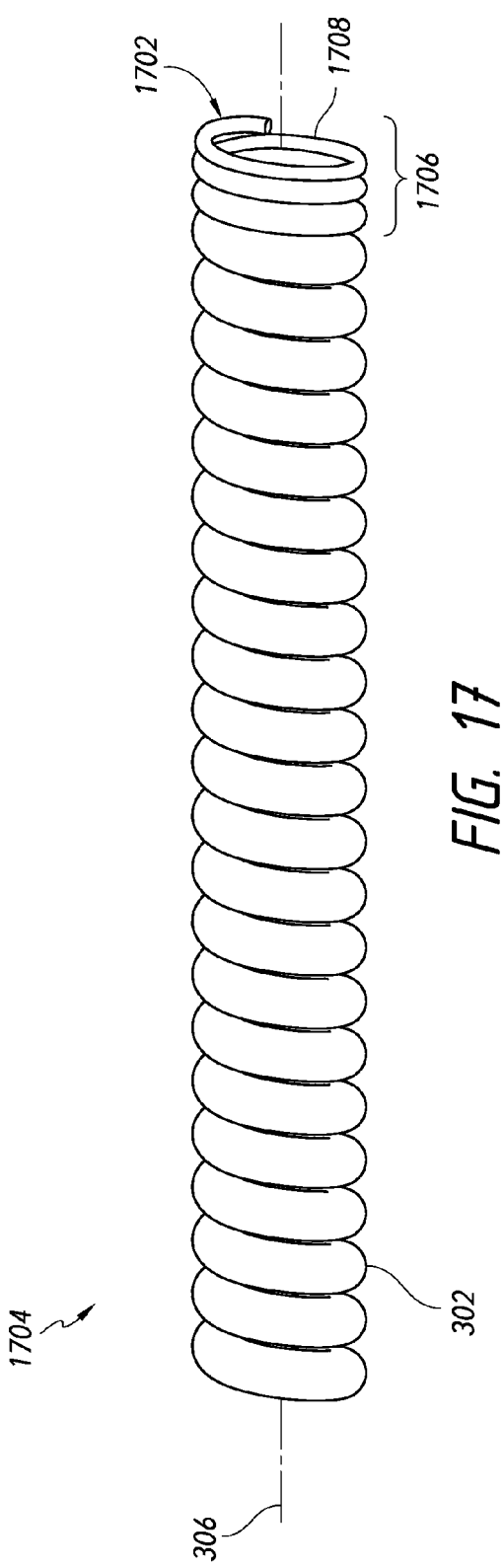
FIG. 17 illustrates a side view of another exemplary coiled implant that may be used in conjunction with the system of FIG. 2a or 2b, in accordance with various embodiments of the subject technology.

Referring now to FIG. 17, with continued reference to FIGS. 15 and 16, illustrated is another exemplary coil 1704, according to one or more embodiments disclosed. The coil 1704 may be similar in some respects to the coils 1504, 1604 described above with reference to FIGS. 15 and 16. For example, similar to the coils 1504, 1604 described above, the coil 1704 may be formed by a plurality of windings of one or more filaments 302 wound about the longitudinal axis 306. As with prior embodiments, the coil 1704 may include more than a single type or configuration of filament 302, and may further include groupings or pluralities of filaments 302, such as is disclosed above with reference to FIG. 4a.

The coil 1704, however, may have a distal end 1702 where the windings spanning a distal portion of the coil 1704 have been altered to fit a specific application. For instance, the windings at the distal portion 1706 may be tapered or otherwise ground such that the diameter of the filament 302 over the distal portion 1706 is reduced or gradually decreases in the distal direction. In at least one embodiment, the distal portion 1706 may span two or more windings of the filament 302. Moreover, the end 1708 of the filament 302 may be turned into the interior of the coil 1704. As a result, the distal portion 1706 may provide a soft and atraumatic distal end 1702 for the coil 1604 that is designed to prevent injury to the vasculature of the patient. Alternatively the portion 1706 of the coil 1704 is the proximal end of the coil 1704 and the reduced diameter filament 302 provides an atraumatic end for the coil 1704 that is easily packed into remaining open interstices of the deployed coil.

Figure 18:
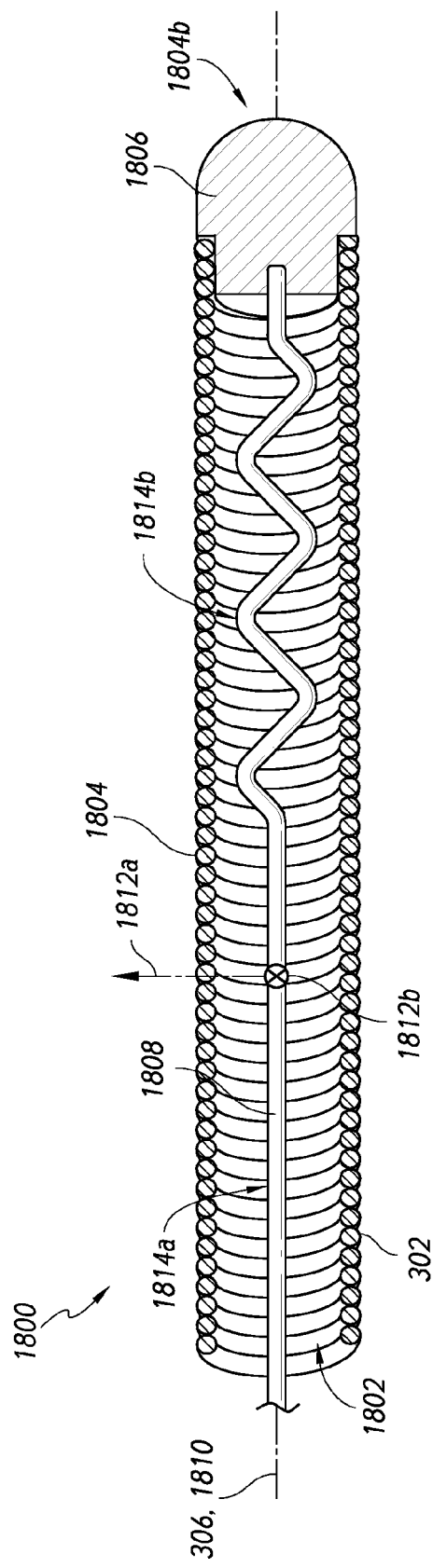
FIG. 18 illustrates a partial cross sectional view of an exemplary system for treating vascular disease, according to one or more embodiments disclosed.

Referring now to FIG. 18, illustrated is an exemplary system 1800 for treating vascular disease, according to one or more embodiments. The system 1800 may be used in conjunction with the systems 10, 100 described above with reference to FIGS. 2a-c. As illustrated, the system 1800 may include a coil implant 1804 extending longitudinally about a longitudinal axis 302. The coil implant 1804 may be somewhat similar to the coil implants and coils disclosed herein and will therefore reference similar numerals and references for brevity. The coil implant 1804 is made from a filament 302 wound multiple times about the longitudinal axis 306 to form a generally tubular structure that defines a lumen 1802 therein. As with prior embodiments, the filament 302 may be combined with one or more additional filaments 302, without departing from the scope of the disclosure.

The system 1800 may further include a distal tip 1806 arranged at a distal end 1804b of the coil implant 1804. In some embodiments, the distal tip 1806 may be substantially similar to the distal tip 204 described above with reference to FIG. 2c. The distal tip 1806 may be coupled to the coil 1804 by threading, welding, mechanical fasteners, adhesives, combinations thereof, or the like. The distal tip 1806 may be made of various materials, such as plastics, and may provide an atraumatic tip for the coil 1804, such that the coil 1804 does not damage the vasculature of the patient as the coil 1804 is positioned at the treatment site.

The system 1800 may further include a securing member 1808 extending within the lumen 1802 defined by the coil implant 1804. The securing member 1808 may be somewhat similar to the retaining element 112 described above with reference to FIGS. 2b and 2c. The securing member 1808 may be made of a variety of materials such as, but not limited to, polymers, metals, wires, tubes, filaments, braided filaments, coated filaments, combinations thereof, or the like. In at least one embodiment, the securing member 1808 may either be made of or coated with one or more bioactive materials.

In some embodiments, the securing member 1808 may serve to maintain the coil implant 1804 in its elongated form during delivery and implantation of the implant 1804. To this end, the securing member 1808 may be loosely, but at least easily detachably arranged within the coil implant 1804 such that it may be removed from within the lumen 1802 without difficulty when required. Upon removing the securing member 1808, the coil implant 1804 may be free to assume a predetermined, superimposed configuration.

In other embodiments, however, the securing member 1808 is configured to remain within the coil implant 1804 permanently. In such embodiments, the securing member 1808 may be coupled to the distal tip 1806 of the coil implant 1804, as illustrated. In other embodiments, however, the securing member 1808 may be coupled to other portions of the coil implant 1804 or free-floating within the lumen 1802, without departing from scope of the disclosure.

The securing member 1808 may have a central axis 1810 which aligns generally with the longitudinal axis 302 of the coil implant 1804. The securing member 1808 may further include a first transverse axis 1812a and a second transverse axis 1812b (i.e., pointing directly out of the page). The second transverse axis 1812b may be normal to the first transverse axis 1812a, and each of the first and second transverse axes 1812a,b may be normal to both the longitudinal axis 302 and the central axis 1810. In operation, the securing member 1808 may be at least partially configured to maintain the coil implant 1804 in its elongated form, or not at all, depending on the application.

The securing member 1808 may also serve as a stretch resistant member, thereby preventing the coil implant 1804 from undesirable elongation over predetermined regions of the coil implant 1804. Specifically, the securing member 1808 may include one or more stretch resistant regions 1814a and one or more pliant regions 1814b. As illustrated, the stretch resistant region 1814a may be a straight or otherwise elongate length of the securing member 1808. The pliant region 1814b, on the other hand, may be "crinkled," e.g., forming undulations, helices, patterns of peaks and valleys, or combinations thereof, or otherwise compacted to some degree such that axial elongation of the securing member 1808 across the pliant region 1814b is possible. As a result, the coil implant 1804 may be able to correspondingly flex across the axial length of the pliant region 1814b until the undulating portion is straightened or is otherwise no longer able to elongate.

Referring now to FIGS. 19a and 19b, with continued reference to FIG. 18, illustrated are alternative exemplary configurations of the securing member 1808, according to one or more embodiments. As illustrated in FIG. 19a, the pliant region 1814b may be helically twisted about the central axis 1810 of the securing member 1808, thereby forming a series of axially-spaced coils. In at least one embodiment, the coils of the pliant region 1814b may be formed in substantially the same way as the windings of the filament 302 for the coil implant 1804, e.g., wound about a mandrel and/or otherwise heat treated into a set shape. In operation, the coils allow the pliant region 1814b to axially-elongate and correspondingly allow the coil implant 1804 to flex across the axial length of the pliant region 1814b until the coils are straightened or are otherwise no longer able to elongate.

FIG. 19b depicts an embodiment having multiple stretch resistant regions 1814a and multiple pliant regions 1814b.

Those skilled in the art will appreciate the advantages of providing stretch resistance over certain parts of the coil implant 1804, such as its proximal regions, while allowing a degree of elongation or softening over other regions, such as its distal regions. While a configuration having alternating stretch resistant and pliant regions 1814*a,b* is illustrated in FIG. 19*b*, it will be appreciated that various configurations of stretch resistant and pliant regions 1814*a,b* may be employed without departing from the scope of the disclosure. Moreover, the pitch between adjacent coils in the pliant region(s) 1814*b* may be increased or decreased to manipulate the flexibility of the pliant region(s) 1814*b*.

Referring to FIGS. 19*c* and 19*d*, with continued reference to FIGS. 18 and 19*a-b*, illustrated are cross-sectional views of the coil implant 1804 with an exemplary securing member 1808 arranged therein, according to one or more embodiments. As depicted, the securing member 1808 may exhibit various axial cross-sectional shapes (i.e., shapes defined normal to the central axis 1810). For example, as depicted in FIG. 19*c*, the securing member 1808 may exhibit a polygonal cross-sectional shape normal to the central axis 1810. The polygonal cross-sectional shape may be substantially rectangular or another suitable polygonal shape. In other embodiments, such as is depicted in FIG. 19*d*, the securing member 1808 may have a circular or arcuate cross-sectional shape normal to the central axis 1810. In one or more embodiments, exemplary circular or arcuate cross-sectional shapes may be substantially oval or substantially elliptical.

Using the securing member 1808 with varying cross-sectional shapes may prove advantageous since it will tend to provide a preferred direction of bending of the coil implant 1804 in a predetermined direction. As a result, in the event the securing member 1808 is twisted along its central axis 1810, then the direction of easy lateral bending for the attendant coil may correspondingly spiral along the axial length of the coil.

Referring now to FIGS. 20*a*-20*d*, illustrated are exemplary configurations for a multifilar coil 2004, according to one or more embodiments disclosed. As with prior embodiments, the multifilar coil 2004 may be used in conjunction with the systems 10, 100 (FIGS. 2*a-c*). The multifilar coil 2004 may be somewhat similar to the multifilar coil 404 described above with reference to FIG. 4*a* and the other coils and implants discussed herein. Accordingly the multifilar coil 2004 may be best understood with reference to FIG. 4*a*, where like numerals indicate like elements that will not be described again in detail. The multifilar coil 2004 may include a distal tip 2002, which may be substantially similar to the distal tip 204 described above with reference to FIG. 2*c*, and a stretch resistant member (not shown) which may be substantially similar to the securing member 1808 as described herein with reference to FIGS. 18 and 19*a-d*. The multifilar coil 2004 may further include at least a first filament 302A and a second filament 302B, but it will be appreciated that any number of filaments 302 may be used without departing from the scope of the disclosure.

The multifilar coil 2004 may include one or more first pluralities 2006*a* of adjacent first filaments 302A interchangeably followed by a corresponding one or more second pluralities 2006*b* of adjacent second filaments 302B. The pluralities 2006*a,b* may extend axially in a repeating configuration along at least a portion of the axial length of the multifilar coil 2004. In some embodiments, the first filament 302A is softer or otherwise more bendable than the second filament 302B, which is more stiff. As a result, the first pluralities 2006*a* made up of helically wound first filaments 302A may provide a corresponding first helically wound region, defined by at least a portion of the helically wound first filaments 302A, along a first portion of the axial length of the multifilar coil 2004. The second pluralities 2006*b*, made of helically wound second filaments 302B, provides a second helically wound region, defined by at least a portion of the helically wound second filaments 302B. The first region, since it is made of softer and more bendable filaments than the second region, may provide a coil flexibility at the first region that is more prone to lateral bending in a direction for a given force (i.e., a break point) than a coil flexibility at the second region in the same direction with the same force. Consequently, the break point of the multifilar coil 2004 may spiral along the length of the coil.

Figure 20A:
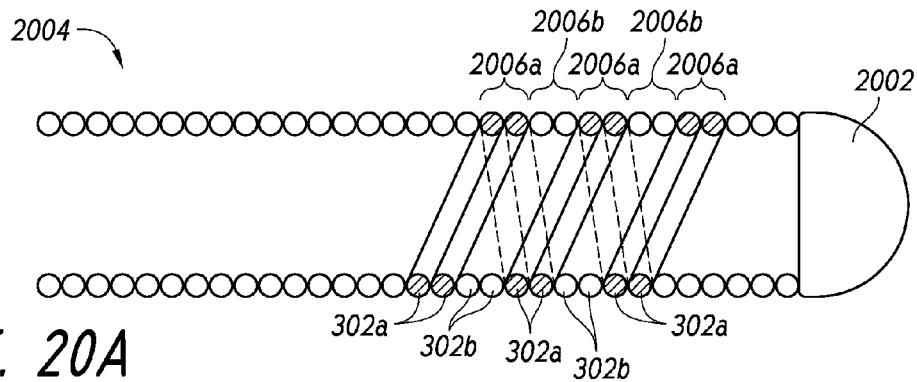
FIGS. 20a, 20b, 20c, and 20d illustrate partial cross-sectional side views of exemplary configurations of a multifilar coil that can be used in conjunction with the systems of FIGS. 2a and 2b, in accordance with various embodiments of the subject technology.
Figure 20B:
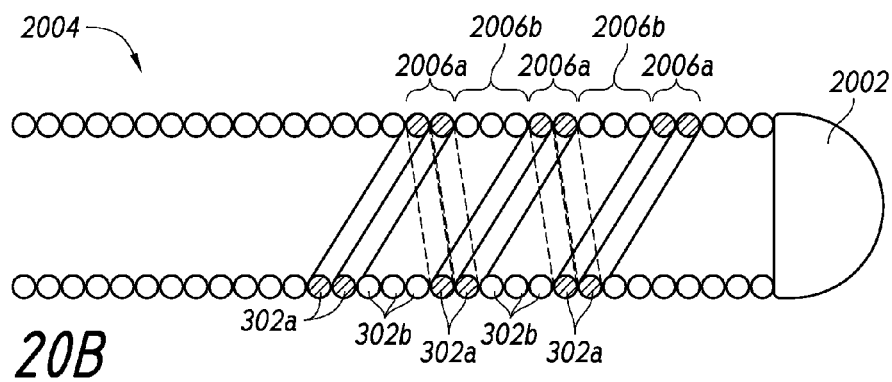
Figure 20C:
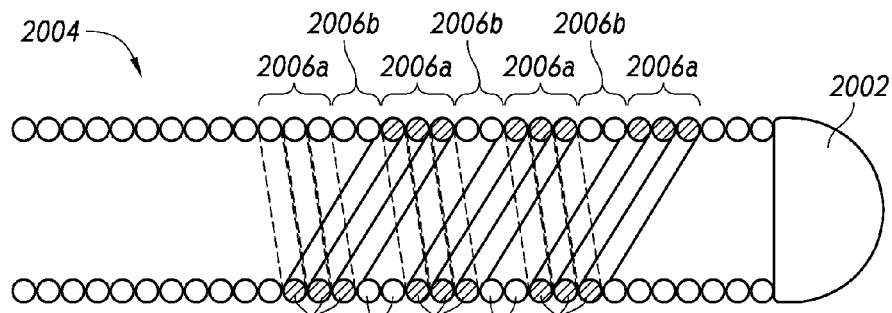
Figure 20D:
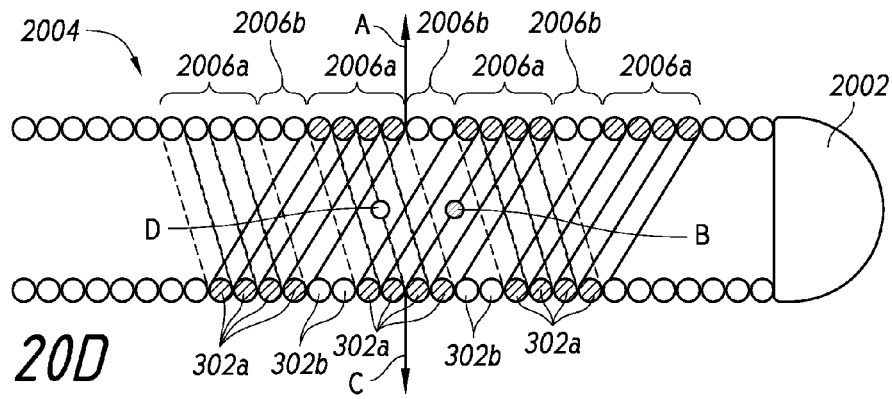

As an example of this spiraling break point, as experienced by the interaction between the softer first filaments 302A and the more stiff second filaments 302B, reference is made to the coil 2004 of FIG. 20*d*. Arrow A in FIG. 20*d* illustrates the direction of easiest bending when the coil is bent within the plane of the page, such that arrow A extends from the convex side of the bent coil. Such a bend would appear similar in shape to the bent coil depicted in FIG. 4*b*, creating a convex side along an outer edge of the bend (i.e., a top side of the coil as viewed by the reader in FIG. 4*b*), where filaments of the coil are depicted as separate from each other, and a concave side along an inner edge of the bend (i.e., a bottom side of the coil as viewed by the reader in FIG. 4*b*), where filaments of the coil are depicted as not separate from each other.

Likewise, arrow B (shown as a solid point) illustrates the direction of easiest bending when the coil is bent out of the plane of the page (i.e., the convex side extends out of the page toward the reader) in a plane that is both normal to the page and coincident with the coil longitudinal axis. As a result, arrow B extends from the convex side of the bent coil 2004 towards the reader.

Arrow C illustrates a direction of easiest bending when the coil 2004 is bent within the plane of the page in a manner opposite to that described above with respect to arrow A. Such a bend would appear opposite in shape to the bent coil depicted in FIG. 4*b*, creating a convex side along an outer edge (i.e., the bottom side of the coil as viewed by the reader in FIG. 4*b*) of the bend and a concave side along an inner edge (i.e., the top side of the coil as viewed by the reader in FIG. 4*b*) of the bend. Arrow C extends in the plane of the page from the convex side of the bent coil 2004.

Lastly, arrow D (shown as a hollow point) illustrates the direction of easiest bending when the coil 2004 is bent into the plane of the page (i.e., the convex side extends into the page away from the reader) in a plane that is both normal to the page and coincident with the coil longitudinal axis. As a result, arrow D extends from the convex side of the bent coil 2004 and away from the reader.

As can be observed from FIG. 20*d*, along the length of the coil 2004, the direction of easiest bending will spiral about the longitudinal axis of the coil 2004. For example, at a point along the axis coinciding with arrow D, the easiest direction of bending is into the page, as indicated by arrow D. At a slight distance distally of arrow D, for example at a point along the axis coinciding with arrow C, the direction of easiest bending has rotated and can be within the plane of the page and directed downward (as viewed in FIG. 20*d*), indicated by arrow C. At a slight distance distally of arrow C, for example at a point along the axis coinciding with arrow B, the direction of easiest bending has rotated and can be directed out of the page (i.e., toward the reader), as indicated by arrow B. At a slight distance distally of arrow B, for example at a point along the axis coinciding with arrow A, the direction of easiest bending has rotated and can be within the plane of the page and directed upward (as viewed in FIG. 20*d*), as indicated by arrow A. At intermediate points between those identified above, for example between the points coinciding with arrows D and C, the direction of easiest bending will be at an oblique angle relative to the plane of the page. Accordingly, along the length of the coil axis, the direction of easiest bending will helically rotate about the axis.

The ratio of first filaments 302A to second filaments 302B in the multifilar coil 2004 is partially indicative of the resulting flexibility or bendability of the coil 2004. For example, in an embodiment where the lateral flexibility of the second plurality 2006b is less than the lateral flexibility of the first plurality 2006a, the ratio of the number of first filaments 302A to the number of second filaments 302B can vary widely, from a ratio greater than one to a ratio less than one. It will be appreciated, however, that the ratio of filaments 302 is limited, since the total number of filaments 302 in the multifilar coil 2004 is geometrically limited by the coil primary diameter and filament diameter, as discussed above. Consequently, if the coil 2004 is geometrically limited to 10 filaments, for example, and the coil has a first plurality 2006a and a second plurality 2006b, then the ratio between first and second filaments 302A,B can be no greater than 8:2 and no less than 2:8.

For example, where the filament ratio<<1 (e.g., 2:8), the coil 2004 may be comprised predominantly of less flexible second filaments 302B and will therefore exhibit mechanical characteristics similar thereto. In such a coil 2004, it may be desirable for the more flexible filament (e.g., the first filament 302A) to provide certain important, non-mechanical properties along the length of the coil 2004. For example, the more flexible filament may be configured to be used as a thrombogenic surface, a surface structure highly receptive to tissue overgrowth, a drug depot which can elute medication over time, improve visualization (by X-ray, ultrasound, MRI, or other methods), combinations thereof, or other characteristics.

In embodiments where the filament ratio<<1 (e.g., 8:2), the coil 2004 may be comprised predominantly of more flexible first filaments 302A and will therefore exhibit mechanical characteristics similar thereto. In such a coil 2004 it may be desirable for the less flexible filament (e.g., the second filament 302B) to provide certain important mechanical properties along the length of the coil 2004. For example, the less flexible filament may be configured to provide mechanical strength, shape memory (whether by annealing, heat setting, or other means), resistance to prolapse out of the aneurysm neck, combinations thereof, or other characteristics.

In embodiments where the filament ratio ~1 (e.g., 5:5), the coil 2004 may be comprised of approximately equal numbers of less flexible second filaments 302B and more flexible first filaments 302A, and will therefore exhibit a mixture of mechanical characteristics. Coils having this approximate ratio of filaments may be especially suited to having a break point along the length of the coil 2004 in which the direction of easier bending describes a spiral along the length of the coil 2004. It will be appreciated, however, that the ratio of less flexible second filaments 302B to more flexible first filaments 302A will be chosen or otherwise determined for the particular application, with consideration of the lateral flexibilities of both the first and second filaments 302A,B, their number, and the coil primary diameter and cross sectional shape.

As illustrated in FIG. 20a, the multifilar coil 2004 may exhibit a 2:2 ratio filament pattern, where the first plurality 2006a includes two consecutive loops or windings of soft, first filaments 302A, and the second plurality 2006b includes two consecutive loops or windings of stiff, second filaments 302B. Accordingly, the filaments 302A-B are arranged in a repeating A-A-B-B pattern, and the pluralities 2006a,b correspondingly repeat the pattern contiguously over at least a portion of the axial length of the multifilar coil 2004.

As illustrated in FIG. 20b, the multifilar coil 2004 may exhibit a 2:3 ratio filament pattern, where the first plurality 2006a includes two consecutive loops or windings of first filaments 302A, and the second plurality 2006b includes three consecutive loops or windings of second filaments 302B. Accordingly, the filaments 302A-B are arranged in a repeating A-A-B-B-B pattern, and the pluralities 2006a,b correspondingly repeat the pattern contiguously over at least a portion of the axial length of the multifilar coil 2004.

As illustrated in FIG. 20c, the multifilar coil 2004 may exhibit a 3:2 ratio filament pattern, where the first plurality 2006a includes three consecutive loops or windings of first filaments 302A, and the second plurality 2006b includes two consecutive loops or windings of second filaments 302B. Accordingly, the filaments 302A-B are arranged in a repeating A-A-A-B-B pattern, and the pluralities 2006a,b correspondingly repeat the pattern contiguously over at least a portion of the axial length of the multifilar coil 2004.

As illustrated in FIG. 20d, the multifilar coil 2004 may exhibit a 4:2 ratio filament pattern, where the first plurality 2006a includes four consecutive loops or windings of first filaments 302A, and the second plurality 2006b includes two consecutive loops or windings of second filaments 302B. Accordingly, the filaments 302A-B are arranged in a repeating A-A-A-A-B-B pattern, and the pluralities 2006a,b correspondingly repeat the pattern contiguously over at least a portion of the axial length of the multifilar coil 2004.

As will be appreciated, the multifilar coil may exhibit any number of filament patterns without departing from the scope of the disclosure. For example, also contemplated herein is a 3:6 ratio pattern, a 2:4 ratio pattern, a 2:10 ratio pattern, a 8:2 ratio pattern, and a 8:4 ratio pattern, whereby the filaments 302A-B are arranged in repeating A-A-A-B-B-B-B-B-B, A-A-B-B-B-B, A-A-B-B-B-B-B-B-B-B-B-B, A-A-A-A-A-A-A-A-B-B, and A-A-A-A-A-A-A-A-B-B-B-B patterns, respectively, and the pluralities 2006a,b correspondingly repeat the patterns contiguously over at least a portion of the axial length of the multifilar coil 2004.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the description.

There may be many other ways to implement the subject technology. Various functions and elements described herein may be partitioned differently from those shown without departing from the scope of the disclosure. Various modifications to these configurations will be readily apparent to those skilled in the art, and generic principles defined herein may be applied to other configurations. Thus, many changes and modifications may be made to the subject technology, by one having ordinary skill in the art, without departing from the scope of the disclosure.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the description. Moreover, nothing disclosed herein is intended to be dedicated to the public regardless of whether such disclosure is explicitly recited in the above description.

What is claimed is:

1. A coiled implant, comprising:
   an outer coil arranged in a first winding formed by a first filament, the first winding having a circular or oval winding shape in a cross section transverse to a longitudinal axis of the implant; and
   an inner coil concentric within the outer coil and arranged in a second winding formed by a second filament, the second winding having a polygonal winding shape in a cross section transverse to the longitudinal axis;
   wherein the outer coil comprises the first filament and a third filament, and wherein a diameter of the first filament varies from a diameter of the third filament.

2. The coil of claim 1, wherein a direction of the first winding and a direction of the second winding direction are opposite.

3. The coil of claim 1, wherein the polygonal shape is triangular or rectangular.

4. The coil of claim 1, wherein a rotational orientation of the inner coil winding shape varies along a long axis of the inner coil.

5. The coil of claim 1, wherein a first region of the implant has a first flexibility permitting bending at the first region in a first direction relative to the long axis, the first flexibility being greater than a second flexibility permitting bending, in the first direction, of a second region of the implant that is spaced apart from the first region along a long axis of the implant.

6. The coiled implant of claim 1, wherein a pitch of the inner coil is at least twice a pitch of the outer coil.

7. The coiled implant of claim 6, wherein a pitch of the inner coil is at least four times a pitch of the outer coil.

8. A coiled implant, comprising:
   an outer coil arranged in a first winding formed by a first filament, the first winding having a first polygonal winding shape in a cross section transverse to a longitudinal axis of the implant; and
   an inner coil concentric within the outer coil and arranged in a second winding formed by a second filament, the second winding having a second polygonal winding shape in a cross section transverse to the longitudinal axis;
   wherein the outer coil comprises the first filament and a third filament, and wherein a diameter of the first filament varies from a diameter of the third filament.

9. The coil of claim 8, wherein a direction of the first winding and a direction of the second winding direction are opposite.

10. The coil of claim 8, wherein at least one of the first and second polygonal shapes is triangular or rectangular.

11. The coil of claim 8, wherein a rotational orientation of the inner coil winding shape varies along a longitudinal axis of the inner coil.

12. The coil of claim 8, wherein a first region of the implant has a first flexibility permitting bending at the first region in a first direction relative to the long axis, the first flexibility being greater than a second flexibility permitting bending, in the first direction, of a second region of the implant that is spaced apart from the first region along a long axis of the implant.

13. The coil of claim 8, wherein the first and second shapes are the same.

14. The coil of claim 8, wherein the first polygonal winding shape is different from the second polygonal winding shape.

15. The coiled implant of claim 8, wherein a pitch of the inner coil is at least twice a pitch of the outer coil.

16. The coiled implant of claim 15, wherein a pitch of the inner coil is at least four times a pitch of the outer coil.

* * * * *